(12) United States Patent
Fyfe

(10) Patent No.: US 10,301,288 B2
(45) Date of Patent: *May 28, 2019

(54) KINASE INHIBITORS

(71) Applicant: Topivert Pharma Limited, London (GB)

(72) Inventor: Matthew Colin Thor Fyfe, London (GB)

(73) Assignee: Topivert Pharma Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,996

(22) Filed: Dec. 4, 2017

(65) Prior Publication Data

US 2018/0086741 A1    Mar. 29, 2018

Related U.S. Application Data

(60) Division of application No. 15/207,915, filed on Jul. 12, 2016, now Pat. No. 9,850,233, which is a continuation of application No. 14/775,924, filed as application No. PCT/GB2014/050753 on Mar. 13, 2014.

(60) Provisional application No. 61/782,793, filed on Mar. 14, 2013.

(30) Foreign Application Priority Data

Aug. 16, 2013  (GB) .................................. 1314700.4
Dec. 20, 2013  (GB) .................................. 1322684.0

(51) Int. Cl.
| | |
|---|---|
| C07D 213/63 | (2006.01) |
| C07D 403/12 | (2006.01) |
| A61K 31/5377 | (2006.01) |
| C07D 401/14 | (2006.01) |
| C07D 401/12 | (2006.01) |
| A61K 31/4439 | (2006.01) |
| A61K 31/506 | (2006.01) |
| A61K 31/675 | (2006.01) |
| A61K 45/06 | (2006.01) |
| C07F 9/46 | (2006.01) |

(52) U.S. Cl.
CPC ........ *C07D 403/12* (2013.01); *A61K 31/4439* (2013.01); *A61K 31/506* (2013.01); *A61K 31/5377* (2013.01); *A61K 31/675* (2013.01); *A61K 45/06* (2013.01); *C07D 401/12* (2013.01); *C07D 401/14* (2013.01); *C07F 9/46* (2013.01)

(58) Field of Classification Search
CPC .. C07D 213/63; C07D 213/64; C07D 213/65; C07D 213/68; C07D 239/34
USPC .......................... 544/315, 319, 321; 546/297
See application file for complete search history.

(56) References Cited

U.S. PATENT DOCUMENTS

| | | |
|---|---|---|
| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |

(Continued)

FOREIGN PATENT DOCUMENTS

| | | |
|---|---|---|
| EP | 1 760 071 A1 | 3/2007 |
| EP | 2 578 582 A1 | 4/2013 |

(Continued)

OTHER PUBLICATIONS

U.S. Appl. No. 14/561,290, filed Dec. 5, 2014, Murray.

(Continued)

*Primary Examiner* — Deepak R Rao
(74) *Attorney, Agent, or Firm* — McCarter & English, LLP; Steven G. Davis

(57) ABSTRACT

There are provided compounds of formula (III), (III)

$$\overset{H}{\underset{H}{N}}-Z^2,$$

or a salt or protected derivative thereof, wherein $Z^2$ represents a structural fragment of formula (V), (V)

wherein $R^1$, $R^a$, $R^b$, X and Y have meanings given in the description, which compounds have antiinflammatory activity, for example through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

4 Claims, No Drawings

(56) References Cited

U.S. PATENT DOCUMENTS

| | | |
|---|---|---|
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Sun et al. |
| 7,582,638 B2 | 9/2009 | De Dios et al. |
| 7,678,811 B2 | 3/2010 | Dumas et al. |
| 7,750,160 B2 | 7/2010 | Milanov et al. |
| 7,767,670 B2 | 8/2010 | Mehta et al. |
| 7,790,756 B2 | 9/2010 | Flynn et al. |
| 7,838,524 B2 | 11/2010 | Lee et al. |
| 7,838,541 B2 | 11/2010 | Dumas et al. |
| 8,031,674 B2 | 10/2011 | Weniger et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,338,439 B2 | 12/2012 | Singh et al. |
| 8,450,335 B2 | 5/2013 | Singh et al. |
| 8,609,679 B2 | 12/2013 | Singh et al. |
| 8,618,140 B2 | 12/2013 | Ito et al. |
| 8,642,773 B2 | 2/2014 | Ito et al. |
| 8,653,305 B2 | 2/2014 | Habashita et al. |
| 8,710,222 B2 | 4/2014 | Singh et al. |
| 8,927,563 B2 | 1/2015 | Fyfe |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,212,181 B2 | 12/2015 | Singh et al. |
| 9,242,960 B2 | 1/2016 | Ito et al. |
| 9,249,125 B2 | 2/2016 | Duffy et al. |
| 9,447,076 B2 | 9/2016 | Longshaw et al. |
| 9,475,796 B2 | 10/2016 | Ito et al. |
| 9,481,648 B2 | 11/2016 | Baker et al. |
| 9,624,196 B2 | 4/2017 | Longshaw |
| 9,701,670 B2 | 7/2017 | Cariou |
| 9,771,353 B2 * | 9/2017 | Fyfe ................... C07D 403/12 |
| 9,890,185 B2 | 2/2018 | Fyfe et al. |
| 2003/0125354 A1 | 7/2003 | Hao et al. |
| 2003/0130309 A1 | 7/2003 | Moss et al. |
| 2004/0152725 A1 | 8/2004 | Moss et al. |
| 2005/0148605 A1 | 7/2005 | Grotzfeld et al. |
| 2005/0165024 A1 | 7/2005 | Milanov et al. |
| 2005/0165031 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0192314 A1 | 9/2005 | Mehta et al. |
| 2005/0197371 A1 | 9/2005 | Milanov et al. |
| 2005/0261315 A1 | 11/2005 | Mehta et al. |
| 2005/0267182 A1 | 12/2005 | Milanov et al. |
| 2006/0035922 A1 | 2/2006 | Mathias et al. |
| 2008/0207584 A1 | 8/2008 | Habashita et al. |
| 2008/0300281 A1 | 12/2008 | Dumas et al. |
| 2009/0131437 A1 | 5/2009 | Furet et al. |
| 2010/0029610 A1 | 2/2010 | Singh et al. |
| 2010/0160355 A1 | 6/2010 | DeGoey et al. |
| 2010/0168138 A1 | 7/2010 | DeGoey et al. |
| 2010/0173917 A1 | 7/2010 | Grotzfeld et al. |
| 2010/0249092 A1 | 9/2010 | Singh et al. |
| 2011/0118245 A1 | 5/2011 | Abraham et al. |
| 2011/0212962 A1 | 9/2011 | Ito et al. |
| 2011/0269800 A1 | 11/2011 | Ito et al. |
| 2011/0294812 A1 | 12/2011 | Ito et al. |
| 2011/0312963 A1 | 12/2011 | Ito et al. |
| 2012/0064060 A1 | 3/2012 | Habashita et al. |
| 2012/0136031 A1 | 5/2012 | Ito et al. |
| 2012/0244120 A1 | 9/2012 | Charron et al. |
| 2013/0012512 A1 | 1/2013 | Ito et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2013/0165462 A1 | 6/2013 | Singh et al. |
| 2014/0057915 A1 | 2/2014 | Cariou et al. |
| 2014/0114064 A1 | 4/2014 | Ito et al. |
| 2014/0213574 A1 | 7/2014 | Singh et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2014/0296271 A1 | 10/2014 | Fyfe |
| 2015/0166483 A1 | 6/2015 | Fyfe |
| 2015/0203475 A1 | 7/2015 | Duffy et al. |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0039797 A1 | 2/2016 | Fyfe |
| 2016/0045482 A1 | 2/2016 | Charron |
| 2016/0045512 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0130256 A1 | 5/2016 | King-Underwood et al. |
| 2016/0318958 A1 | 11/2016 | Fyfe et al. |
| 2016/0340343 A1 | 11/2016 | Fyfe et al. |
| 2016/0340375 A1 | 11/2016 | Fyfe et al. |
| 2016/0368896 A1 | 12/2016 | Longshaw et al. |
| 2016/0376232 A1 | 12/2016 | Thom |
| 2017/0007604 A1 | 1/2017 | Ito et al. |
| 2017/0057945 A1 | 3/2017 | Longshaw et al. |
| 2017/0182039 A1 | 6/2017 | Longshaw et al. |
| 2018/0044288 A1 | 2/2018 | Baker et al. |

FOREIGN PATENT DOCUMENTS

| | | |
|---|---|---|
| WO | WO 1999/32110 | 7/1999 |
| WO | WO 1999/32455 | 7/1999 |
| WO | WO 2000/43384 | 7/2000 |
| WO | WO 2001/04115 | 1/2001 |
| WO | WO 2001/36403 | 5/2001 |
| WO | WO 2001/64642 | 9/2001 |
| WO | WO 2002/092576 | 11/2002 |
| WO | WO 2003/005999 | 1/2003 |
| WO | WO 2003/068228 | 8/2003 |
| WO | WO 2003/068229 | 8/2003 |
| WO | WO 2003/072569 | 9/2003 |
| WO | WO 2005/048948 | 6/2005 |
| WO | WO 2005/110994 | 11/2005 |
| WO | WO 2006/072589 | 7/2006 |
| WO | WO 2007/053346 | 5/2007 |
| WO | WO 2009/117080 | 9/2009 |
| WO | WO 2009/158571 | 12/2009 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/072155 | 7/2010 |
| WO | WO 2010/075376 | 7/2010 |
| WO | WO 2010/075380 | 7/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/153553 | 12/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |

(56) References Cited

FOREIGN PATENT DOCUMENTS

| | | |
|---|---|---|
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 2014/162121 | 10/2014 |
| WO | WO 2014/162122 | 10/2014 |
| WO | WO 2014/162126 | 10/2014 |
| WO | WO 2015/121444 | 8/2015 |
| WO | WO 2015/121660 | 8/2015 |

OTHER PUBLICATIONS

Biancheri, et al. 2016 "Effect of narrow spectrum versus selective kinase inhibitors on the intestinal proinflammatory immune response in ulcerative colitis" *Inflamm Bowel Dis* 22(6): 1306-1315.
Boehm, et al. 2000 "New inhibitors of p38 kinase" *Expert Opinion on Therapeutic Patents* 10(1): 25-37.
Brinkmann, et al. 2010 "Fingolimod (FTY720): discovery and development of an oral drug to treat multiple sclerosis" *Nature Reviews* 9: 883-897.
CAS Registry No. 1379397-83-7, 2012 American Chemical Society.
CAS Registry No. 1379401-24-7, 2012 American Chemical Society.
CAS Registry No. 1379462-42-6, 2012 American Chemical Society.
CAS Registry No. 1379547-84-7, 2012 American Chemical Society.
CAS Registry No. 1379462-36-8, 2012 American Chemical Society.
CAS Registry No. 1384608-34-7, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Dodeller, et al. 2006 "The p38 mitogen-activated protein kinase signaling cascade in CD4 T cells" *Arthritis Research & Therapy* 8(2): 1-11.
Dumas; et al. 2004 "Recent developments in the discovery of protein kinase inhibitors from the urea class" *Current Opinion in Drug Discovery & Development* 7(5):600-616.
Jope, et al. 2007 "Glycogen synthase kinase-3 (GSK3): Inflammation, diseases, and therapeutics" *Neurochem Res* 32: 577-595.
Judge, et al. 2006 "Potassium channel blockers in multiple sclerosis: Neuronal $K_v$ channels and effects of symptomatic treatment" *Pharmacology & Therapeutics* 111: 224-259.
Kim, et al. 2009 "Src family kinases as mediators of endothelial permeability: effects on inflammation and metastasis" *Cell Tissue Res* 335: 249-259.
Kuster "Kinase inhibitors, Methods and Protocols" *Methods in Molecular Biology* 795 Chapters 1 and 2 (in 46 pages).
Lee, et al. 2005 "MAP kinase p38 inhibitors: Clinical results and an intimate look at their interactions with p38α protein" *Current Medicinal Chemistry* 12:2979-2994.
Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.
Masuda, et al. 2008 "Syk inhibitors as treatment for allergic rhinitis" *Pulmonary Pharmacology & Therapeutics* 21: 461-467.
McDermott, et al. 2009 "Personalized cancer therapy with selective kinase inhibitors: An emerging paradigm in medical oncology" *Journal of Clinical Oncology* 27(33): 5650-5659.
Onions, et al. 2016 "Discovery of narrow spectrum kinase inhibitors: new therapeutic agents for the treatment of COPD and steroid-resistant asthma" *Journal of Medicinal Chemistry* 59: 1727-1746.
Pargellis, et al. 2002 "Inhibition of p38 MAP kinase by utilizing a novel allosteric binding site" *Nature Structural Biology* 9(4):268-272.
Pettus, et al. 2008 "Small molecule p38 MAP kinase inhibitors for the treatment of inflammatory diseases: Novel structures and developments during 2006-2008" *Current Topics in Medicinal Chemistry* 8(16):1452-1467.
Sawyers 2008 "The cancer biomarker problem" *Nature* 452: 548-552.
Schreiber, et al. 2006 "Oral p38 mitogen-activated protein kinase inhibition with BIRB 796 for active Crohn's Diease: A randomized, double-blind, placebo-controlled trial" *Clinical Gastroenterology and Hepatology* 4:325-334.
Singh, et al. 2007 "Spleen tyrosine kinase (Syk) biology, inhibitors and therapeutic applications" *Annual Reports in Medicinal Chemistry* 42: 379-391.
Singh, et al. 2010 "A randomized, placebo-controlled study of the effects of the p38 MAPK inhibitor SB-681323 on blood biomarkers of inflammation in COPD patients" *J Clin Pharmacol* 50: 94-100.
Sutherland, et al. 2004 "Management of chronic obstructive pulmonary disease" *The New England Journal of Medicine* 350: 2689-2697.
To, et al. 2015 "Potent anti-inflammatory effects of the narrow spectrum kinase inhibitor RV1088 on rheumatoid arthritis synovial membrane cells" *British Journal of Pharmacology* 172: 3805-3816.
Weinblatt, et al. 2010 "An oral spleen tyrosine kinase (Syk) inhibitor for rheumatoid arthritis" *The New England Journal of Medicine* 363(14): 1303-1312.
Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide dihydrochloride (BAY 61-3606) blocks antigen-induced airway inflammation in rodents" *The Journal of Pharmacology and Experimental Therapeutics* 306(3): 1174-1181.
Traore, T. et al. 2013 "New aminopyrimidine derivatives as inhibitors of the TAM family" *European Journal of Medicinal Chemistry* 70: 789-801.

\* cited by examiner

KINASE INHIBITORS

FIELD OF THE INVENTION

The invention relates to compounds which are inhibitors of the family of p38 mitogen-activated protein kinase enzymes (referred to herein as p38 MAP kinase inhibitors), for example the alpha and gamma sub-types thereof, and of Syk kinase and the Src family of tyrosine kinases, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease, and of the eye, such as uveitis.

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively), each displaying different patterns of tissue expression, have been identified. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J Biol Chem.*, 2007, 282(48):34663-71), it may be involved in pain mechanisms through the regulation of COX2 expression (Fitzsimmons, B. L. et al., *Neuroreport*, 2010, 21(4):313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67). As these adverse effects vary with chemotype, and each of these compounds has distinct kinase selectivity patterns, the toxicities observed may be structure—rather than p38 mechanism-based.

Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+ T cells and in endothelial cells (Shmueli, O. et al., *Comptes Rendus Biologies*, 2003, 326(10-11):1067-1072; Smith, S. J. *Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the distribution of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072, (2003)/; Hale, K. K., *J. Immunol.*, 1999, 162(7):4246-52: Court, N. W. et al., *J. Mol. Cell. Cardiol.*, 2002, 34(4):413-26; Mertens, S. et al., *FEBS Lett.*, 1996, 383(3):273-6.)

Selective small molecule inhibitors of p38 MAPK gamma and p38 MAPK delta are not currently available, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y. *J. Biol. Chem.*, 2005, 280:19472-19479). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma, COPD (Chung, F., *Chest*, 2011, 139(6):1470-1479) and inflammatory bowel disease (IBD). There is now an abundant literature which demonstrates that p38 MAP kinase is activated by a range of pro-inflammatory cytokines and that its activation results in the recruitment and release of additional pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs.

The use of inhibitors of p38 MAP kinase in the treatment of COPD and IBD has also been proposed. Small molecule inhibitors targeted to p38 MAPK a/0 have proved to be effective in reducing various parameters of inflammation in:
 cells and tissues obtained from patients with COPD, who are generally corticosteroid insensitive, (Smith, S. J., *Br. J. Pharmacol.*, 2006, 149:393-404);
 biopsies from IBD patients (Docena, G. et al., *J. of Trans. Immunol.*, 2010, 162:108-115); and
 in vivo animal models (Underwood, D. C. et al., *Am. J. Physiol.*, 2000, 279:L895-902; Nath, P. et al., *Eur. J. Pharmacol.*, 2006, 544:160-167.).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.*, 2011, 80(6):1128-1135) demonstrates that silencing p38 MAPK gamma has the potential to restore sensitivity to corticosteroids. Consequently there may be a dual benefit for patients in the use of a p38 MAP kinase inhibitor for the treatment of COPD and severe asthma.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiologic investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., Papi, A., Psarras, S. and Johnston, S. L., *Paediatr. Respir. Rev.,* 2004, 5(3):255-260). A variety of additional studies support the conclusion that a viral infection can precipitate exacerbations and increase disease severity. For example, experimental clinical infections with rhinovirus have been reported to cause bronchial hyper-responsiveness to histamine in asthmatics which is unresponsive to treatment with corticosteroids (Grunberg, K., Sharon, R. F., et al., *Am. J. Respir. Crit. Care Med.,* 2001, 164(10):1816-1822). Further evidence derives from the association observed between disease exacerbations in patients with cystic fibrosis and HRV infections (Wat, D., Gelder, C., et al., *J. Cyst. Fibros.,* 2008, 7:320-328). Also consistent with this body of data is the finding that respiratory viral infections, including rhinovirus, represent an independent risk factor that correlates negatively with the 12 month survival rate in paediatric, lung transplant recipients (Liu, M., Worley, S., et al., *Transpl. Infect. Dis.,* 2009, 11(4):304-312).

Clinical research indicates that the viral load is proportionate to the observed symptoms and complications and, by implication, to the severity of inflammation. For example, following experimental rhinovirus infection, lower respiratory tract symptoms and bronchial hyper-responsiveness correlated significantly with virus load (Message, S. D., Laza-Stanca, V., et al., *PNAS,* 2008; 105(36):13562-13567). Similarly, in the absence of other viral agents, rhinovirus infections were commonly associated with lower respiratory tract infections and wheezing, when the viral load was high in immunocompetent paediatric patients (Gema, G., Piralla, A., et al., *J. Med. Virol.,* 2009, 81(8):1498-1507).

Interestingly, it has been reported recently that prior exposure to rhinovirus reduced the cytokine responses evoked by bacterial products in human alveolar macrophages (Oliver, B. G., Lim, S., et al., *Thorax,* 2008, 63:519-525). Additionally, infection of nasal epithelial cells with rhinovirus has been documented to promote the adhesion of bacteria, including *S. aureus* and *H. influenzae* (Wang, J. H., Kwon, H. J. and Yong, J. J., *The Laryngoscope,* 2009, 119(7):1406-1411). Such cellular effects may contribute to the increased probability of patients suffering a lower respiratory tract infection following an infection in the upper respiratory tract. Accordingly, it is therapeutically relevant to focus on the ability of novel interventions to decrease viral load in a variety of in vitro systems, as a surrogate predictor of their benefit in a clinical setting.

High risk groups, for whom a rhinovirus infection in the upper respiratory tract can lead to severe secondary complications, are not limited to patients with chronic respiratory disease. They include, for example, the immune compromised who are prone to lower respiratory tract infection, as well as patients undergoing chemotherapy, who face acute, life-threatening fever. It has also been suggested that other chronic diseases, such as diabetes, are associated with a compromised immuno-defence response. This increases both the likelihood of acquiring a respiratory tract infection and of being hospitalised as a result (Peleg, A. Y., Weerarathna, T., et al., *Diabetes Metab. Res. Rev.,* 2007, 23(1): 3-13; Kornum, J. B., Reimar, W., et al., *Diabetes Care,* 2008, 31(8):1541-1545).

Whilst upper respiratory tract viral infections are a cause of considerable morbidity and mortality in those patients with underlying disease or other risk factors; they also represent a significant healthcare burden in the general population and are a major cause of missed days at school and lost time in the workplace (Rollinger, J. M. and Schmidtke, M., *Med. Res. Rev.,* 2010, Doi 10.1002/med.20176). These considerations make it clear that novel medicines, that possess improved efficacy over current therapies, are urgently required to prevent and treat rhinovirus-mediated upper respiratory tract infections. In general the strategies adopted for the discovery of improved antiviral agents have targeted various proteins produced by the virus, as the point of therapeutic intervention. However, the wide range of rhinovirus serotypes makes this a particularly challenging approach to pursue and may explain why, at the present time, a medicine for the prophylaxis and treatment of rhinovirus infections has yet to be approved by any regulatory agency.

Viral entry into the host cell is associated with the activation of a number of intracellular signalling pathways controlled by the relative activation and inactivation of specific kinases which are believed to play a prominent role in the initiation of inflammatory processes (reviewed by Ludwig, S, 2007; Signal Transduction, 7:81-88) and of viral propagation and subsequent release.

It has been disclosed previously that compounds that inhibit the activity of both c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). For the reasons summarised above, in combination with the inhibition of p38 MAPKs, these are particularly advantageous inherent properties for compounds designed to treat chronic respiratory diseases.

Certain p38 MAPK inhibitors have also been described as inhibitors of the replication of respiratory syncytial virus (Cass, L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut,* 2002, 50:507-512, Docena, G. et al., *J. of Trans. Immunol.,* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Behçets patients (Chi W. et al. *Invest Ophthalmol Vis Sci.* 2008 49:3058-64). In support, Direskeneli and colleagues demonstrated that Behçets patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nature Reviews Cancer,* 2003, 3:155-168) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.,* 2009, 5(7):e1000446.). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology,* 2007, 8:34).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetectable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. The present invention therefore, inter alia, provides such novel compounds that inhibit the enzyme activity of p38 MAP kinase, for example with certain sub-type specificities, optionally together with Syk kinase and tyrosine kinases within the Src family (particularly c-Src) thereby possessing good anti-inflammatory properties, and suitable for use in therapy.

In one or more embodiments the compounds exhibit a long duration of action and/or persistence of action.

SUMMARY OF THE INVENTION

In a first aspect, the invention provides a compound of formula (I),

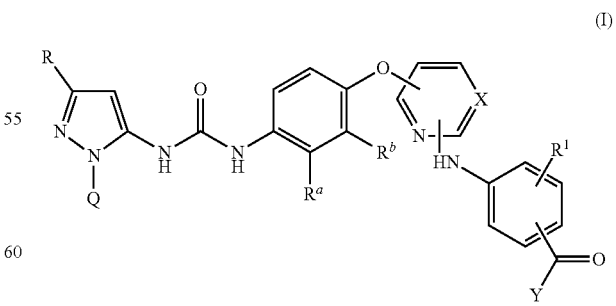

wherein:
Q represents thienyl, phenyl or pyridinyl, either of which may optionally bear 1 to 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $NH_2$, $N(H)$—$C_{1-6}$ alkyl, $N(C_{1-6}$ alkyl$)_2$, -L-P(O)R'R", $C_{1-6}$ alkylene-5-10 membered heterocycle and $C_{0-3}$ alkylene-O—$C_{0-6}$ alkylene-5-10 membered heterocycle;

L is a direct bond or $C_{1-2}$ alkylene;

R' represents $C_{1-4}$ alkyl;

R" represents $C_{1-4}$ alkyl, $C_{3-6}$ cycloalkyl, $C_{1-4}$ alkoxy or hydroxy;

or R' and R" together combine to form $C_{3-6}$ n-alkylene, wherein one $CH_2$ of said n-alkylene group is optionally replaced by O, N(H) or N($C_{1-4}$ alkyl);

X represents CH or N,

Y represents $NR^2R^3$;

R is
  $C_{1-6}$ alkyl,
  $C_{2-6}$ alkenyl,
  $C_{1-6}$ hydroxyalkyl,
  $C_{1-6}$ haloalkyl,
  $C_{1-6}$ alkyl substituted by $C_{2-3}$ alkynyl, $C_{1-3}$ alkoxy or cyano,
  $C_{0-2}$ alkylene-$C_{3-8}$ cycloalkyl optionally substituted with $C_{1-3}$ alkyl,
  a 4-5 membered heterocycle optionally substituted with $C_{1-3}$ alkyl or
  $Si(R^{1a})(R^{1b})(R^{1c})$;

$R^{1a}$ and $R^{1b}$ independently represent $C_{1-4}$ alkyl or $C_{3-6}$ cycloalkyl, or $R^{1a}$ and $R^{1b}$ together combine to form $C_{2-6}$ alkylene;

$R^{1c}$ represents $C_{1-2}$ alkyl;

$R^a$ and $R^b$, together with the C-atoms to which they are attached, form a fused phenyl ring that is optionally substituted by one or more substituents selected from $C_{1-3}$ alkyl, $C_{1-3}$ haloalkyl, cyano and halo, or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl or $R^a$ and $R^b$ together represent $C_{3-5}$ n-alkylene, which alkylene group is optionally substituted by one or more methyl substituents and/or which alkylene group optionally contains one C—C double bond between two C-atoms of the n-alkylene chain;

$R^1$ is selected from hydrogen, OH, halogen, CN, $C_{1-6}$ alkyl, $C_{2-6}$ alkenyl, $C_{2-6}$ alkynyl, $C_{1-6}$ haloalkyl, $C_{0-3}$ alkylene-$C_{3-6}$ cycloalkyl, $C_{0-3}$ alkylene-O—$C_{1-3}$ alkylene-$C_{3-6}$ cycloalkyl, $C_{1-6}$ alkoxy, $C_{1-6}$ haloalkoxy, $C_{1-6}$ hydroxyalkyl, $C_{0-3}$ alkylene-$SO_2C_{1-3}$alkyl, $C_{0-3}$ alkylene-$SO_2NR^4R^5$, and $C_{0-3}$ alkylene-$NR^6R^7$ and $C_{0-3}$ alkylene-$NCOR^6R^7$;

one of $R^2$ and $R^3$ represents —[$C_{2-4}$ alkylene-O]$_{1-12}$—[$C_{2-4}$ alkylene]-$R^{2a}$ and the other of $R^2$ and $R^3$ is selected from H, $C_{1-8}$ alkyl, $C_{0-6}$ alkylene aryl, $C_{0-6}$ alkylene heteroaryl, —[$C_{2-4}$ alkylene-O]$_{0-12}$—[$C_{2-4}$ alkylene]-$R^{2a}$, $C_{0-6}$ alkylene-4-10 membered heterocycle, and $C_{0-3}$ alkylene-O—$C_{0-6}$ alkylene-4-10 membered heterocycle with the proviso that when the said heterocycle is linked through nitrogen there are at least two C-atoms in the alkylene chain that links that nitrogen atom to the essential O atom of the substituent, wherein independently each alkyl or alkylene group optionally bears 1 oxo substituent, and optionally one or two carbon atoms in the alkyl or alkylene chain may each be replaced by a heteroatom selected from O, N or $S(O)_p$, such that when said alkyl or alkylene comprises an amine said amino group is a tertiary amine, wherein each 4-10 membered heterocycle is optionally substituted by 1 or 2 groups independently selected from halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$C_{0-3}$ alkylene aryl, $C_{0-6}$ alkylene heteroaryl, $C_{0-3}$ alkylene-O—$C_{0-3}$ alkylene heteroaryl, $C(O)C_{1-6}$ alkyl, $SO_2NR^8R^9$, and $C_{0-3}$ alkylene-$NR^8R^9$, $C_{0-3}$ alkylene-$NR^8SO_2R^9$ and $C_{0-3}$ alkylene-$NR^8C(O)R^9$;

$R^{2a}$ represents $OR^{2b}$ or $N(R^{2c})R^{2d}$;

$R^{2b}$ to $R^{2d}$ independently represent H or $C_{1-4}$ alkyl optionally substituted by one or more halo atoms, or $R^{2c}$ and $R^{2d}$ together represent
  $C_{3-6}$ n-alkylene,
  $C_{4-5}$ n-alkylene interrupted between C2 and C3 by —O— or —N($R^{2e}$)— or
  $C_6$ n-alkylene interrupted between C2 and C3, or between C3 and C4, by —O— or —N($R^{2e}$)—,
any of which n-alkylene groups are optionally substituted by one or more substituents selected from halo, hydroxy, oxo, $C_{1-4}$ alkyl and $C_{1-4}$ alkoxy;

$R^{2c}$ represents H or $C_{1-6}$ alkyl optionally substituted by one or more substituents selected from halo and hydroxy;

$R^4$ is H or $C_{1-4}$ alkyl;

$R^5$ is H or $C_{1-4}$ alkyl, $R^6$ is H or $C_{1-4}$ alkyl, $C(O)C_{1-3}$alkyl and $SO_2C_{1-3}$ alkyl;

$R^7$ is H or $C_{1-4}$ alkyl, $C(O)C_{1-3}$alkyl and $SO_2C_{1-3}$ alkyl;

$R^8$ is H or $C_{1-4}$ alkyl, and $R^9$ is H or $C_{1-4}$ alkyl, p is 0, 1 or 2 or a pharmaceutically acceptable salt thereof, including all stereoisomers and tautomers thereof.

Compounds of the invention are inhibitors of p38 MAP kinase especially of the alpha sub-type.

In at least some embodiments compounds of the present invention have low B-Raf binding, for example less than 40% inhibition of the kinase binding at 500 nM, such as 30% inhibition or less in an assay such as the Kinomescan method.

B-Raf is a member of the Raf kinase family of serine/threonine-specific protein kinases. This protein plays a role in regulating the MAP kinase/ERKs signalling pathway, which affects cell division, differentiation, and secretion. A mutation of the gene has been associated with cancer in humans (Davies, H. et al., *Nature*, 2002, 417(6892):949-54).

Cell signalling can bypass selective inhibition of B-Raf with undesirable consequences (Lo, R. S., *Cell Research*, advance online publication 8 May 2012; doi: 10.1038/cr.2012.78). It is therefore preferable that kinase inhibitors intended for use as anti-inflammatory medicines should have minimal potential to interact with B-Raf.

The present compounds also display low affinity for GSK3α kinase in binding assays, which is considered to be beneficial in a therapeutic context, in particular in relation to minimising toxicity in vivo.

In at least some embodiments, compounds of the present invention have p59-HCK inhibitory activity which may also augment their advantageous therapeutic profile.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the or an oxygen atom (e.g. a single oxygen atom) is located within the alkyl chain, for example —$C_{1-3}$ alky-l$OC_{1-3}$ alkyl, such as —$CH_2CH_2OCH_3$ or —$CH_2OCH_3$. Thus in one embodiment the alkoxy is linked through carbon to the remainder of the molecule, for example —C$_{6-n}$alkyl-O—C$_{6-m}$alkyl in which n=1-5, m=1-5 and n+m=6-10. In one embodiment the alkoxy is linked through oxygen to the remainder of the molecule, for example —OC$_{1-6}$ alkyl. In one embodiment the disclosure relates to straight chain alkoxy. In one embodiment the alkoxy is linked through oxygen to the remainder of the molecule but the alkoxy group contains a further oxygen atom, for example —OCH$_2$CH$_2$OCH$_3$.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, in particular perfluoroalkyl, more specifically —CF$_2$CF$_3$ or CF$_3$.

Alkyl substituted by hydroxy (hydroxyalkyl) as employed herein refers to alkyl groups having 1 to 3 hydroxy groups, for example 1 or 2 hydroxy substituents thereon, for example —CH$_2$CH$_2$OH, —C(CH$_3$)CH$_2$OH, —C(CH$_3$)$_2$CH$_2$OH or similar.

Alkoxy substituted by halo (haloalkoxy) as employed herein refers to alkoxy groups having 1 to 6 halogen atoms, for example 1 to 5 halogens, such as per haloalkoxy, in particular perfluoroalkoxy, more specifically —OCF$_2$CF$_3$ or —OCF$_3$.

Unless otherwise specified, alkylene as employed herein is a straight chain or branched chain carbon linking group, for example comprising methylenes, between two other moieties. It will be clear to those skilled in the art that groups defined as, for example C$_{2-8}$ alkenyl and C$_{2-8}$ alkynyl may comprise an alkylene portion. For the avoidance of doubt, the term "n-alkylene", when used herein, refers to straight chain alkylene.

It will be clear to persons skilled in the art that the heteroatom may replace a primary, secondary or tertiary carbon, that is a CH$_3$, —CH$_2$— or a —CH—, group, as technically appropriate and hydrogen or branching in the alkyl or alkylene chain will fill the valency of the heteroatom as appropriate to the location, for example where a terminal primary carbon is replaced by an oxygen heteroatom the terminal group will be an alcohol.

C$_{1-6}$ alkyl includes C$_1$, C$_2$, C$_3$, C$_4$, C$_5$ and C$_6$.
C$_{1-6}$ alkoxy includes C$_1$, C$_2$, C$_3$, C$_4$, C$_5$ and C$_6$.

The term 5-10 membered heterocycle, as employed herein, refers to a 5 to 10 membered saturated or partially unsaturated non-aromatic ring comprising one or more, for example 1, 2, 3 or 4 heteroatoms independently selected from O, N and S, wherein optionally one or two carbons in the ring may bear an oxo substituent. Any valencies of a heteroatom not employed in forming or retaining the ring structure may be filled by hydrogen or a substituent, as appropriate. Thus the optional substituents on the heterocycles may be attached to a carbon or on a heteroatom, such as nitrogen as appropriate. Examples of 5-10 membered heterocycles include, pyrroline, pyrrolidine, tetrahydrofuran, thiepane, oxepane piperidine, piperazine, morpholine, thiomorpholine, dioxane, tetrahydrothiophene, pyrazoline, imidazoline, pyrazolidine, oxoimidazolidine, dioxolane, thiazolidine, isoxazolidine, dihydropyran, dihydroindene, dihydroisobenzofuran, isoindolin-1-one, chroman, 1,2,3,4-tetrahydroquinoline, 2,3-dihydrobenzo[b][1,4]dioxineazocane, and the like.

The term 5-6 membered heterocycle as employed herein refers to a 5 to 6 membered saturated or partially unsaturated non-aromatic ring comprising one or more, for example 1, 2, 3 or 4 heteroatoms independently selected from O, N and S wherein optionally one or two carbons in the ring may bear an oxo substituent. The definition of C$_{5-6}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substituent. Clearly any valencies of a heteroatom not employed in forming or retaining the ring structure may be filled by hydrogen or a substituent, as appropriate. Thus substituents on heterocycles may be on carbon or on a heteroatom, such as N as appropriate. Examples of heterocycles and C$_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

When employed herein, the group morpholinyl suitably represents N-morpholinyl.

In one embodiment there is provided a compound of formula (Ia1) or, particularly, formula (Ia2):

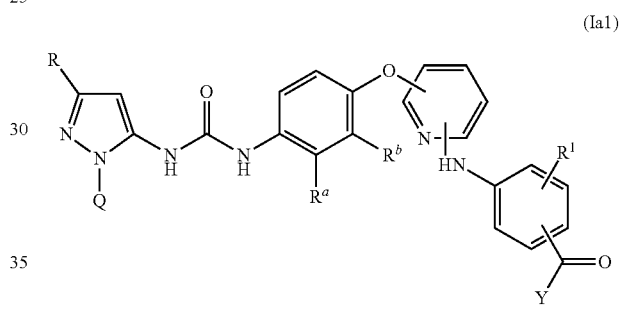

(Ia1)

(Ia2)

wherein R, R$^a$, R$^b$, R$^1$, Q and Y are defined as above for compounds of formula (I).

In one embodiment there is provided a compound of formula (Ib1) or, particularly, formula (Ib2):

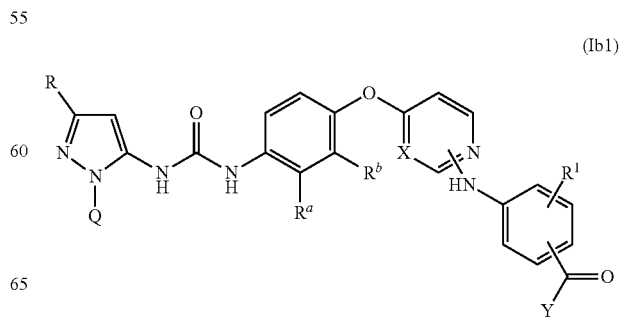

(Ib1)

-continued

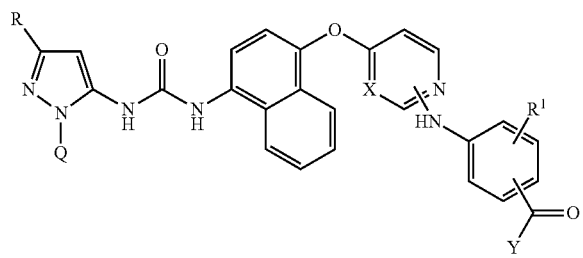
(Ib2)

wherein R, $R^a$, $R^b$, $R^1$, Q, X and Y are defined above for compounds of formula (I)

In one embodiment there is provided a compound of formula (Ic1) or, particularly, formula (Ic2):

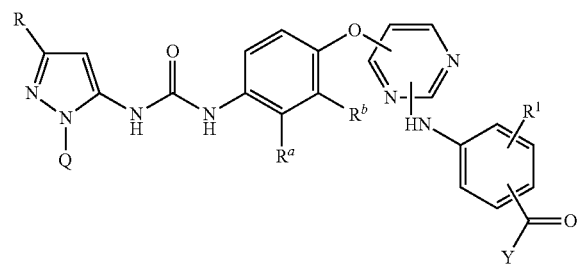
(Ic1)

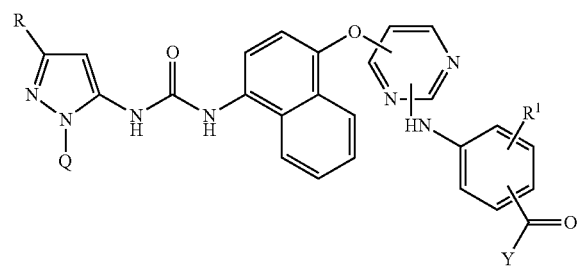
(Ic2)

wherein R, $R^a$, $R^b$, $R^1$, Q and Y are defined above for compounds of formula (I).

In one embodiment there is provided a compound of formula (Id1) or, particularly, formula (Id2):

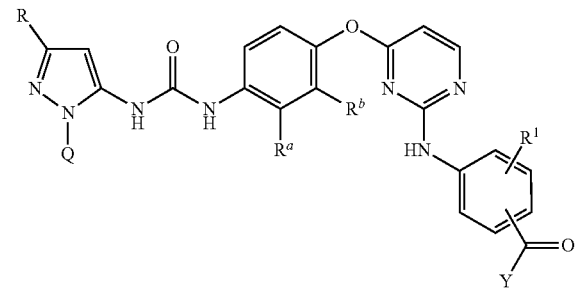
(Id1)

-continued

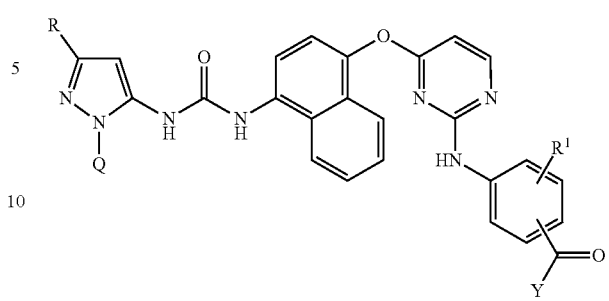
(Id2)

wherein R, $R^a$, $R^b$, $R^1$, Q and Y are defined above for compounds of formula (I).

In one embodiment there is provided a compound of formula (Ie1) or, particularly, formula (Ie2):

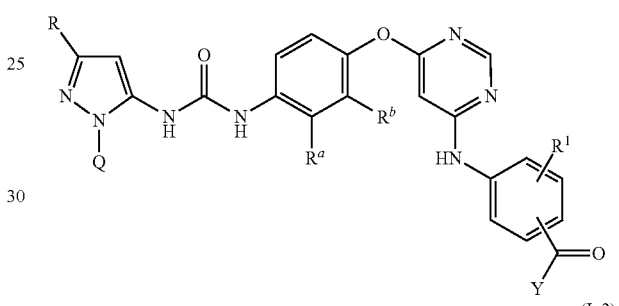
(Ie1)

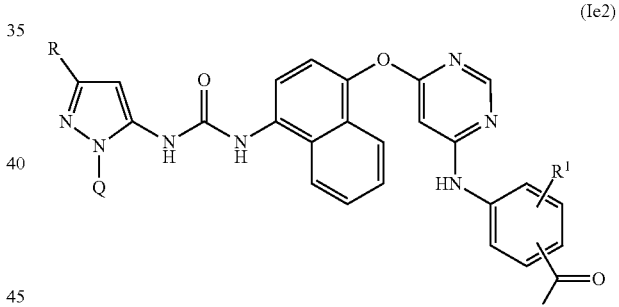
(Ie2)

wherein R, $R^a$, $R^b$, $R^1$, Q and Y are defined above for compounds of formula (I).

In one embodiment there is provided a compound of formula (If1) or, particularly, formula (If2):

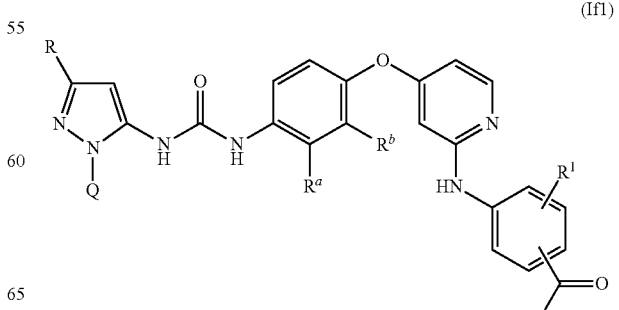
(If1)

-continued

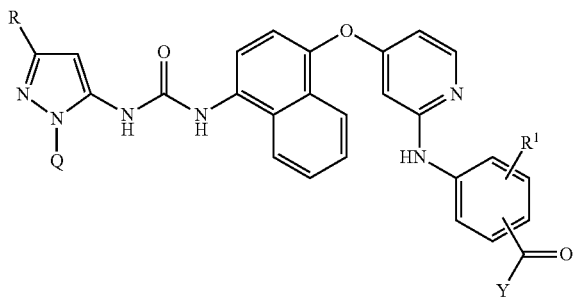

(If2)

wherein R, $R^a$, $R^b$, $R^1$, Q and Y are defined above for compounds of formula (I).

In one embodiment there is provided a compound of formula (Ig1) or, particularly, formula (Ig2):

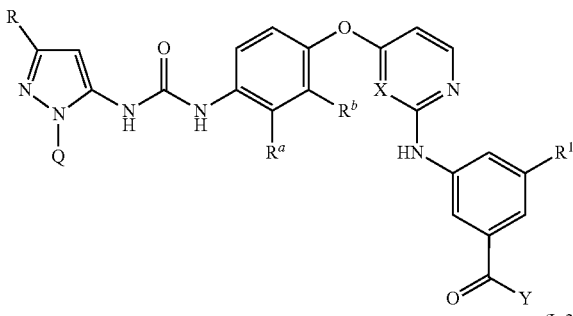

(Ig1)

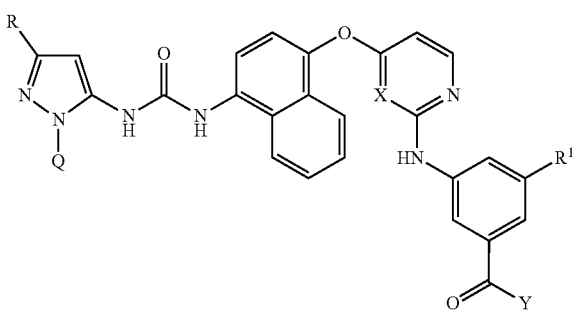

(Ig2)

wherein R, $R^a$, $R^b$, $R^1$, X, Q and Y are as defined above for compounds of formula (I).

In one embodiment there is provided a compound of formula (Ih1) or, particularly, formula (Ih2):

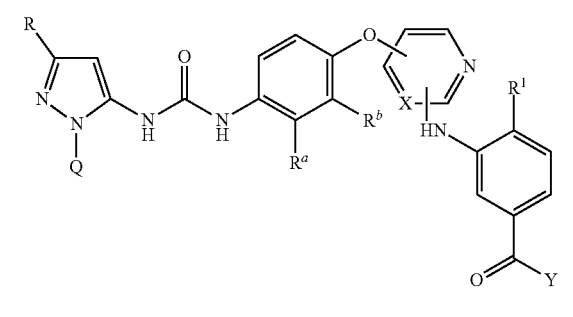

(Ih1)

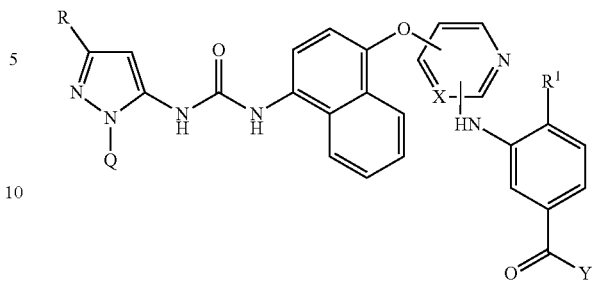

(Ih2)

wherein R, $R^a$, $R^b$, $R^1$, X, Q and Y are as defined above for compounds of formula (I).

Generally in substituents such $C_{0-3}$ alkylene-O—$C_{0-6}$ alkylene-5-10 membered heterocycle, for example as defined for $R^2$ or $R^3$, when the said heterocycle is linked through nitrogen the group will then be defined as $C_{0-3}$ alkylene-O—$C_{2-6}$ alkylene-5-10 membered heterocycle.

Generally when Q comprises a phenyl or pyridine substituted with a $C_{1-6}$ alkylene-5-10 membered heterocycle or $C_{0-3}$ alkylene-O—$C_{0-6}$ alkylene-5-10 membered heterocycle then $R^2$ and $R^3$ are independently selected from H, $C_{1-8}$ alkyl, wherein independently each alkyl or alkylene group optionally bears 1 oxo substituent, and optionally up to two carbon atoms in the alkyl or alkylene chain may be replaced by a heteroatom selected from O, N or $S(O)_p$, such that when alkyl or alkylene comprises an amine said amino group is a tertiary amine.

In one embodiment Q represents phenyl bearing one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, $N(C_{1-6}$ alkyl$)_2$, $C_{1-6}$ alkylene-5-10 membered heterocycle and $C_{0-3}$ alkylene-O—$C_{1-6}$ alkylene-5-10 membered heterocycle (e.g. one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle).

In one embodiment Q represents phenyl bearing a methyl, methoxy, —$N(CH_3)_2$ or —$OCH_2CH_2OCH_3$ (e.g. methyl, methoxy, or —$OCH_2CH_2OCH_3$), for example one of said substituents, in particular in the para position.

In one embodiment Q is dimethyl phenyl, for example where the methyl substituents are in the mew and para position.

In one embodiment Q represents pyridinyl bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

In one embodiment Q is methoxypyridinyl, for example 6-methoxypyridin-3-yl.

In one embodiment Q represents thienyl optionally bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

In one embodiment R is ethyl, isopropyl, tert-butyl, cyclopropyl, 1-methylcyclopropyl, propen-2-yl, $CF_3$, $C_2F_5$, oxetanyl, (methyl)oxetanyl or tetrahydrofuranyl (e.g. ethyl, isopropyl, tert-butyl, cyclopropyl, 1-methylcyclopropyl, CF$_3$, C$_2$F$_5$, oxetanyl, (methyl)oxetanyl or tetrahydrofuranyl), such as isopropyl or tert-butyl.

In one embodiment R is C(CH$_3$)$_2$CH$_2$OH or CH(CH$_3$)CH$_2$OH.

In one embodiment R is 1-hydroxy-2-methylpropan-2-yl.

In one embodiment R$^1$ is H, Br, Cl, CH$_3$, CH$_2$CH$_3$, CN, N(CH$_3$)$_2$, CF$_3$, ethynyl, OCH$_3$, OCHF$_2$, OCH$_2$CH$_3$ or OCH$_2$(CH$_3$)$_2$ (e.g. R$^1$ is H, Br, Cl, CH$_3$, CN, N(CH$_3$)$_2$, CF$_3$, ethynyl, OCH$_3$, OCH$_2$CH$_3$ or OCH$_2$(CH$_3$)$_2$).

In one embodiment R$^4$ is H or methyl.
In one embodiment R$^5$ is H or methyl.
In one embodiment R$^6$ is H or methyl.
In one embodiment R$^7$ is H or methyl.
In one embodiment R$^8$ is H or methyl.
In one embodiment R$^9$ is H or methyl.

Embodiments of the invention that may be mentioned include compounds of formulae (I), (Ia1), (Ia2), (Ib1), (Ib2), (Ic1), (Ic2), (Id1), (Id2), (Ie1), (Ie2), (If1), (If2), (Ig1), (Ig2), (Ih1) and (Ih2) wherein:

Q represents phenyl substituted by -L-P(O)R'R" or, particularly, phenyl bearing one or two substituents independently selected from hydroxyl, halogen, C$_{1-6}$ alkyl, C$_{1-6}$ alkoxy, C$_{1-6}$ haloalkoxy, C$_{1-6}$ hydroxyalkyl, N(C$_{1-6}$ alkyl)$_2$, C$_{1-6}$ alkylene-5-10 membered heterocycle and C$_{0-3}$ alkylene-O—C$_{1-6}$ alkylene-5-10 membered heterocycle (e.g. Q represents phenyl mono-substituted (e.g. in the para position) by methyl, methoxy, —N(CH$_3$)$_2$ or —OCH$_2$CH$_2$OCH$_3$ or di-substituted (e.g. in the mew and para positions) by methyl), or Q represents pyridinyl bearing one substituent independently selected from hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle and C$_{0-3}$ alkylene-O—C$_{1-6}$ alkylene-5-10 membered heterocycle (e.g. Q represents methoxypyridinyl, such as 6-methoxypyridin-3-yl);

L is CH$_2$;

R' and R" both represent C$_{1-4}$ alkyl (e.g. C$_{1-2}$ alkyl, such as methyl);

R$^a$ and R$^b$ together represent —(CH$_2$)$_{3-5}$— or, particularly, R$^a$ and R$^b$, together with the C-atoms to which they are attached, form a fused phenyl ring, or one of R$^a$ and R$^b$ represents halo, C$_{1-3}$ alkyl or C$_{1-3}$ haloalkyl and the other independently represents halo, cyano, C$_{1-3}$ alkyl or C$_{1-3}$ haloalkyl (e.g. R$^a$ and R$^b$ both represent methyl, fluoro or chloro);

Y represents NR$^2$R$^3$;

R$^2$ represents —[C$_{2-4}$ alkylene-O]$_{1-6}$—[C$_{2-4}$ alkylene]-R$^{2a}$ (e.g. —[C$_{2-4}$ alkylene-O]$_{1-3}$—[C$_{2-4}$ alkylene]-R$^{2a}$, such as —[CH$_2$CH$_2$O]$_{1-2}$—CH$_2$CH$_2$R$^{2a}$);

R$^3$ represents methyl or, particularly, H;

R$^{2a}$ represents OR$^{2b}$ or N(R$^{2c}$)R$^{2d}$;

R$^{2b}$ represents H or C$_{1-4}$ alkyl (e.g. R$^{2b}$ represents methyl);

R$^{2c}$ and R$^{2d}$ independently represent H or C$_{1-4}$ alkyl (e.g. methyl) or R$^{2c}$ and R$^{2d}$ together represent C$_{4-5}$ n-alkylene, which n-alkylene group is optionally interrupted between C2 and C3 by —O— or —N(R$^{2e}$)— (e.g. R$^{2c}$ and R$^{2d}$ either both represent methyl or together represent —CH$_2$CH$_2$—O—CH$_2$CH$_2$—, —CH$_2$CH$_2$—NH—CH$_2$CH$_2$— or —CH$_2$CH$_2$—N(CH$_3$)—CH$_2$CH$_2$—);

R$^{2e}$ represents H or C$_{1-4}$ alkyl (e.g. methyl);

R represents
Si(C$_{1-2}$ alkyl)$_3$ (e.g. Si(CH$_3$)$_3$),
—C(C$_{1-2}$ alkyl)$_2$-C$_{2-3}$ alkynyl (e.g. —C(CH$_3$)$_2$—C≡C—H) or, particularly,
C$_{1-6}$ alkyl optionally substituted by hydroxy, cyano or methoxy or by one or more fluoro groups,
C$_{2-6}$ alkenyl or C$_{3-4}$ cycloalkyl, which latter group is optionally substituted by C$_{1-3}$ alkyl
(e.g. R represents ethyl, isopropyl, n-propyl, tert-butyl, cyclopropyl, 1-methylcyclopropyl, CF$_3$, C$_2$F$_5$, —C(CH$_3$)$_2$CF$_3$ oxetanyl, (methyl)oxetanyl, tetrahydrofuranyl or propen-2-yl, such as isopropyl, propen-2-yl or tert-butyl); and/or R$^1$ represents H, halogen (e.g. F, Br or Cl), CN, C$_{1-4}$ alkyl (e.g. methyl or ethyl), C$_{2-4}$ alkynyl (e.g. ethynyl), C$_{1-4}$ fluoroalkyl (e.g. CF$_3$), C$_{1-4}$ alkoxy (e.g. OCH$_3$, OCH$_2$CH$_3$ or OCH$_2$(CH$_3$)$_2$), C$_{1-4}$ haloalkoxy (e.g. OCHF$_2$) or NR$^6$R$^7$ (e.g. N(CH$_3$)$_2$) (e.g. R$^1$ represents H, halogen (e.g. F, Br or Cl), CN, C$_{1-4}$ alkyl (e.g. methyl or ethyl), C$_{2-4}$ alkynyl (e.g. ethynyl), C$_{1-4}$ fluoroalkyl (e.g. CF$_3$), C$_{1-4}$ alkoxy (e.g. OCH$_3$, OCH$_2$CH$_3$ or OCH$_2$(CH$_3$)$_2$), or NR$^6$R$^7$ (e.g. N(CH$_3$)$_2$), in particular R$^1$ represents ethynyl or OCH$_3$).

More particular embodiments of the invention that may be mentioned include compounds of formulae (I), (Ia1), (Ia2), (Ib1), (Ib2), (Ic1), (Ic2), (Id1), (Id2), (Ie1), (Ie2), (If1), (If2), (Ig1), (Ig2), (Ih1) and (Ih2) wherein:

Q represents phenyl mono-substituted (e.g. in the mew position) by —CH$_2$—P(O)(C$_{1-2}$ alkyl)$_2$ or, particularly, phenyl mono-substituted (e.g. in the para position) by C$_{1-6}$ alkyl (e.g. methyl), C$_{1-6}$ alkoxy (e.g. methoxy), C$_{1-6}$ haloalkoxy or N(C$_{1-6}$ alkyl)$_2$ (e.g. N(CH$_3$)$_2$) (for example, Q represents phenyl substituted in the para position by methyl, methoxy or dimethylamino);

R$^a$ and R$^b$ together represent —(CH$_2$)$_4$— or, particularly, R$^a$ and R$^b$, together with the C-atoms to which they are attached, form a fused phenyl ring;

Y represents NR$^2$R$^3$;

R$^2$ represents —[C$_{2-3}$ alkylene-O]$_{1-3}$—[C$_{2-3}$ alkylene]-R$^{2a}$ (e.g. R$^2$ represents —[CH$_2$CH$_2$O]$_{1-2}$—CH$_2$CH$_2$R$^{2a}$);

R$^3$ represents H;

R$^{2a}$ represents —O—(C$_{1-3}$ alkyl) (e.g. —OCH$_3$) or N(R$^{2c}$)R$^{2d}$;

R$^{2c}$ and R$^{2d}$ independently represent H or C$_{1-3}$ alkyl (e.g. methyl) or R$^{2c}$ and R$^{2d}$ together represent C$_4$ n-alkylene, which n-alkylene group is optionally interrupted between C2 and C3 by —O— or —N(R$^{2e}$)— (e.g. R$^{2c}$ and R$^{2d}$ either both represent methyl or together represent —CH$_2$CH$_2$—N(CH$_3$)—CH$_2$CH$_2$— or, particularly, —CH$_2$CH$_2$—O—CH$_2$CH$_2$—);

R represents C$_{1-4}$ alkyl optionally substituted by one or more fluoro groups, C$_{3-4}$ alkenyl or C$_{3-4}$ cycloalkyl, which latter group is optionally substituted by methyl (e.g. R represents ethyl, cyclopropyl, CF$_3$, C$_2$F$_5$, —C(CH$_3$)$_2$CF$_3$ or, particularly, isopropyl, 1-methylcyclopropyl, propen-2-yl or tert-butyl); and/or R$^1$ represents Br, Cl, CN, methyl, ethyl, CF$_3$, OCHF$_2$, OCH$_2$CH$_3$, OCH$_2$(CH$_3$)$_2$, N(CH$_3$)$_2$ or, particularly, ethynyl or OCH$_3$ (e.g. R$^1$ represents Br, Cl, CN, methyl, ethyl, CF$_3$, OCH$_2$CH$_3$, OCH$_2$(CH$_3$)$_2$, N(CH$_3$)$_2$ or, particularly, ethynyl or OCH$_3$).

Particular embodiments of the invention include the following.

(1) A compound of formula (I), (Ia1), (Ia2), (Ib1), (Ib2), (Ic1), (Ic2), (Id1), (Id2), (Ie1), (Ie2), (If1), (If2), (Ig1), (Ig2), (Ih1) or (Ih2) as defined above, or a pharmaceutically acceptable salt thereof.

(2) A compound or salt according to Embodiment (1), wherein Q represents phenyl bearing one or two substituents independently selected from hydroxyl, halogen, C$_{1-6}$ alkyl, C$_{1-6}$ alkoxy, C$_{1-6}$ haloalkoxy, C$_{1-6}$ hydroxyalkyl, N(C$_{1-6}$ alkyl)$_2$, C$_{1-6}$ alkylene-5-10 membered heterocycle and C$_{0-3}$ alkylene-O—C$_{1-6}$ alkylene-5-10 membered heterocycle (e.g. one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle).

(3) A compound or salt according to Embodiment (1) or Embodiment (2), wherein Q represents phenyl bearing a methyl, methoxy, —N(CH$_3$)$_2$ or —OCH$_2$CH$_2$OCH$_3$ (e.g. a methyl, methoxy or —OCH$_2$CH$_2$OCH$_3$).

(4) A compound or salt according to any one of Embodiments (1) to (3), wherein Q represents phenyl substituted in the para position by methyl, methoxy, —N(CH$_3$)$_2$ or —OCH$_2$CH$_2$OCH$_3$ (e.g. by methyl, methoxy or —OCH$_2$CH$_2$OCH$_3$).

(5) A compound or salt according to any one of Embodiments (1) to (3), wherein Q is dimethyl phenyl, for example where the methyl substituents are in the mew and para position.

(7) A compound or salt according to Embodiment (1), wherein Q represents pyridinyl bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

(8) A compound or salt according to Embodiment (7), wherein Q is methoxypyridinyl, for example 6-methoxypyridin-3-yl.

(9) A compound or salt according to Embodiment (1), wherein Q represents thienyl optionally bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

(10) A compound or salt according to any one of Embodiments (1) to (9), wherein R is ethyl, isopropyl, tert-butyl, cyclopropyl, 1-methylcyclopropyl, CF$_3$, C$_2$F$_5$, oxetanyl, (methyl)oxetanyl or tetrahydrofuranyl, such as isopropyl or tert-butyl.

(11) A compound or salt according to any one of Embodiments (1) to (9), wherein R is C(CH$_3$)$_2$CH$_2$OH or CH(CH$_3$)CH$_2$OH.

(12) A compound or salt according to any one of Embodiments (1) to (9), wherein R is 1-hydroxy-2-methylpropan-2-yl.

(13) A compound or salt according to any one of Embodiments (1) to (12), wherein $R^1$ is H, Br, Cl, CH$_3$, CH$_2$CH$_3$, CN, N(CH$_3$)$_2$, CF$_3$, ethynyl, OCH$_3$, OCHF$_2$, OCH$_2$CH$_3$ or OCH$_2$(CH$_3$)$_2$ (e.g. $R^1$ is H, Br, Cl, CH$_3$, CN, N(CH$_3$)$_2$, CF$_3$, ethynyl, OCH$_3$, OCH$_2$CH$_3$ or OCH$_2$(CH$_3$)$_2$).

(14) A compound or salt according to any one of Embodiments (1) to (13), wherein $R^4$ is H or methyl.

(15) A compound or salt according to any one of Embodiments (1) to (14), wherein $R^5$ is H or methyl.

(16) A compound or salt according to any one of Embodiments (1) to (15), wherein $R^6$ is H or methyl.

(17) A compound or salt according to any one of Embodiments (1) to (16), wherein $R^7$ is H or methyl.

(18) A compound or salt according to any one of Embodiments (1) to (17), wherein $R^8$ is H or methyl.

(19) A compound or salt according to any one of Embodiments (1) to (18), wherein $R^9$ is H or methyl.

(20) A compound or salt according to any one of Embodiments (1) and (10) to (19), wherein Q represents phenyl mono-substituted (e.g. in the para position) by $C_{1-6}$ alkyl (e.g. methyl), $C_{1-6}$ alkoxy (e.g. methoxy), $C_{1-6}$ haloalkoxy or N($C_{1-6}$ alkyl)$_2$ (e.g. N(CH$_3$)$_2$).

(21) A compound or salt according to Embodiment (20), wherein Q represents phenyl substituted in the para position by methyl, methoxy or dimethylamino

(22) A compound or salt according to any one of Embodiments (1) to (21), wherein $R^a$ and $R^b$, together with the C-atoms to which they are attached, form a fused phenyl ring.

(23) A compound or salt according to any one of Embodiments (1) to (22) (e.g. any one of Embodiments (1) to (21)), wherein $R^2$ represents —[$C_{2-3}$ alkylene-O]$_{1-3}$—[$C_{2-3}$ alkylene]-$R^{2a}$ (e.g. $R^2$ represents —[CH$_2$CH$_2$O]$_{1-2}$—CH$_2$CH$_2$R$^{2a}$).

(24) A compound or salt according to any one of Embodiments (1) to (23), wherein $R^3$ represents H.

(25) A compound or salt according to any one of Embodiments (1) to (24), wherein $R^{2a}$ represents —O—($C_{1-3}$ alkyl) (e.g. —OCH$_3$) or N($R^{2c}$)$R^{2d}$.

(26) A compound or salt according to any one of Embodiments (1) to (25), wherein $R^{2c}$ and $R^{2d}$ independently represent H or $C_{1-3}$ alkyl (e.g. methyl) or $R^{2c}$ and $R^{2d}$ together represent C$_4$ n-alkylene, which n-alkylene group is optionally interrupted between C2 and C3 by —O— or —N($R^{2e}$)— (e.g. $R^{2c}$ and $R^{2d}$ either both represent methyl or together represent —CH$_2$CH$_2$—N(CH$_3$)—CH$_2$CH$_2$— or, particularly, —CH$_2$CH$_2$—O—CH$_2$CH$_2$—).

(27) A compound or salt according to any one of Embodiments (1) to (9) and (13) to (26), wherein R represents $C_{1-4}$ alkyl optionally substituted by one or more fluoro groups, $C_{3-4}$ alkenyl or $C_{3-4}$ cycloalkyl, which latter group is optionally substituted by methyl (e.g. R represents ethyl, cyclopropyl, CF$_3$, C$_2$F$_5$, —C(CH$_3$)$_2$CF$_3$ or, particularly, isopropyl, 1-methylcyclopropyl, propen-2-yl or ten-butyl).

(28) A compound or salt according to any one of Embodiments (1) to (12) and (14) to (27), wherein $R^1$ represents Br, Cl, CN, methyl, ethyl, CF$_3$, OCHF$_2$, OCH$_2$CH$_3$, OCH$_2$(CH$_3$)$_2$, N(CH$_3$)$_2$, ethynyl or OCH$_3$ (e.g. $R^1$ represents Br, Cl, CN, methyl, ethyl, CF$_3$, OCH$_2$CH$_3$, OCH$_2$(CH$_3$)$_2$, N(CH$_3$)$_2$, ethynyl or OCH$_3$).

(29) A compound or salt according to Embodiment (28), wherein $R^1$ represents ethynyl or OCH$_3$.

(30) A compound or salt according to any one of Embodiments (1) to (29) above, wherein:
Q represents thienyl, phenyl or pyridinyl, either of which is substituted by NH$_2$, N(H)—$C_{1-6}$ alkyl, N($C_{1-6}$ alkyl)$_2$ or, particularly, -L-P(O)R'R" and is optionally further substituted by 1 or 2 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, NH$_2$, N(H)—$C_{1-6}$ alkyl, N($C_{1-6}$ alkyl)$_2$, -L-P(O)R'R", $C_{1-6}$ alkylene-5-10 membered heterocycle and $C_{0-3}$ alkylene-O—$C_{0-6}$ alkylene-5-10 membered heterocycle;
R represents $C_{2-6}$ alkenyl (e.g. $C_{3-4}$ alkenyl, such as propen-2-yl), $C_{1-6}$ alkyl substituted by $C_{1-3}$ alkoxy or cyano (e.g. secondary $C_{3-6}$ alkyl substituted by methoxy or cyano, such as —C(CH$_3$)$_2$OCH$_3$ or —C(CH$_3$)$_2$CN) or, particularly, $C_{1-6}$ alkyl substituted by $C_{2-3}$ alkynyl (e.g. —C($C_{1-2}$ alkyl)$_2$-$C_{2-3}$ alkynyl, such as —C(CH$_3$)$_2$—C≡C—H) or Si($R^{1a}$)($R^{1b}$)($R^{1c}$) (e.g. Si($C_{1-2}$ alkyl)$_3$, such as Si(CH$_3$)$_3$); and/or
$R^a$ and $R^b$, together with the C-atoms to which they are attached, form a fused phenyl ring that is substituted by one or more substituents selected from $C_{1-3}$ alkyl, $C_{1-3}$ haloalkyl, cyano and halo,
or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl, or, particularly, $R^a$ and $R^b$ together represent $C_{3-5}$ n-alkylene, which alkylene group is optionally substituted by one or more methyl substituents and/or which alkylene group optionally contains one C—C double bond between two C-atoms of the n-alkylene chain (e.g. $R^a$ and $R^b$ together represent $C_{3-4}$ n-alkylene, such as —$(CH_2)_4$—).

(31) A compound or salt according to any one of Embodiments (1) to (30) above, wherein:
Q represents phenyl substituted by -L-P(O)R'R" (e.g. in the para- or, particularly, the meta-position relative to the point of attachment of the phenyl group to the pyrazole group);
L is $CH_2$ or a direct bond;
R' represents $C_{1-2}$ alkyl (e.g. methyl);
R" represents $C_{1-2}$ alkyl (e.g. methyl);
or R' and R" together combine to form $C_{4-5}$ n-alkylene;
R is —$C(C_{1-2}$ alkyl$)_2$-$C_{2-3}$ alkynyl (e.g. —$C(CH_3)_2$—C≡C—H) or $Si(C_{1-2}$ alkyl$)_3$ (e.g. $Si(CH_3)_3$); and/or
$R^a$ and $R^b$ together represent $C_{3-4}$ n-alkylene (e.g. —$(CH_2)_4$—).

(32) A compound or salt according to any one of Embodiments (1) to (29) above, wherein:
Q represents thienyl, phenyl or pyridinyl, either of which may optionally bear 1 to 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $NH_2$, N(H)—$C_{1-6}$ alkyl, N($C_{1-6}$ alkyl$)_2$, $C_{1-6}$ alkylene-5-10 membered heterocycle and $C_{0-3}$ alkylene-O—$C_{0-6}$ alkylene-5-10 membered heterocycle;
R is $C_{1-6}$ alkyl, $C_{2-6}$ alkenyl, $C_{1-6}$ hydroxyalkyl, $C_{1-6}$ haloalkyl, $C_{1-6}$ alkyl substituted by $C_{1-3}$ alkoxy or cyano, $C_{0-2}$ alkylene-$C_{3-8}$ cycloalkyl optionally substituted with $C_{1-3}$ alkyl or a 4-5 membered heterocycle optionally substituted with $C_{1-3}$ alkyl; and
$R^a$ and $R^b$, together with the C-atoms to which they are attached, form a fused phenyl ring that is optionally substituted by one or more substituents selected from $C_{1-3}$ alkyl, $C_{1-3}$ haloalkyl, cyano and halo, or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl.

(33) A compound or salt according to any one of Embodiments (1) to (32) above, wherein one of $R^2$ and $R^3$ represents —$[C_{2-3}$ alkylene-O$]_{1-3}$—$[C_{2-3}$ alkylene]-$R^{2a}$, such as —$(CH_2CH_2O)_{2-3}CH_3$) and the other of $R^2$ and $R^3$ is as defined above in any of Embodiments (1) to (32) (e.g. the other of $R^2$ and $R^3$ is H).

(34) A compound or salt according to any one of Embodiments (1) to (33) above, wherein
R represents:
$C_{1-6}$ n-alkyl,
$C_{3-6}$ branched alkyl (e.g. $C_{4-6}$ branched alkyl),
$C_{2-6}$ alkenyl,
$C_{1-6}$ hydroxyalkyl,
$C_{1-6}$ haloalkyl,
$C_{1-6}$ alkyl substituted by $C_{1-3}$ alkoxy or cyano,
$C_{0-2}$ alkylene-$C_{3-8}$ cycloalkyl optionally substituted with $C_{1-3}$ alkyl, or
a 4-5 membered heterocycle optionally substituted with $C_{1-3}$ alkyl
(e.g. R represents ethyl, cyclopropyl, $CF_3$, $C_2F_5$, —$C(CH_3)_2CF_3$ or, particularly, 1-methylcyclopropyl, propen-2-yl or tert-butyl).

(35) A compound or salt according to any one of Embodiments (1) to (32) above, wherein one of $R^2$ and $R^3$ represents —$[C_{2-3}$ alkylene-O$]_{1-5}$—$[C_{2-3}$ alkylene]-$R^{2a}$ (e.g. —$[C_{2-3}$ alkylene-O$]_{1-4}$—$[C_{2-3}$ alkylene]-$R^{2a}$, such as —$(CH_2CH_2O)_{2-4}CH_3$) and the other of $R^2$ and $R^3$ is as defined above in any of Embodiments (1) to (32) (e.g. the other of $R^2$ and $R^3$ is H).

(36) A compound or salt according to Embodiment (35) above, wherein $R^1$ represents ethynyl or $OCH_3$.

(37) A compound or salt according to Embodiment (35) or Embodiment (36) above, wherein $R^2$ represents —$(CH_2CH_2O)_{2-4}CH_3$ and $R^3$ is H.

(38) A compound or salt according to any one of Embodiments (1) to (37) above, wherein
Q represents phenyl substituted in the para position by methyl, methoxy or dimethylamino and R represents isopropyl or, particularly, tert-butyl.

Exemplary compounds of formula (I) are selected from the group consisting of:
3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-(2-(2-methoxyethoxy)ethoxy)ethyl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;

3-((4-((4-(3-(3-(tert-butyl)-1-(4-methoxyphenyl)-1H-pyrazol-5-yl)ureido)naphthalen-1-yl)oxy)-pyrimidin-2-yl)amino)-5-ethynyl-N-(2-(2-(2-methoxyethoxy)ethoxy)ethyl)benzamide;

3-((4-((4-(3-(3-(tert-butyl)-1-(p-tolyl)-1H-pyrazol-5-yl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(3-(tert-butyl)-1-(4-methoxyphenyl)-1H-pyrazol-5-yl)ureido)-naphthalen-1-yl)oxy)pyrimidin-2-yl)amino)-5-ethynyl-N-(2-(2-methoxyethoxy)ethyl)benzamide;

3-((4-((4-(3-(3-(tert-butyl)-1-(2,3,5,6-tetradeutero-4-(trideuteromethyl)phenyl)-1H-pyrazol-5-yl)ureido)naphthalen-1-yl)oxy)pyrimidin-2-yl)amino)-5-ethynyl-N-(2-(2-(2-methoxyethoxy)-ethoxy)ethyl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2,5,8,11-tetraoxatridecan-13-yl)benzamide;

3-((4-((4-(3-(3-(tert-butyl)-1-(p-tolyl)-1H-pyrazol-5-yl)ureido)naphthalen-1-yl)oxy)-pyrimidin-2-yl)amino)-5-ethynyl-N-(2-(2-methoxyethoxy)ethyl)benzamide;

3-((4-((4-(3-(3-(tert-butyl)-1-(4-(dimethylamino)phenyl)-1H-pyrazol-5-yl)ureido)-naphthalen-1-yl)oxy)pyrimidin-2-yl)amino)-5-ethynyl-N-(2-(2-(2-methoxyethoxy)-ethoxy)ethyl)benzamide;

3-((4-((4-(3-(3-(tert-butyl)-1-(4-(dimethylamino)phenyl)-1H-pyrazol-5-yl)ureido)-naphthalen-1-yl)oxy)pyridin-2-yl)amino)-5-methoxy-N-(2-(2-(2-methoxyethoxy)-ethoxy)ethyl)benzamide;

3-((4-((4-(3-(3-(tert-butyl)-1-(4-(dimethylamino)phenyl)-1H-pyrazol-5-yl)ureido)-naphthalen-1-yl)oxy)pyridin-2-yl)amino)-5-ethynyl-N-(2-(2-(2-methoxyethoxy)-ethoxy)ethyl)benzamide;

3-((4-((4-(3-(3-(tert-butyl)-1-(p-tolyl)-1H-pyrazol-5-yl)ureido)-5,6,7,8-tetrahydronaphthalen-1-yl)oxy)pyrimidin-2-yl)amino)-5-ethynyl-N-(2-(2-(2-methoxyethoxy)ethoxy)ethyl)benzamide;

3-((4-((4-(3-(3-(tert-butyl)-1-(2,4-dimethoxyphenyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;

3-((4-((4-(3-(3-(tert-butyl)-1-(3-((dimethylphosphoryl)methyl)phenyl)-1H-pyrazol-5-yl)ureido) naphthalen-1- yl)oxy)pyrimidin-2-yl)amino)-5-ethynyl-N-(2-(2-(2-methoxyethoxy)ethoxy)ethyl)benzamide;
3-((4-((4-(3-(3-(tert-butyl)-1-(3-((dimethylphosphoryl)methyl)phenyl)-1H-pyrazol-5-yl)ureido)naphthalen-1-yl)oxy)pyridin-2-yl)amino)-5-methoxy-N-(2-(2-(2-methoxyethoxy)ethoxy)ethyl)benzamide;
3-((4-((4-(3-(3-(tert-butyl)-1-(4-(dimethylamino)phenyl)-1H-pyrazol-5-yl)ureido)naphthalen-1-yl)oxy)pyrimidin-2-yl)amino)-5-methoxy-N-(2-(2-(2-methoxyethoxy)ethoxy)ethyl)benzamide;
3-((4-((4-(3-(3-(tert-butyl)-1-(4-methoxy-2-methylphenyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide,
and pharmaceutically acceptable salts thereof.

Thus in one embodiment the compound of the invention is 3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide or a pharmaceutically acceptable salt thereof.

In an alternative embodiment, there is provided a compound of formula (I), (Ib1), (Ib2), (Ic1), (Ic2), (Id1), (Id2), (Ig1) or (Ig2) as defined above, or a pharmaceutically acceptable salt thereof, wherein the compound is not a compound of the formula:

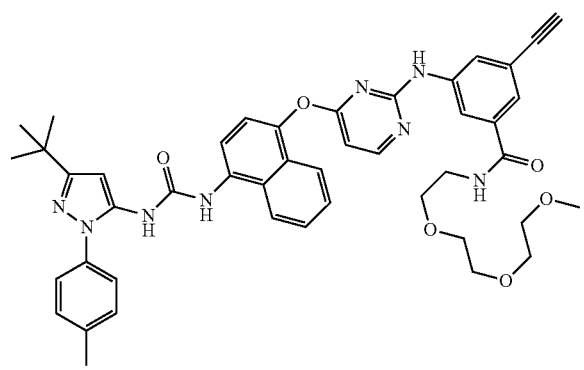 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCOCCOCCOC)c1]

or a pharmaceutically acceptable salt thereof, including all tautomers thereof.

In certain embodiments, there is provided a compound of formula (I), (Ib1), (Ib2), (Ic1), (Ic2), (Id1), (Id2), (Ig1) or (Ig2) as defined above, or a pharmaceutically acceptable salt thereof, wherein the compound is not:
3-((4-((4-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;
and/or
3-((4-((4-(3-(tert-butyl)-1-(2,3,5,6-tetradeutero-4-(trideuteromethyl)phenyl)-1H-pyrazol-5-yl)ureido)naphthalen-1-yl)oxy)pyrimidin-2-yl)amino)-5-ethynyl-N-(2-(2-(2-methoxyethoxy)-ethoxy)ethyl)benzamide,
or a pharmaceutically acceptable salt thereof.

The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

As employed herein below the definition of compounds of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

Generic routes by which compound examples of the invention may be conveniently prepared are summarised below. Those routes are specifically exemplified for compounds of formula (I) in which $R^a$ and $R^b$, together with the C-atoms to which they are attached, form a fused phenyl ring. However, compounds of formula (I) having other definitions of $R^a$ and $R^b$ may be prepared by analogous routes.

Thus, for example, compounds of formula (I) may be obtained by a general process (Scheme 1, Route A) whereby a naphthylamine precursor represented by Intermediate B is coupled with an activated, electrophilic derivative Intermediate A* prepared from the corresponding amine precursor, Intermediate A (G=H). The amine radical NR$^a$R$^b$ in compounds of Intermediate B either comprise the group Y, as defined for compounds of formula (I) above or a protected derivative of the same. The fragment LG$_1$ in Intermediate A* is a suitable leaving group such as an imidazolyl (C$_3$H$_3$N$_2$) or an aryloxy radical such as a phenoxy (C$_6$H$_5$O) group. It will be understood by persons skilled in the art that, in some instances, the compound represented by Intermediate A* may be isolated or in other cases may be a transient intermediate, that is not isolated, but generated in situ and used directly.

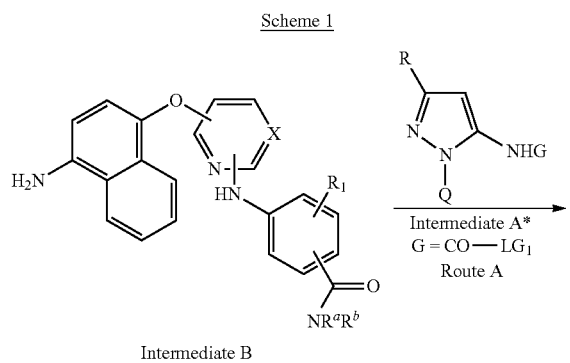

Scheme 1

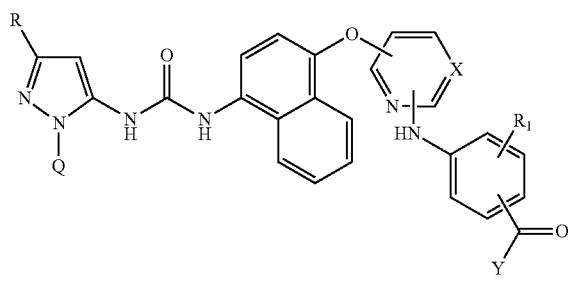

(I)

In the case wherein LG$_1$ is imidazolyl, compounds represented by Intermediate A* are obtained by reaction of the corresponding amine with an activating agent such as CDI in a non-polar aprotic solvent, such as DCM and are conveniently generated in situ at RT and then reacted without isolation with compounds represented by Intermediate B.

In the case wherein LG$_1$ is aryloxy the required activated amine may be generated by treatment of the amine precursor with a suitable chloroformate, such as, for example, phenyl chloroformate, in the presence of a base. In some instances it is advantageous to conduct the activation process under Schotten-Baumann type conditions, that is using an aqueous base, such as aq sodium carbonate under biphasic conditions. The activated amine derivatives represented by Intermediate A* wherein LG$_1$ is aryloxy, for example phenoxy, may thereby be generated optionally in situ and then reacted without isolation with compounds represented by Intermediate B to provide compound examples of formula (I).

Compounds of formula (I) may include those in which the substituent Y incorporates one or more functional groups that have been protected during the coupling process and therefore require(s) subsequent deprotection. An example of such a procedure is the removal of a tert-butoxycarbonyl (Boc) group from a secondary amine, by treatment with an appropriate acid.

Alternatively, compound examples of formula (I) may be generated by an S$_N$Ar displacement reaction between an electrophilic heteroaryloxy fragment represented by Intermediate C, wherein LG$_2$ is a suitable leaving group, typically a halogen atom, for example chlorine, with an aniline component represented by Intermediate D (Scheme 2, Route B). The reaction proceeds under acidic conditions, for example in the presence of p-TSA and in a polar aprotic solvent such as THF and typically at elevated temperatures, for example at 70° C.

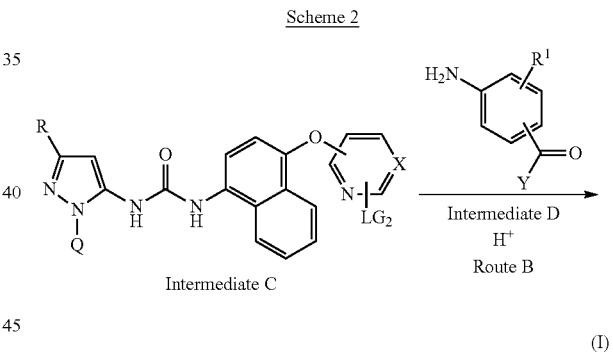

Scheme 2

(I)

Optionally, compound examples of the invention may be prepared by a general synthetic process comprising of an amide bond forming reaction between a carboxylic acid derivative with an amine R$^a$R$^b$NH (Scheme 3, Routes C$_1$ and C$_2$) whereby NR$^a$R$^b$ comprises Y or a protected derivative thereof, in which latter case the compounds of formula (I) are revealed following an appropriate deprotection step(s). The amide coupling may be conducted on an alkyl ester represented by Intermediate E (R$^c$=alkyl), for example a methyl ester, with the amine, in the presence of a trialkylaluminium, for example trimethylaluminium (Scheme 3, Route C$_1$). The reaction is conveniently carried out in an aprotic solvent such as THF and at ambient or slightly elevated temperatures, typically RT to 40° C.

Scheme 3

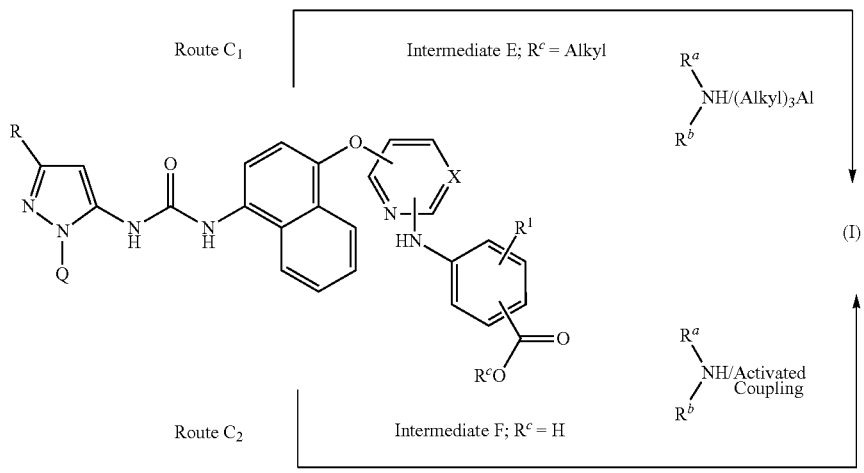

Alternatively the amide products of formula (I) may be derived from the parent carboxylic acids represented by Intermediate F ($R^c$=H) by reaction with the amine $R^aR^bNH$ under the influence of an amide (peptide) coupling reagent, and in the presence a non-nucleophilic base (Scheme 3, Route $C_2$). An example of a reagent that is frequently employed for these transformations is HATU and suitable bases include DIPEA and N-methylmorpholine and the like. The amidation reaction is typically conducted in polar aprotic solvents such as THF and at ambient temperature.

The above and other routes may be used to prepare the compound of formula (I). Thus, according to a further aspect of the invention, there is provided a process for the preparation of a compound of formula (I) which process comprises:

(a) reaction of a compound of formula (II),

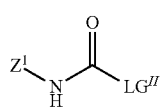
(II)

with a compound of formula (III)

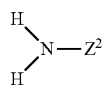
(III)

wherein $LG^{II}$ represents a suitable leaving group (e.g. imidazolyl, halo (such as chloro) or, particularly, aryloxy (such as phenoxy)) and one of $Z^1$ and $Z^2$ is a structural fragment of formula (IV)

(IV)

wherein R and Q are as hereinbefore defined, and the other of $Z^1$ and $Z^2$ is a structural fragment of formula (V)

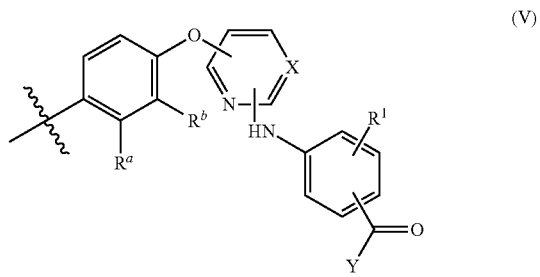
(V)

wherein $R^1$, $R^a$, $R^b$, X and Y are as hereinbefore defined (e.g. in one particular embodiment, $Z^1$ is a structural fragment of formula (IV) and $Z^2$ is a structural fragment of formula (V)), for example under conditions known to those skilled in the art, such as from ambient temperature to about 80° C. (e.g. from 50 to 60° C.), optionally in the presence of an amine base (e.g. a trialkylamine such as N,N-diisopropylethylamine or, particularly, triethylamine) and a suitable organic solvent (e.g. an aprotic solvent, such as dichloromethane or, particularly, an ester such as isopropyl acetate);

(b) reaction of a compound of formula (VI),

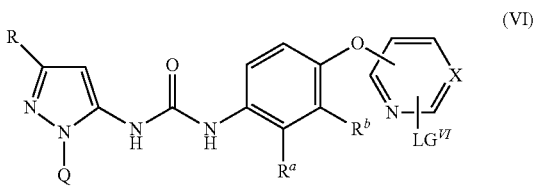

(VI)

wherein R, $R^a$, $R^b$, Q and X are as hereinbefore defined and $LG^{VI}$ represents a suitable leaving group (e.g. a halo group such as bromo or, particularly, chloro), with a compound of formula (VII),

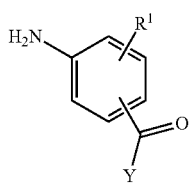

(VII)

wherein $R^1$ and Y are as hereinbefore defined, under conditions known to those skilled in the art (e.g. as described in *J. Am. Chem. Soc.* 2011, 133, 15686-15696), such as at elevated temperature (e.g. from 50 to 110° C., such as at about 60° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid);

(c) reaction of a compound of formula (VIII),

(VIII)

with a compound of formula (III), wherein the compound of formula (III) and $Z^1$ and $Z^2$ are as hereinbefore defined, under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(d) reaction of a compound of formula (IX),

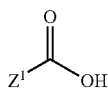

(IX)

wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula (VIII), which compound is then reacted with a compound of formula (III), as defined above, to provide the compound of formula (I);

(e) reaction of a compound of formula (X)

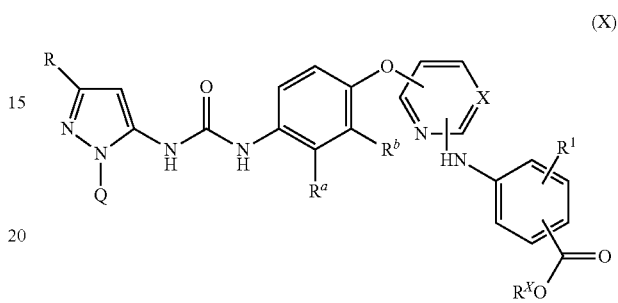

(X)

wherein R, $R^1$, $R^a$, $R^b$, Q and X are as hereinbefore defined and $R^X$ represents H or $C_{1-4}$ alkyl, with a compound of formula (XI)

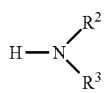

(XI)

wherein $R^2$ and $R^3$ are as hereinbefore defined, under conditions known to those skilled in the art, for example when $R^X$ represents H, reaction in the presence of a suitable solvent, a base (e.g. triethylamine or N,N-diisopropylethylamine) and an amide (peptide) coupling reagent, such as HATU, CDI, N,N'-dicyclohexylcarbodiimide, N,N'-diisopropylcarbodiimide BOP or PyBOP, optionally in combination with an activated ester-forming agent such as HOBt or 1-hydroxy-7-azabenzotriazole, when $R^X$ represents H, conversion of the carboxylic acid to an acid halide (e.g. by reaction with a halogenating agent such as thionyl chloride), followed by reaction with the compound of formula (XI) in the presence of a suitable solvent and a base (e.g. triethylamine or N,N-diisopropylethylamine), or when $R^X$ represents $C_{1-4}$ alkyl (e.g. methyl), reaction in the presence of a trialkylaluminium (e.g. trimethylaluminium) and an aprotic solvent (e.g. THF); or (f) deprotection of a protected derivative of a compound of formula (I), under conditions known to those skilled in the art, wherein the protected derivative bears a protecting group on an O- or N-atom of the compound of formula (I) (and, for the avoidance of doubt, a protected derivative of one compound of formula (I) may or may not represent another compound of formula I).

Compounds represented by Intermediate A are either commercially available, or may be prepared by synthetic approaches that are well established in the art. For example compounds of this general structure may be prepared by condensation of the appropriate hydrazine, optionally in the form of a protected derivative thereof or a suitable salt, with the relevant ketonitrile (Scheme 4). An example of an appropriate salt is a hydrochloride salt, and a suitable protective group for this transformation is an acid labile carbamate, for example a Boc group ($R^d$=tert-Bu) that is readily removed under the cyclisation conditions Scheme 4

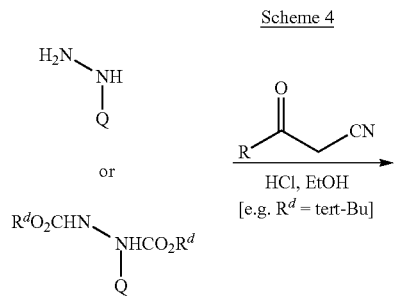

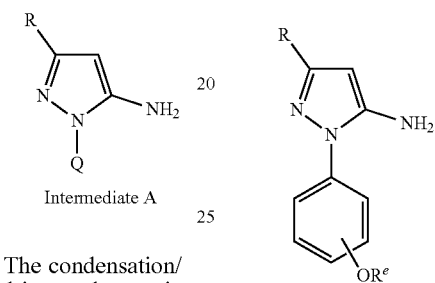

Intermediate A to generate the parent hydrazine in situ. The condensation/cyclisation reaction is suitably conducted in a polar protic solvent such as ethanol and in the presence of a strong acid for example concentrated hydrochloric acid and at elevated temperatures, typically at reflux.

In some instances it may be advantageous to prepare such intermediates by one or other alternative methodologies, as best suits the availability of starting materials and/or the functionality represented in the compounds and/or the need to protect one or more of them, during the synthetic processes in question or in subsequent transformations. For example compounds represented by Intermediate A may also be accessed via a copper (I) mediated coupling reaction between a 1H-pyrazol-5-amine and a suitable arene Q-LG$_3$ in which Q is an optionally substituted aromatic nucleus as defined for compounds of formula (I) and LG$_3$ is a halide such as an iodine atom (Scheme 5). The reaction is conveniently conducted in an Scheme 5

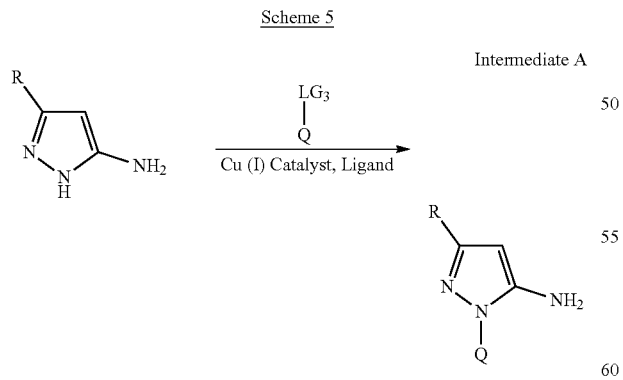

aprotic non-polar solvent such as toluene, employing a copper (I) salt as the catalyst, for example copper (I) iodide and in the presence of a copper co-ordinating ligand such as $N^1,N^2$-dimethylcyclohexane-1,2-diamine and in the presence of a base, for example potassium carbonate and typically at elevated temperature for example at reflux.

It will be evident to those skilled in the art that it may be advantageous to convert one intermediate described herein into another example of the same by one or more transformations that are well known and precedented and thereby gain access to additional compounds of the invention. As an example of such a process those compounds represented by Intermediate A wherein Q is a phenyl ring substituted with an alkoxy group (OR$^e$ wherein R$^e$ is alkyl), such as a methoxy group, may be converted into the corresponding phenol by an O-dealkylation reaction (Scheme 6). This type of transformation may be effected with a boron trihalide, for example boron tribromide, in a non-polar, aprotic solvent such as DCM, at reduced temperatures for example at −5 to 0° C.

Scheme 6

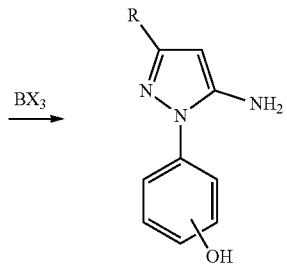

A further demonstration of the conversion of one intermediate, into another compound of the same generic type is provided by the functionalisation of the phenol examples of Intermediate A described hereinabove. For example intermediates of this composition can be conveniently alkylated on the phenolic oxygen by reaction with an alkyl halide, for example with a simple alkyl bromide. Alternatively, the phenol products may be reacted with a functionalised alkyl halide, for example with a nitrogen mustard, that is, with a salt of a 2-haloethylamine of formula $R^f(CH_2)_2LG_4$, wherein LG$_4$ is a halogen such as a chlorine and $R^f$ is selected such that O(CH$_2$)$_2$R$^f$ is allowable by the definition of Q in compounds of formula (I)

Scheme 7

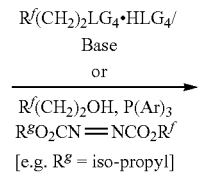

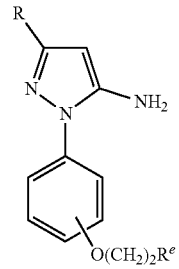

or is a suitably protected derivative thereof (Scheme 7). An example of a salt of a 2-haloethylamine that could be used in O-alkylations of this kind is 4-(2-chloroethyl)morpholine hydrochloride. Reaction of this kind are usefully undertaken in polar non protic solvents such as acetonitrile or DMF and in the presence of a base such as potassium carbonate and with heating if necessary.

In some instances it may be advantageous to effect the O-alkylation under Mitsunobu conditions, by interaction of the phenol with the corresponding alcohol $R^f(CH_2)_2OH$ in the presence of a triaryl phosphine such as triphenyphosphine, together with a suitable diazodicarboxylate coupling reagent, for example diisopropyl diazene-1,2-dicarboxylate. Such reactions are typically carried out in non-polar, aprotic solvents such as THF at reduced to ambient temperatures, for example at −50° C. to RT.

Other examples of Intermediate A may be prepared by interconversion of substituents on the phenyl, pyridyl or thienyl ring of group Q. For example, examples of Intermediate A bearing the substituent —$(CH_2)_{1-2}P(O)R'R''$ may be obtained by coupling of equivalent compounds bearing the substituent —$(CH_2)_{1-2}Hal$, where Hal is a leaving group such as chloro, bromo or iodo, with a compound of the formula H—P(O)R'R''. The reaction may be performed, for example, by heating in a polar aprotic solvent (e.g. DMF) in the presence of a palladium-containing catalyst (e.g. a Pd(II) catalytic species, such as Pd(II) acetate, optionally in the presence of a bidentate phosphine ligand such as 4,5-bis(diphenylphosphino)-9,9-dimethylxanthene (Xantphos)) Alternatively, the coupling reaction may be with a compound of formula ($C_{1-4}$ alkyl)-O—PR'R'', using Arbuzov-type conditions (WO 2010/141406; *Bioorg. Med. Chem. Lett.* 2009, 19, 2053-2058), with compounds having the —$(CH_2)_{1-2}Hal$ substituent mentioned above. (Compounds of formula ($C_{1-4}$ alkyl)-O—PR'R'' are typically made in situ by reaction of the corresponding chlorophosphine (Cl—PR'R'') with a $C_{1-4}$ alkyl alcohol in the presence or a base (e.g. diisopropylethylamine), or with an alkali metal salt of a $C_{1-4}$ alkyl alcohol.)

Compounds represented by Intermediate B may be obtained from $S_NAr$ displacement reactions between electrophilic aryloxy naphthylamines represented by Intermediate G, wherein $LG_2$ is a suitable leaving group such as a halogen atom, for example chlorine, with an aniline component represented by Intermediate D (Scheme 8). The coupling reaction may be undertaken on the free naphthylamine ($G_1$=H) or optionally, in order to control chemoselectivity and thereby enhance efficiency, upon a protected derivative thereof Scheme 8

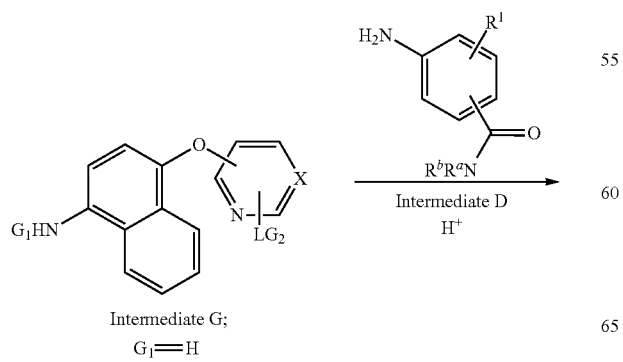

Intermediate G;
$G_1$=H

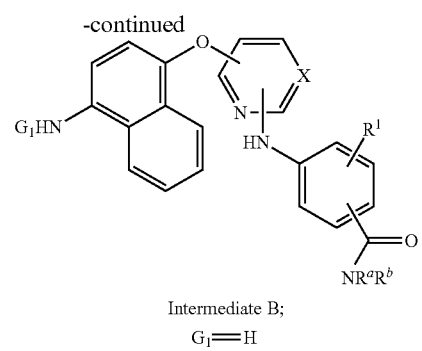

Intermediate B;
$G_1$=H

Intermediate G(P) ($G_1$=protective group). The reaction proceeds under acidic conditions, for example in the presence of p-TSA and in a polar aprotic solvent such as THF and typically at elevated temperatures, for example at 70° C. In those instances in which a protective group has been employed the products represented by Intermediate B are subsequently revealed by a suitable deprotection step(s). For example a carbamate, such as a Boc group, may be used to protect the naphthylamine nitrogen ($G_1$=tert-BuO$_2$C) during the $S_NAr$ coupling reaction and afterwards removed by treatment with a strong acid, for example with TFA.

The synthetic processes cited hereinabove (Routes $C_1$ and $C_2$, Scheme 3) may likewise be exploited to access compounds represented by Intermediate B (Scheme 9). Thus examples of Intermediate B may be prepared by reaction of an activated derivative of a carboxylic acid represented by Intermediate J ($R^c$=$G_1$=H) or a protected derivative thereof. Intermediate J(P) ($G_1$=protective group) with an amine $R^aR^bNH$, whereby $NR^aR^b$ comprises Y or a protected derivative thereof. Alternatively the interconversion may be undertaken on an ester Intermediate H ($R^c$=alkyl, $G_1$=H) or a protected derivative thereof. Intermediate H(P) ($R^c$=alkyl, $G_1$=protective group) with an amine $R^aR^bNH$ in the presence of a trialkyl aluminium, as already described. A suitable protective group for these transformations is a urethane Scheme 9

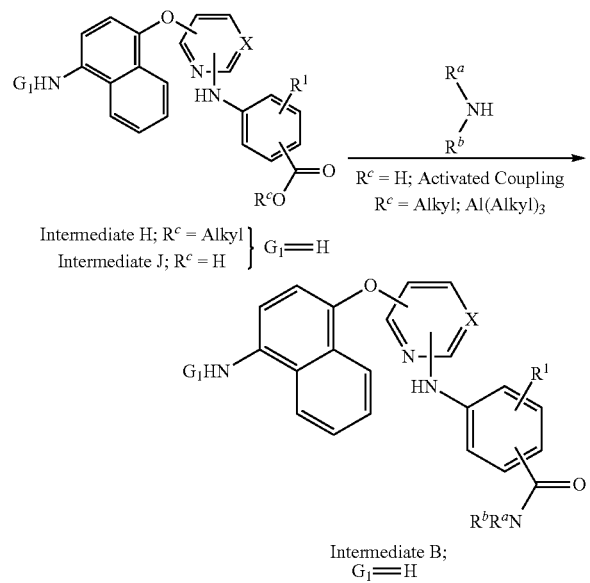

Intermediate B;
$G_1$=H derivative ($G_1=R^hO_2C$) in which case the desired anilines ($G_1=H$) represented by Intermediate B are obtained following an appropriate deprotection procedure. An example of a urethane protective group which is suitable for this purpose is a Boc group ($G_1=\text{tert-BuO}_2C$), which can be removed following the amidation reaction by treatment with acid.

The ester and acid precursors represented by Intermediates E and F are obtainable by use of the same or analogous procedures, to those disclosed hereinabove (Scheme 1), that provide compound examples of the present invention. In this manner Intermediates E and F are conveniently obtained by the reaction of Intermediates H and J respectively with the activated aminopyrazole derivatives Intermediates A* (Scheme 10). It will be evident to those skilled in the art that the esters: Intermediates H and E may be readily transformed into the corresponding carboxylic acids: Intermediates J and F by hydrolysis under suitable acidic or basic conditions. For example this conversion can be effected by saponification, using a base such as lithium hydroxide, in a protic solvent or mixture of solvents, for example THF and water and at modestly elevated temperatures, typically RT to 40° C.

matic (Scheme 11), for example a dihalo heteroaromatic wherein the leaving groups $LG_2$ and $LG_5$ are both halogen atoms,

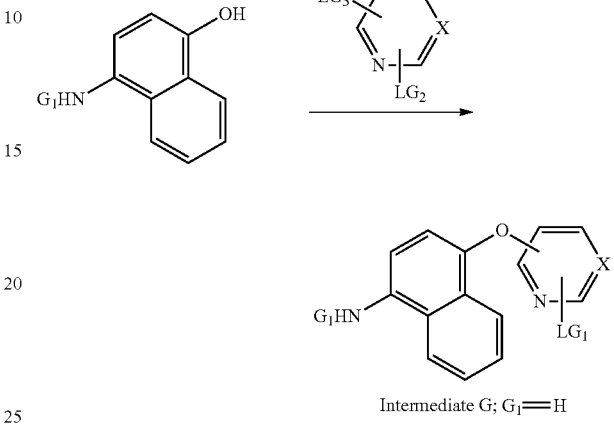

Scheme 11

Intermediate G; $G_1=H$ such as chlorine. A suitable protective group for this transformation is a Boc group ($G_1=\text{tert-BuO}_2C$) which may be retained, in order to control chemoselectivity, during one or more subsequent transformations, such as those described hereinabove (Schemes 8 and 9). The displacement step is conveniently carried out in a polar, aprotic solvent such as acetonitrile and in the presence of a hindered base, typified by DBU and at reduced temperature, for example at 0° C.

Those compounds represented by Intermediates H and J were assembled by analogous synthetic procedures to those already described above (Scheme 8) for the preparation of Intermediates B by substituting anilino acids or anilino esters represented by Intermediate K in place of Intermediate D (Scheme 12). In a similar manner the acid mediated $S_NAr$ coupling may be conducted on the free naphthylamine Intermediate G ($G_1=H$) or optionally, using a protected derivative of the same, Intermediate G(P) ($G_1=$protective group), to maintain the desired chemoselectivity in this and/or subsequent transformations. The $S_NAr$ coupling is suitably carried out in a polar non protic solvent, for example THF or IPA or DMF and in the presence of an acid catalyst such as p-TSA or TFA and most usually at elevated temperatures, typically at 60-70° C. In alternative procedures, a Buchwald-Hartwig amination may be performed, for example at elevated temperature (e.g. 20 to 120° C.) using a palladium catalyst (e.g. a combination of $Pd_2dba_3$ and BINAP) and base (e.g. $Cs_2CO_3$). In instances where the phenyl group of the aniline bears a substituent that is sensitive to palladium-catalysed reactions (e.g. an ethynyl group), then Intermediate K may be replaced by Intermediate K*, in which the sensitive (e.g. ethynyl) group is in protected form (e.g. for ethynyl, in trialkylsilyl-protected form, such as in triisopropylsilane-protected form). The protective group may then be removed under conditions known to those skilled in the art. For example, a triisopropylsilyl group can be removed with a source of fluoride ion, e.g., tetrabutylammonium fluoride (TBAF) or caesium fluoride.

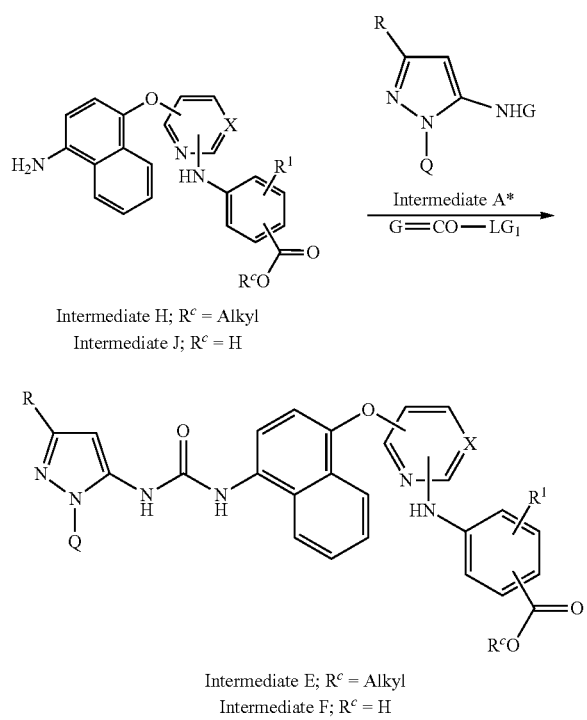

Scheme 10

Intermediate H; $R^c$ = Alkyl
Intermediate J; $R^c$ = H

Intermediate E; $R^c$ = Alkyl
Intermediate F; $R^c$ = H

The precursors represented by Intermediate G are conveniently prepared by an $S_NAr$ displacement reaction between 4-aminonaphthalen-1-ol, either in the form of a salt or a suitable, protected derivative and an electrophilic heteroaro- Scheme 12

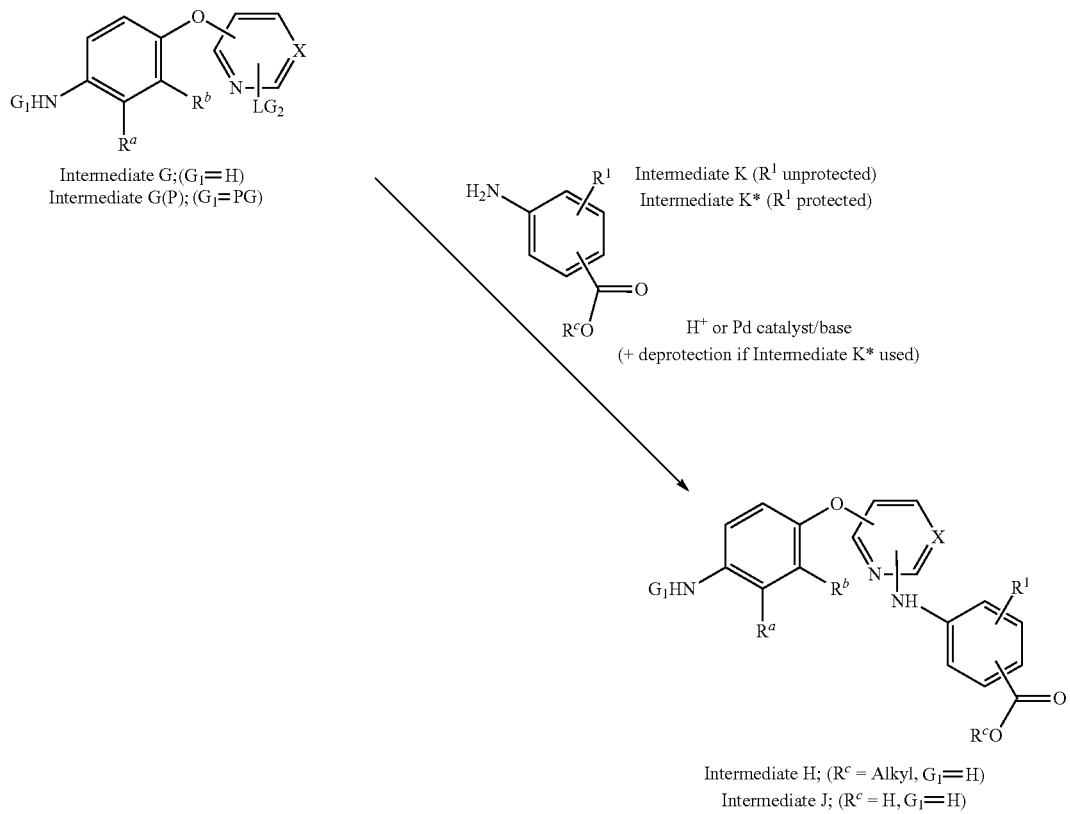

The known aniline components represented by Intermediate K were either procured from commercial sources or prepared according to published procedures. Novel examples of Intermediate D and Intermediate K disclosed herein were synthesised from commercially available starting materials using functional group interconversions that are well established in the art (Scheme 13). For example, the (leaving) group $LG_6$ may be displaced with a desired $R^1$ group via an $S_NAr$ reaction or transition metal-catalysed coupling. In some instances the desired anilines are readily obtainable from appropriately substituted, amino benzoic acids ($R^c=G_2=H$) and/or amino benzoic acid esters ($R^c$=alkyl $G_2$=H) that may be optionally N-protected ($G_2$=PG) to ensure that subsequent reactions can be conducted effectively. Transposition of the substituent $R^h$ into a group $R^1$ as defined for compounds of formula (I), provides compounds represented by Intermediate K which may be hydrolysed and subjected to an amide coupling reaction to furnish examples of Intermediate D, after removal, where employed, of the nitrogen protective group.

Scheme 13

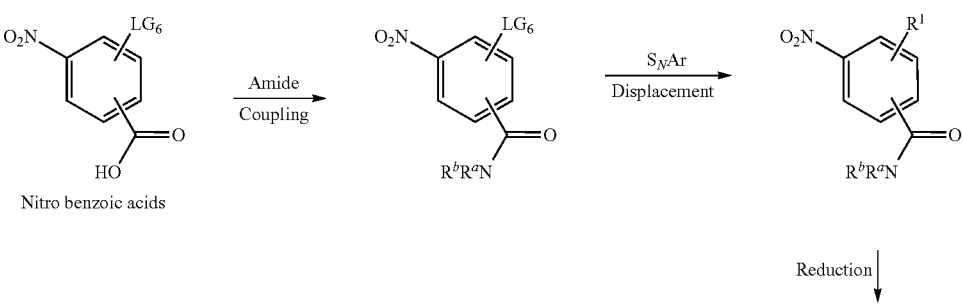

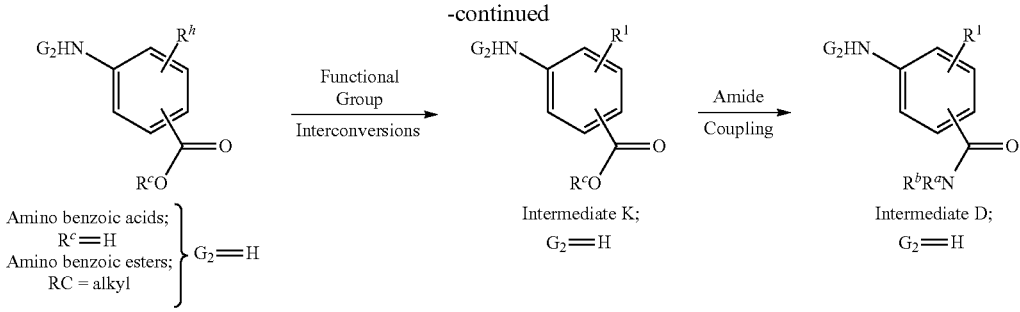

Additional examples of Intermediate D are readily made from commercially available (protected) amino or nitro benzoic acids that are substituted with a suitable (leaving) group $LG_6$, such as a halogen, for example fluorine or, particularly, bromine. Compounds of this composition may be converted into the examples of the desired anilines by a series of reactions comprising of an amide coupling, followed by an $S_NAr$ displacement reaction and reduction of the nitro group into an amine. Alternatively, for preparing examples of Intermediate D in which $R^1$ represents —C≡C—$(C_{1-4}$ alkylene$)_{0-1}$-H, the (protected) amino or nitro benzoic acids may undergo a Sonogashira coupling reaction and (for protected amino or nitro compounds) either deprotection of the amino group or reduction of the nitro group into an amine. Alternatively, the Sonogashira coupling reaction may be performed before the amide coupling (Scheme 14). In either alternative, when the alkynyl moiety introduced by way of the Sonogashira coupling reaction is ethynyl, it is introduced in protected form (e.g. in trialkylsilyl-protected form, through use of an ethynyltrialkylsilane, such as ethynyltriisopropylsilane). In such instances, the protective (e.g. trialkylsilyl) group may be removed under conditions known to those skilled in the art. For example, a triisopropylsilyl group can be removed with a source of fluoride ion, e.g., tetrabutylammonium fluoride (TBAF) or caesium fluoride. For the Sonogashira coupling reaction, group $LG_6$ is suitably a halo group such as chloro, iodo or, particularly, bromo.

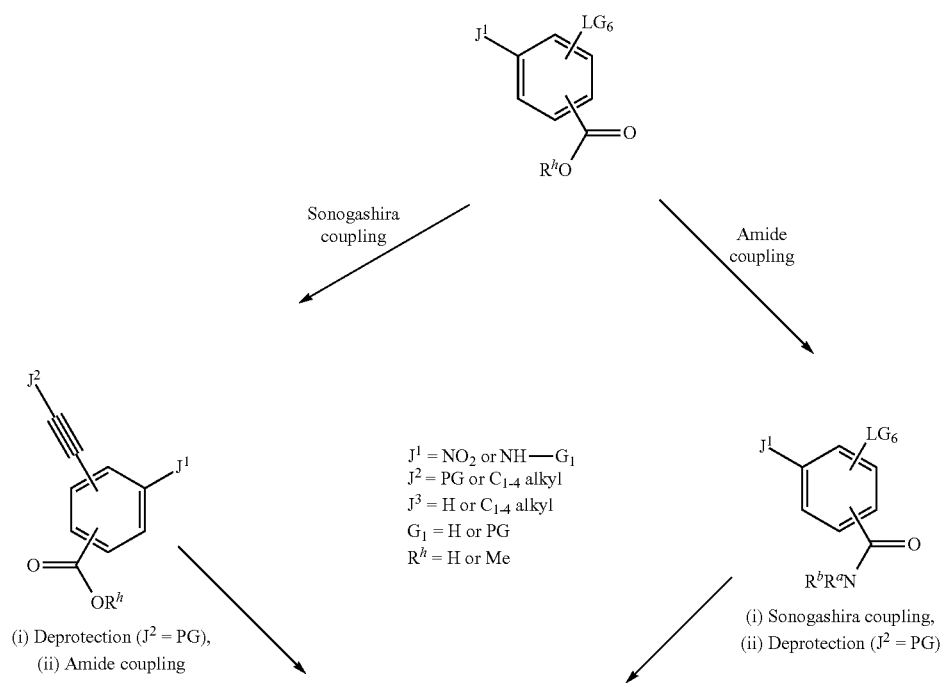

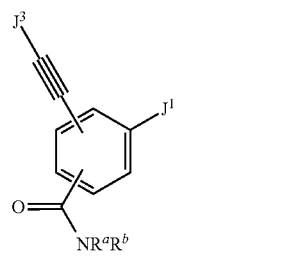

Reduction (J¹ = NO₂) or
Deprotection (J¹ = NH-PG)

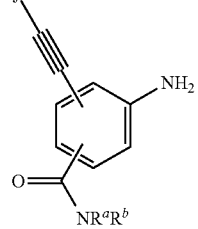

Compounds of formula (I) may alternatively be obtained by coupling of Intermediate B to an pyrazole-5-isocyanate compound, Intermediate L. In this route, Intermediate L may, for example, be conveniently prepared via a copper (II)-mediated Chan-Lam reaction (see, for example: *Tetrahedron Lett.* 1998, 39, 2941-2944), wherein an ester of a suitable pyrazole-5-carboxylic acid is coupled to an aryl- or heteroaryl-boronic acids. The resulting N-aryl pyrazole acid ester is saponified to yield the corresponding carboxylic acid (Intermediate M), which acid is converted to an acyl azide (e.g. using source of a leaving group and activated azide ion, such as diphenyl phosphorazidate (DPPA); see, for example, *Tetrahedron* 1974, 30, 2151-2157)) before undergoing a Curtis rearrangement to yield Intermediate L.

-continued

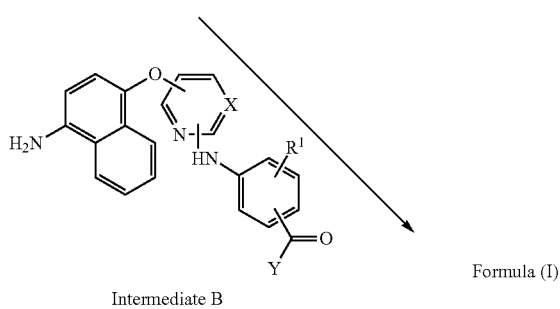

Intermediate B

Formula (I)

As exemplified in Scheme 15 above, examples of Intermediate M(P) may be prepared by metal-catalysed coupling of pyrazole acid esters to suitable compounds containing aromatic group Q. However, other examples of Intermediate M(P) may be prepared by further elaboration of compounds so obtained. For example, when Q is phenyl, a chloro, bromo or iodo substituent on the phenyl group in a compound of Intermediate M(P) may be displaced by cross-coupling with a variety of nucleophilic groups, such as a dialkylphosphine oxide (Scheme 16). The cross-coupling typically employs a palladium-containing catalyst (e.g. a Pd(II) catalytic species, such as Pd(II) acetate, optionally in the presence of a bidentate phosphine ligand such as 4,5-bis(diphenylphosphino)-9,9-dimethylxanthene (Xantphos); see, for example, WO 2009/143389).

Scheme 15

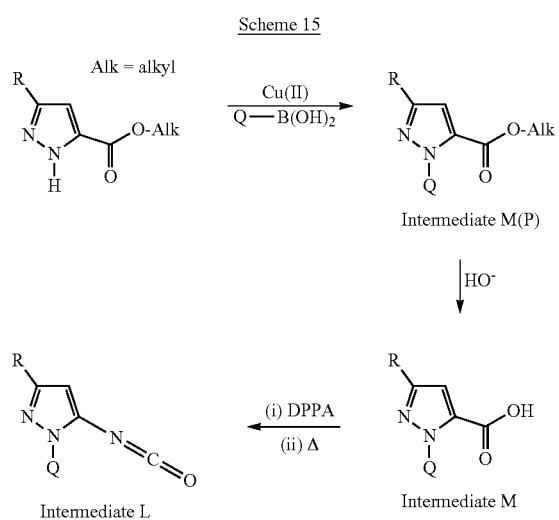

Scheme 16

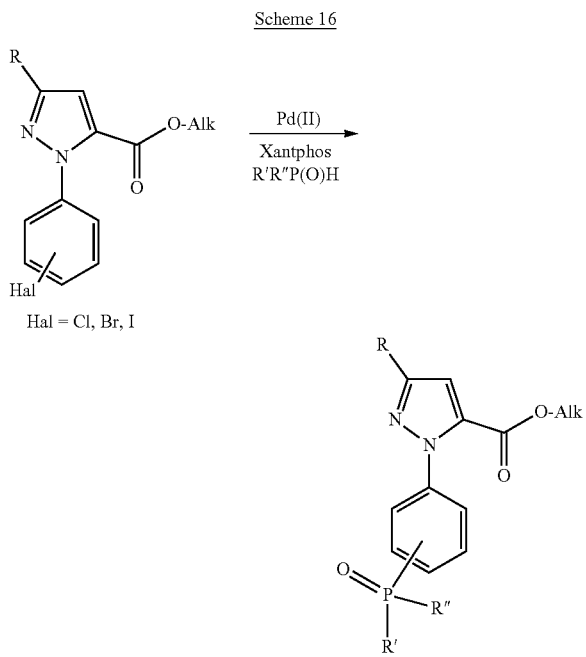

Hal = Cl, Br, I

It will be evident to those skilled in the art that in some cases it is technically advantageous to use alternative protective groups and/or to conduct the transformations described above in a similar manner but in a different order, so as to improve the overall efficiency of the synthetic processes.

Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates as described herein form an aspect of the invention. In this respect, further aspects of the invention relate to:
(i) a compound of formula (III) as hereinbefore defined, wherein $Z^2$ represents a structural fragment of formula (V), as hereinbefore defined, or a salt or protected derivative thereof; and
(ii) Intermediate D, as hereinbefore defined (i.e. a compound of formula (VII), as hereinbefore defined) or a salt or protected derivative thereof.

Protected derivatives of Intermediates B and D include amides or, particularly, carbamates of those compounds. For example, those protected derivatives include compounds in which a H-atom of the $NH_2$ group is replaced by:
R'—C(O)—, wherein R' is H, $C_{1-8}$ alkyl, phenyl or benzyl, which latter two groups are optionally substituted by one or more groups selected from halo, hydroxy, methyl and methoxy; or
R"—O—C(O)—, wherein R" is tert-butyl, phenyl, benzyl or fluorenyl, which latter three groups are optionally substituted by one or more groups selected from halo, hydroxy, methyl and methoxy.

The compounds of formula (I) are p38 MAP kinase inhibitors (especially of the alpha subtype) and in one aspect the compounds are useful in the treatment of inflammatory diseases, for example COPD and/or asthma.

Surprisingly, in at least some embodiments, the compounds of formula (I) exhibit a long duration of action and/or persistence of action.

In one embodiment the compounds of formula (I) do not strongly inhibit, or bind to GSK 3α, for example they have an $IC_{50}$ value against GSK 3α of 1500 nM or greater; such as 2,000, 3,000, 4,000, 5,000, 6,000, 7,000, 8,000, 9,000 or 10,000 nM or greater.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compounds of formula (I) are expected to be potent in vivo.

Typically, the prior art compounds developed to date have been intended for oral administration. This strategy involves optimizing the pharmacokinetic profile of drug substances in order to achieve an adequate duration of action. In this manner a sufficiently high drug concentration is established and maintained between doses to provide sustained clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ, that is, to exploit topical administration. Whilst this approach is not suitable for treating all chronic inflammatory diseases, it has been exploited in lung disorders, such as asthma and COPD; in skin diseases, for example against atopic dermatitis and psoriasis; for nasal conditions, typified by allergic rhinitis; and in gastrointestinal diseases, such as ulcerative colitis and Crohn's disease and inflammatory diseases of the eye, such as uveitis.

In topical therapy, one way in which efficacy can be achieved is by the use of a drug that has a sustained duration of action and is retained in the relevant organ, thereby minimizing the risk of systemic toxicity. Alternatively, in some cases, a formulation can be developed that generates a "reservoir" of the active drug which is available to sustain its desired effects. The first approach is exemplified by the anticholinergic drug tiotropium (Spiriva). This compound is administered topically to the lung as a treatment for COPD, and has an exceptionally high affinity for its target receptor resulting in a very slow off rate and consequently displays a sustained duration of action.

In one aspect of the disclosure the compounds of formula (I) is particularly suitable for topical delivery, such as topical delivery to the lungs, in particular for the treatment of respiratory disease, for example chronic respiratory diseases such as COPD and/or asthma.

In one embodiment the compounds of formula (I) is suitable for sensitizing patients to treatment with a corticosteroid who have become refractory to such treatment regimens.

The compounds of formula (I) may have antiviral properties (such as those described in WO 2011/070368 and/or WO 2011/070369), for example the ability to prevent the infection of cells (such as respiratory epithelial cells) with a picornavirus, in particular a rhinovirus, influenza or respiratory syncytial virus.

Thus, in view of their kinase inhibition profiles, the compounds are thought to be antiviral agents, in particular suitable for the prevention, treatment or amelioration of picornavirus infections, such as rhinovirus infection, influenza or respiratory syncytial virus.

In one embodiment the compounds of formula (I) are able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay.

In one embodiment the compounds of formula (I) are able to reduce ICAM1 expression induced by rhinovirus, especially in vivo. ICAM1 is the receptor mechanism used by so-called major groove rhinovirus serotypes to infect cells. This activity may be measured, for example by a method described herein.

It is expected that the above properties render the compounds of formula (I) particularly suitable for use in the treatment (including prophylaxis) of exacerbations of inflammatory diseases, in particular viral exacerbations, or in the treatment of viral infections, in patients with one or more chronic conditions such as congestive heart failure, COPD, asthma, diabetes, cancer and/or in immunosuppressed patients, for example post-organ transplant. Such use may be in combination with anti-viral agents such as zanamivir, oseltamivir (for example oseltamivir phosphate) peramivir or laninamivir.

In general, the compounds of formula (I) may be useful in the treatment of one or more conditions having an inflammatory component which, suitably, may be treated by topical or local therapy.

In particular, the compounds of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema).

The compounds of formula (I) may be useful in the treatment of eye diseases or disorders including keratoconjunctivitis sicca (dry eye), allergic conjunctivitis, conjunctivitis, diabetic retinopathy, macular oedema (including wet macular oedema and dry macular oedema), post-operative cataract inflammation or, particularly, uveitis (including posterior, anterior and pan uveitis) (e.g. eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis)).

The compounds of formula (I) may be useful in the treatment of skin diseases or disorders including allergic dermatitis, contact dermatitis, atopic dermatitis or psoriasis.

The compounds of formula (I) may be useful in the treatment of gastrointestinal diseases or disorders including ulcerative colitis or Crohn's disease.

The compounds of formula (I) may be useful in the treatment of joint diseases or disorders including rheumatoid arthritis or osteoarthritis and particularly inflamed joints secondary to such conditions.

The compounds of formula (I) may be useful in the treatment of cancers including cancer of the stomach and in the inhibition of the growth and metastasis of tumours including non-small cell lung carcinoma, gastric carcinoma, colorectal carcinomas and malignant melanoma.

It is also expected that the compounds of formula (I) may be useful in the treatment of certain other conditions including periodontitis, gingivitis and pharyngitis.

Compounds of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

The present invention also provides a process for preparing such a pharmaceutical composition (for example a pharmaceutical composition for parenteral, oral, topical, mucosal or rectal administration) which comprising mixing the ingredients.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung, eye or bowel. Hence we provide according to the invention a pharmaceutical composition comprising a compound of the disclosure optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compounds of the present invention (i.e. compounds of formula (I), (Ia1), (Ia2), (Ib1), (Ib2), (Ic1), (Ic2), (Id1), (Id2), (Ie1), (Ie2), (If1), (If2), (Ig1), (Ig2), (Ih1) or (Ih2), as defined above, or pharmaceutically acceptable salts thereof) may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of the present invention. In addition, the compound of the present invention may also be introduced by means of ocular implants or inserts.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 9'74p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

A compound of formula (I) has therapeutic activity. In a further aspect, the present invention provides a compound of the disclosure for use as a medicament. Thus, in a further aspect, the present invention provides a compound as described herein for use in the treatment of one or more of the above mentioned conditions.

In one embodiment a dry powder formulation according the present disclosure comprises magnesium or calcium stearate. Such formulations may have superior chemical and/or physical stability especially when such formulations also contain lactose.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the disclosure or a pharmaceutical composition comprising the compound.

The word "treatment" is intended to embrace prophylaxis as well as therapeutic treatment. Treatment of conditions or disorders also embraces treatment of exacerbations thereof.

A compound of the disclosure may also be administered in combination with one or more other active ingredients e.g. active ingredients suitable for treating the above mentioned conditions.

For example, possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol), xanthines (e.g. theophylline), anticholinergics (e.g. ipratropium or tiotropium, for example as the bromide) and anti-viral agents (e.g. zanamivir, oseltamivir, for example as the phosphate, peramivir and laninamivir).

Further, for the treatment of gastrointestinal disorders (such as Crohn's disease or ulcerative colitis), possible combinations include combinations with, for example, one or more agents selected from the list comprising:
  5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g., infliximab, adalimumab, certolizumab pegol or golimumab);
  anti-IL12/IL23 antibodies (e.g., ustekinumab) or small molecule IL12/IL23 inhibitors (e.g., apilimod);
  Anti-α4β7 antibodies (e.g., vedolizumab);
  MAdCAM-1 blockers (e.g., PF-00547659);
  antibodies against the cell adhesion molecule α4-integrin (e.g., natalizumab);
  antibodies against the IL2 receptor α subunit (e.g., daclizumab or basiliximab);
  JAK3 inhibitors (e.g., tofacitinib or R348);
  Syk inhibitors and prodrugs thereof (e.g., fostamatinib and R-406);
  Phosphodiesterase-4 inhibitors (e.g., tetomilast);
  HMPL-004;
  probiotics;
  Dersalazine;
  semapimod/CPSI-2364; and
  protein kinase C inhibitors (e.g. AEB-071).

For the treatment of eye disorders (such as keratoconjunctivitis sicca or uveitis), possible combinations include combinations with, for example, one or more agents selected from the list comprising:
  corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g., infliximab, adalimumab, certolizumab pegol, ESBA-105 or golimumab);
  anti-IL-17A antibodies (e.g., secukinumab);
  mTOR inhibitors (e.g., sirolimus);
  VGX-1027;
  JAK3 inhibitors (e.g., tofacitinib or R348); and
  protein kinase C inhibitors (e.g. AEB-071).

Hence another aspect of the invention provides a compound of formula (I) in combination with one or more further active ingredients, for example one or more active ingredients described above.

Similarly, another aspect of the invention provides a combination product comprising:

(A) a compound of the present invention (i.e. a compound of formula (I), (Ia1), (Ia2), (Ib1), (Ib2), (Ic1), (Ic2), (Id1), (Id2), (Ie1), (Ie2), (If1), (If2), (Ig1), (Ig2), (Ih1) or (Ih2), as defined above, or a pharmaceutically acceptable salt thereof); and (B) another therapeutic agent, wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of the present invention in admixture with a pharmaceutically acceptable adjuvant, diluent or carrier; and
(ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The other therapeutic agent (i.e. component (B) above) may be, for example, any of the agents mentioned above in connection with the treatment of respiratory, gastrointestinal and eye disorders.

The combination product (either a combined preparation or kit-of-parts) of this aspect of the invention may be used in the treatment or prevention of an inflammatory disease (e.g. the inflammatory diseases mentioned above, such as:
respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema);
eye diseases or disorders including allergic conjunctivitis, conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation or, particularly, uveitis (including posterior, anterior and pan uveitis), corneal graft and limbal cell transplant rejection;
skin diseases or disorders including allergic dermatitis, contact dermatitis, atopic dermatitis or psoriasis; and
gastrointestinal diseases or disorders including gluten sensitive enteropathy (coeliac disease), eosinophilic esophagitis, intestinal graft versus host disease or, particularly, ulcerative colitis or Crohn's disease.

The aspects of the invention described herein (e.g. the above-mentioned compound, combinations, methods and uses) may have the advantage that, in the treatment of the conditions described herein, they may be more convenient for the physician and/or patient than, be more efficacious than, be less toxic than, be longer acting than, have better selectivity over, have a broader range of activity than, be more potent than, produce fewer side effects than, have a better pharmacokinetic and/or pharmacodynamic profile than, have more suitable solid state morphology than, have better stability than, or may have other useful pharmacological properties over, similar compounds, combinations, methods (treatments) or uses known in the prior art for use in the treatment of those conditions or otherwise.

Relative to compounds of the prior art, the compounds of formula (I) may additionally (or alternatively):
exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma);
have a reduced risk of extravascular exposure following intravenous administration (e.g. due to a low volume of distribution for the compounds of formula (I));
exhibit superior potency with respect to selected kinases (e.g. Syk and/or a panel of kinases, such as Syk, Src and p38 MAPKα);
exhibit reduced β-catenin induction and/or inhibition of mitosis in cells;
exhibit no or less time-dependent inhibition of members of the cytochrome P450 superfamily; and/or
produce less problematic (e.g. less toxic) metabolites, e.g. following administration to a patient.

Experimental Section

Abbreviations used herein are defined below (Table 1). Any abbreviations not defined are intended to convey their generally accepted meaning.

TABLE 1

| | Abbreviations |
|---|---|
| AcOH | glacial acetic acid |
| aq | aqueous |
| ATP | adenosine-5'-triphosphate |
| BALF | bronchoalveolar lavage fluid |
| br | broad |
| BSA | bovine serum albumin |
| CatCart ® | catalytic cartridge |
| CDI | 1,1-carbonyl-diimidazole |
| COPD | chronic obstructive pulmonary disease |
| c-Src | cellular sarc(oma) kinase |
| d | doublet |
| DCM | dichloromethane |
| DMEM | Dulbecco's Modified Eagle Medium |
| DMSO | dimethyl sulfoxide |
| DSS | dextran sodium sulphate |
| d-U937 cells | PMA differentiated U-937 cells |
| (ES$^+$) | electrospray ionization, positive mode |
| Et | ethyl |
| EtOAc | ethyl acetate |
| FCS | foetal calf serum |
| FRET | fluorescence resonance energy transfer |
| GR | glucocorticoid receptor |
| GSK3α | glycogen synthase kinase 3α |
| HBEC | primary human bronchial epithelial cells |
| hr | hour(s) |
| HRP | horseradish peroxidise |
| HRV | human rhinovirus |
| IBD | inflammatory bowel disease |
| ICAM-1 | inter-cellular adhesion molecule 1 |
| IL-8 | interleukin 8 |
| JNK | c-Jun N-terminal kinase |
| LPS | lipopolysaccharide |
| (M + H)$^+$ | protonated molecular ion |
| MAPK | mitogen-activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| MMAD | mass median aerodynamic diameter |
| MOI | multiplicity of infection |
| min | minute(s) |
| MPO | myeloperoxidase |
| MTT | 3-(4,5-dimethylthiazol-2-yl)-2,5-diphenyltetrazolium bromide |
| m/z: | mass-to-charge ratio |
| NMR | nuclear magnetic resonance (spectroscopy) |
| NT | Not tested |
| PBMC | peripheral blood mononuclear cell |
| PBS | phosphate buffered saline |
| PG | protective group |
| Ph | phenyl |

TABLE 1-continued

Abbreviations

| | |
|---|---|
| PHA | phytohaemagglutinin |
| PMA | phorbol myristate acetate |
| p-TSA | 4-methylbenzenesulfonic acid |
| q | quartet |
| RT | room temperature |
| RP HPLC | reverse phase high performance liquid chromatography |
| RSV | respiratory syncytial virus |
| s | singlet |
| sat | saturated |
| SCX | solid supported cation exchange (resin) |
| SDS | sodium dodecyl sulphate |
| SNAr | nucleophilic aromatic substitution |
| Syk | spleen tyrosine kinase |
| t | triplet |
| T3P | 1-propanephosphonic acid cyclic anhydride |
| TBDMS | tert-butyldimethylsilyl |
| TCID$_{50}$ | 50% tissue culture infectious dose |
| THF | tetrahydrofuran |
| TMB | 3,3',5,5'-tetramethylbenzidine |
| TNBS | 2,4,6-trinitrobenzenesulfonic acid |
| TNFα | tumor necrosis factor alpha |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M NH$_3$ in MeOH.

Preparative Reverse Phase High Performance Liquid Chromatography

Agilent Scalar column C18, 5 μm (21.2×50 mm), flow rate 28 mL min$^{-1}$ eluting with a H$_2$O-MeCN gradient containing 0.1% v/v formic acid over 10 min using UV detection at 215 and 254 nm. Gradient information: 0.0-0.5 min; 95% H$_2$O-5% MeCN; 0.5-7.0 min; ramped from 95% H$_2$O-5% MeCN to 5% H$_2$O-95% MeCN; 7.0-7.9 min; held at 5% H$_2$O-95% MeCN; 7.9-8.0 min; returned to 95% H$_2$O-5% MeCN; 8.0-10.0 min; held at 95% H$_2$O-5% MeCN.

Analytical Methods

Reverse Phase High Performance Liquid Chromatography

Method 1:

Agilent Scalar column C18, 5 μm (4.6×50 mm) or Waters XBridge C18, 5 μm (4.6×50 mm) flow rate 2.5 mL min$^{-1}$ eluted with a H$_2$O-MeCN gradient containing either 0.1% v/v formic acid (Method 1 acidic) or NH$_3$ (Method 1 basic) over 7 min employing UV detection at 215 and 254 nm. Gradient information: 0.0-0.1 min, 95% H$_2$O-5% MeCN; 0.1-5.0 min, ramped from 95% H$_2$O-5% MeCN to 5% H$_2$O-95% MeCN; 5.0-5.5 min, held at 5% H$_2$O-95% MeCN; 5.5-5.6 min, held at 5% H$_2$O-95% MeCN, flow rate increased to 3.5 mL min$^{-1}$; 5.6-6.6 min, held at 5% H$_2$O-95% MeCN, flow rate 3.5 mL min$^{-1}$; 6.6-6.75 min, returned to 95% H$_2$O-5% MeCN, flow rate 3.5 mL min$^{-1}$; 6.75-6.9 min, held at 95% H$_2$O-5% MeCN, flow rate 3.5 mL·min$^{-1}$; 6.9-7.0 min, held at 95% H$_2$O-5% MeCN, flow rate reduced to 2.5 mL min$^{-1}$.

Method 2:

Agilent Extend C18 column, 1.8 μm (4.6×30 mm) at 40° C.; flow rate 2.5-4.5 mL min$^{-1}$ eluted with a H$_2$O-MeCN gradient containing either 0.1% v/v formic acid (Method 2 acidic) or NH$_3$ (Method 2 basic) over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

Method 3:

Waters Xselect CSH C18 3.5 μm (4.6×50 mm) flow rate 2.5 mL min$^{-1}$ eluted with a H$_2$O-MeCN gradient containing 0.1% v/v formic acid over 7 min employing UV detection at 215 and 254 nm. Gradient information: 0.0-0.1 min, 95% H$_2$O-5% MeCN; 0.1-5.0 min, ramped from 95% H$_2$O-5% MeCN to 5% H$_2$O-95% MeCN; 5.0-5.5 min, held at 5% H$_2$O-95% MeCN; 5.5-5.6 min, held at 5% H$_2$O-95% MeCN, flow rate increased to 3.5 mL min$^{-1}$; 5.6-6.6 min, held at 5% H$_2$O-95% MeCN, flow rate 3.5 mL min$^{-1}$; 6.6-6.75 min, returned to 95% H$_2$O-5% MeCN, flow rate 3.5 mL min$^{-1}$; 6.75-6.9 min, held at 95% H$_2$O-5% MeCN, flow rate 3.5 mL·min$^{-1}$; 6.9-7.0 min, held at 95% H$_2$O-5% MeCN, flow rate reduced to 2.5 mL min$^{-1}$.

Method 4:

Waters Xselect CSH C18 3.5 μm (4.6×50 mm); flow rate 2.5-4.5 mL min$^{-1}$ eluted with a H$_2$O-MeCN gradient containing 0.1% v/v formic acid over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01 3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

Those intermediates, used to prepare compound examples of the invention, that have been previously disclosed were obtained using the procedures contained in the references cited below (Table 2). Additional intermediates were prepared by the representative synthetic processes described herein.

TABLE 2

| | Compound Intermediates | |
|---|---|---|
| No. | Structure | Name, LCMS Data and Reference |
| A1 | | 3-tert-butyl-1-p-tolyl-1H-pyrazol-5-amine. R$^t$ 2.46 min (Method 1 basic); m/z 230 (M + H)$^+$, (ES$^+$). Cirillo, P. F. et al., WO 2000/43384, 27 Jul 2000. |
| A1* | | phenyl (3-(tert-butyl)-1-(p-tolyl)-1H-pyrazol-5-yl)carbamate LCMS m/z 350 (M + H)$^+$ (ES$^+$); 348 (M − H)$^−$ (ES$^−$) Kapadia, S. R. et al., U.S. Pat. No. 6,492,529, 10 Dec 2002. |
| A2 | | 3-isopropyl-1-(p-tolyl)-1H-pyrazol-5-amine. R$^t$ 3.14 min (Method 1, acidic, X-Select); m/z 216 (M + H)$^+$, (ES$^+$). Ito, K. et al., WO 2010/067130, 17 Jun 2010. |
| A3 | | 3-tert-butyl-1-(4-methoxyphenyl)-1H-pyrazol-5-amine. R$^t$ 1.32 min (Method 2, acidic); m/z 246 (M + H)$^+$, (ES$^+$). Mathias, J. P. et al., US 2006/0035922, 10 Aug 2005. |
| A3* | | phenyl (3-(tert-butyl)-1-(4-methoxyphenyl)-1H-pyrazol-5-yl)carbamate LCMS m/z 366 (M + H)$^+$ (ES$^+$); 364 (M − H)$^−$ (ES$^−$) Abraham, S. et al., WO 2009/117080, 24 Sep 2009. |

TABLE 2-continued

Compound Intermediates

| No. | Structure | Name, LCMS Data and Reference |
|---|---|---|
| A4 | *tBu* group on pyrazole; N-phenyl with D,D,D,D and CD₃ substitutions; NH₂ | 3-tert-butyl-1-(2,3,5,6-tetradeutero-4-(trideuteromethyl)phenyl)-1H-pyrazole-5-amine<br>m/z 237 (M + H)⁺, (ES⁺).<br>Ito, K. et al., WO 2010/067130, 17 Jun 2010 |
| G1 | Naphthalene with H₂N and O-linked chloropyridine | 4-((2-chloropyrimidin-4-yl)oxy)naphthalen-1-amine.<br>R$^t$ 3.13 min (Method 3); m/z 271/273 (M + H)⁺, (ES⁺).<br>Ito, K. et al., WO 2010/112936, 07 Oct 2010 |
| G2 | Naphthalene with H₂N and O-linked chloropyrimidine | 4-((2-chloropyrimidin-4-yl)oxy)naphthalen-1-amine.<br>R$^t$ 1.80 min (Method 2, acidic); m/z 272/274 (M + H)⁺, (ES⁺).<br>Cirillo, P. F. et al., WO 2002/92576, 21 Nov 2000. |
| G2(P) | Naphthalene with BocHN and O-linked chloropyrimidine | tert-butyl (4-((2-chloropyrimidin-4-yl)oxy)naphthalen-1-yl)carbamate.<br>R$^t$ 2.43 min (Method 2, acidic); m/z 372/374 (M + H)⁺, (ES⁺).<br>Ito, K. et al., WO 2010/067130, 17 Jun 2010 |

Intermediate A4*: Phenyl (3-(tert-butyl)-1-(2,3,5,6-tetradeutero-4-(trideuteromethyl)-phenyl)-1H-pyrazol-5-yl)carbamate

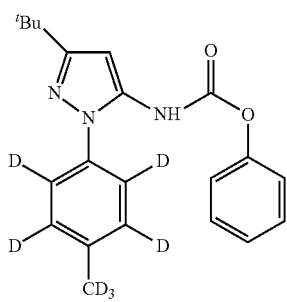 [SMILES: [2H]c1c([2H])c(C([2H])([2H])[2H])c([2H])c([2H])c1-n1nc(C(C)(C)C)cc1NC(=O)Oc1ccccc1]

Phenyl chloroformate (580 µL, 4.62 mmol) was added to a stirred mixture of Intermediate A4 (1 g, 4.23 mmol) and NaHCO₃ (0.711 g, 8.46 mmol) in DCM (20 mL) and THF (10 mL). The mixture was stirred for 3 h then partitioned between DCM (200 mL) and water (100 mL). The organic layer was separated, washed with brine, dried (MgSO₄), filtered and evaporated under reduced pressure. The residue was triturated with ether/isohexane, filtered and dried to afford the sub-title compound (1.335 g)

LCMS m/z 357 (M+H)⁺ (ES⁺); 355 (M−H)⁻ (ES⁻)

Intermediate A5: 3-(tert-Butyl)-1-(4-(dimethylamino)phenyl)-1H-pyrazol-5-amine

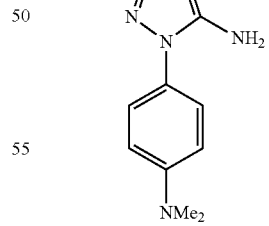

DPPA (0.550 mL, 2.55 mmol) was added to a stirred solution of Intermediate M1 (500 mg, 1.740 mmol) and Et₃N (0.4 mL, 2.87 mmol) in tert-butanol (10 ml) under N₂ then heated to reflux for 18 h. The mixture was cooled, water (75 mL) added and extracted with ethyl acetate (3×50 mL). The combined organic phases were washed with saturated brine (50 mL), dried (MgSO₄) and concentrated under reduced pressure. The crude product was purified by chromatography on the Companion (40 g column, 25-100% DCM:iso-hexane) to afford tert-butyl (3-(tert-butyl)-1-(4-(dimethylamino)phenyl)-1H-pyrazol-5-yl)carbamate (459 mg) as a pale orange oil.

LCMS m/z 359 (M+H)+ (ES+); 357 (M−H)− (ES−)

TFA (1 mL, 12.98 mmol) was added to a stirred solution of (3-(tert-butyl)-1-(4-(dimethylamino)phenyl)-1H-pyrazol-5-yl)carbamate obtained immediately above (459 mg, 1.280 mmol) in DCM (5 mL) at rt for 3 h. The mixture was concentrated under reduced pressure and the residue was redissolved in ethyl acetate (25 mL). The organic solution was washed with saturated NaHCO₃ solution (2×25 mL), saturated brine (25 mL), dried (MgSO₄) and concentrated under reduced pressure to yield Intermediate A5 (335 mg).

LCMS m/z 259 (M+H)+ (ES+)

Intermediate A5*: Phenyl (3-(tert-butyl)-1-(4-(dimethylamino)phenyl)-1H-pyrazol-5-yl)carbamate

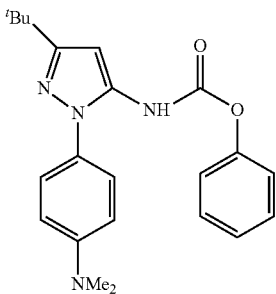 [SMILES: CN(C)c1ccc(-n2nc(C(C)(C)C)cc2NC(=O)Oc2ccccc2)cc1]

Phenyl chloroformate (175 μL, 1.395 mmol) was added to a suspension of Intermediate A5 (335 mg, 1.297 mmol) and NaHCO₃ (220 mg, 2.62 mmol) in THF (4 mL) and DCM (4 mL). The mixture was stirred at rt for 2 h. The mixture was diluted with DCM (20 mL) and washed with water (25 mL). The organic phase was washed with saturated brine (20 mL), dried (MgSO₄) and concentrated under reduced pressure. The residue was recrystallised in cyclohexane to afford the sub-title compound (345 mg) as a white solid.

¹H NMR (CDCl₃) 400 MHz, δ: 7.44-7.31 (m, 4H), 7.29-7.22 (m, 1H), 7.21-7.11 (m, 2H), 7.03-6.90 (m, 1H), 6.90-6.76 (m, 2H), 6.56-6.36 (m, 1H), 3.04 (s, 6H), 1.37 (s, 9H).

LCMS m/z 379 (M+H)+ (ES+)

Intermediate B1: 3-((4-((4-Aminonaphthalen-1-yl)oxy)pyridin-2-yl)amino)-5-methoxy-N-(2-(2-(2-methoxyethoxy)ethoxy)ethyl)benzamide

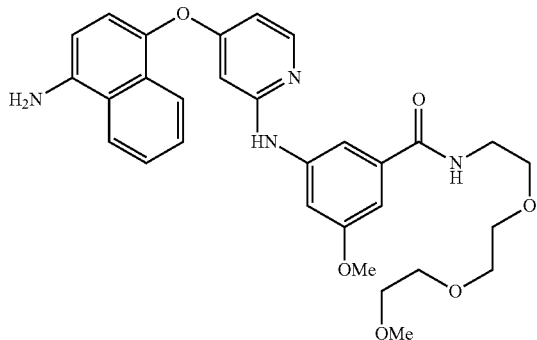 [SMILES: COCCOCCOCCNC(=O)c1cc(Nc2cc(Oc3ccc(N)c4ccccc34)ccn2)cc(OC)c1]

Pd₂dba₃ (22 mg, 0.024 mmol) and BINAP (30 mg, 0.048 mmol) were stirred in 1,4-dioxane (1 mL) for 10 minutes under N₂. In a separate vessel, purged with N₂, caesium carbonate (455 mg, 1.396 mmol), Intermediate D3 (291 mg, 0.930 mmol) and Intermediate G1(P) (345 mg, 0.930 mmol) were stirred in 1,4-dioxane (5 mL). The catalyst solution was added to the main reaction mixture and the whole was heated to 90° C. for 18 h. Upon cooling, the mixture was diluted with water (40 mL) and extracted with ethyl acetate (3×25 mL). The combined organic phases were washed with saturated brine (15 mL), dried (MgSO₄) and concentrated under reduced pressure. The crude product was purified by chromatography on the Companion (40 g column, 0-50% acetone/ethyl acetate) to afford tert-butyl (4-((2-((3-methoxy-5-((2-(2-(2-methoxyethoxy)ethoxy)ethyl)carbamoyl)phenyl)amino)pyridin-4-yl)oxy)-naphthalen-1-yl)carbamate (Intermediate B1(P), 320 mg) as a sticky orange oil.

¹H NMR (DMSO-d6) 400 MHz, δ: 9.37 (s, 1H), 9.09 (s, 1H), 8.35 (t, 1H), 8.17-8.05 (m, 2H), 7.83 (d, 1H), 7.67-7.46 (m, 5H), 7.35 (d, 1H), 6.88 (s, 1H), 6.57 (dd, 1H), 6.09 (d, 1H), 3.74 (s, 3H), 3.58-3.44 (m, 8H), 3.44-3.34 (m, 4H), 3.20 (s, 3H), 1.52 (s, 9H).

LCMS m/z 647 (M+H)+ (ES+); 645 (M−H)− (ES−)

A solution of Intermediate B1(P) (320 mg, 0.495 mmol) in DCM (1 mL) was treated with TFA (1000 μL, 12.98 mmol) and stirred at rt for 3 h. The mixture was diluted with water (10 mL) and DCM (10 mL). The mixture was neutralised with saturated NaHCO₃ and passed through a phase separation cartridge. The organic phase was dried (MgSO₄) and concentrated to give Intermediate B1 (270 mg) as a brown gum.

¹H NMR (DMSO-d6) 400 MHz, δ: 9.00 (s, 1H), 8.34 (dd, 1H), 8.20-8.10 (m, 1H), 8.05 (d, 1H), 7.67-7.60 (m, 1H), 7.59-7.55 (m, 1H), 7.52-7.47 (m, 1H), 7.47-7.41 (m, 2H), 7.10 (d, 1H), 6.89-6.84 (m, 1H), 6.71 (d, 1H), 6.51 (dd, 1H), 6.05 (d, 1H), 5.83 (s, 2H), 3.73 (S, 3H), 3.58-3.45 (m, 8H), 3.45-3.35 (m, 4H), 3.21 (s, 3H).

LCMS m/z 547 (M+H)+ (ES+)

Intermediate B2: 3-((4-((4-Aminonaphthalen-1-yl)oxy)pyrimidin-2-yl)amino)-5-ethynyl-N-(2-(2-(2-methoxyethoxy)ethoxy)ethyl)benzamide

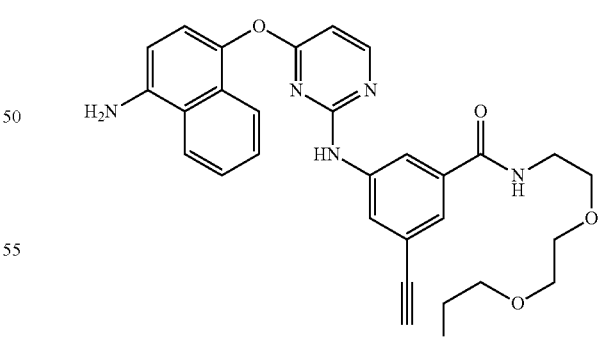

Method 1

T3P, 50% w/w in EtOAc (54.0 ml, 91 mmol) was added to a solution Intermediate J1(P) (30 g, 60.4 mmol), 2-(2-(2-methoxyethoxy)ethoxy)ethanamine (11.83 g, 72.5 mmol), and TEA (20 mL, 143 mmol) in DMF (400 mL). The mixture was stirred at rt for 18 h. The mixture was diluted with water (700 mL) and saturated sodium hydrogen carbonate solution (500 mL) and the mixture was extracted with ethyl acetate (3×400 mL). The combined organic phases were washed with 20% brine (3×500 mL), saturated brine (3×500 mL), dried (MgSO$_4$), filtered and concentrated in vacuo. The crude product was purified in two batches by chromatography on the companion (330 g column, 1-5% MeOH in DCM) to afford tert-butyl (4-((2-((3-ethynyl-5-((2-(2-(2-methoxyethoxy)ethoxy)ethyl)carbamoyl)phenyl)amino)-pyrimidin-4-yl)oxy)naphthalen-1-yl)carbamate (Intermediate B2(P), 24.4 g) as a pale yellow foam.

$^1$H NMR (400 MHz, DMSO-d6) δ: 9.74 (s, 1H), 9.31 (s, 1H), 8.44-8.47 (m, 2H), 8.11 (s, 1H), 8.10 (d, 1H), 7.91 (s, 1H), 7.82 (d, 1H), 7.54-7.63 (m, 3H), 7.46 (s, 1H), 7.42 (d, 1H), 6.58 (d, 1H), 4.15 (s, 1H), 3.49-3.53 (m, 8H), 3.36-3.41 (m, 4H), 3.21 (s, 3H), 1.52 (s, 9H).

LCMS m/z 642 (M+H)$^+$ (ES$^+$); 640 (M−H)$^−$ (ES$^−$)

Trifluoroacetic acid (30 ml, 389 mmol) was added dropwise to a stirred solution of Intermediate B2(P) (12.0 g, 18.70 mmol) in DCM (200 mL). The reaction was stirred at rt for 3 h. The reaction was concentrated in vacuo and the residue partitioned between DCM (300 mL) and saturated NaHCO$_3$ solution (400 mL). The aqueous phase was separated and extracted with DCM (200 mL). The combined organics were dried (MgSO$_4$), filtered and concentrated in vacuo to give a beige foam. The crude product was purified by chromatography on the Companion (220 g column, 1-5% MeOH in DCM) to afford Intermediate B2 (9.0 g) as a pale pink foam.

$^1$H NMR (400 MHz, DMSO-d6) δ: 9.74 (s, 1H), 8.46 (t, 1H), 8.36 (d, 1H), 8.12-8.14 (m, 1H), 8.07 (s, 1H), 7.94 (s, 1H), 7.62-7.64 (m, 1H), 7.41-7.46 (m, 3H), 7.15 (d, 1H), 6.70 (d, 1H), 6.38 (d, 1H), 5.76 (s, 2H), 4.18 (s, 1H), 3.49-3.53 (m, 8H), 3.36-3.41 (m, 4H), 3.21 (s, 3H).

LCMS m/z 542 (M+H)$^+$ (ES$^+$); 540 (M−H)$^−$ (ES$^−$)

Method 2

A mixture of Intermediate D2 (155.76 g of approx. 90% purity, 458 mmol), Intermediate G2(P) (166.6 g, 448 mmol) and para-toluenesulfonic acid (14.7 g, 85 mmol) in THF (2.5 L) was heated at reflux for 6 h. The reaction mixture was then allowed to cool overnight to provide a dark brown mixture having a "jelly" consistency. Solvent was evaporated to provide a viscous, tacky material. This was dissolved in mixture of ethyl acetate and sodium bicarbonate (aqueous). The aqueous and organic layers were separated and the aqueous layer was re-extracted with ethyl acetate. The combined ethyl acetate layers were washed with brine (×2) before being dried (MgSO$_4$), filtered through a silica plug, reduced (by solvent evaporation) to approx 10% volume and then poured onto a large excess of n-hexane. The resulting mixture was stirred for 6-8 h to provide a solid that was isolated by filtration, washed with n-hexane and then dried to afford a pale brown solid (Intermediate B2(P), 223 g, 77.5%).

Washing of the silica plug with acetone yielded a further 42 g (14.6%) of mixture of Intermediate B2(P) and Intermediate B2, as determined by TLC.

The two solid materials comprising or containing Intermediate B2(P) were combined and then used in the next stage without any further purification.

A mixture of Intermediate B2(P) (265 g, 413 mmol), trifluoroacetic acid (575.62 g, 5.048 mol) and dichloromethane (2 L) was stirred together for 3 h. Analysis by TLC (ethyl acetate) showed complete consumption of starting material. The solvent was reduced by evaporation and the resulting residue dissolved in ethyl acetate. The organic solution was cautiously washed with sodium bicarbonate (saturated, aq.) before being dried (MgSO$_4$), filtered and then concentrated in vacuo to afford Intermediate B2 as a black gum/foam (200 g, 89.4%) that had $^1$H NMR and LCMS data essentially identical to those of the material obtained via Method 1 above, and which gum/foam was used in the next step without further purification.

Intermediate B3: 3-((4-((4-Aminonaphthalen-1-yl)oxy)pyrimidin-2-yl)amino)-5-ethynyl-N-(2,5,8,11-tetraoxatridecan-13-yl)benzamide

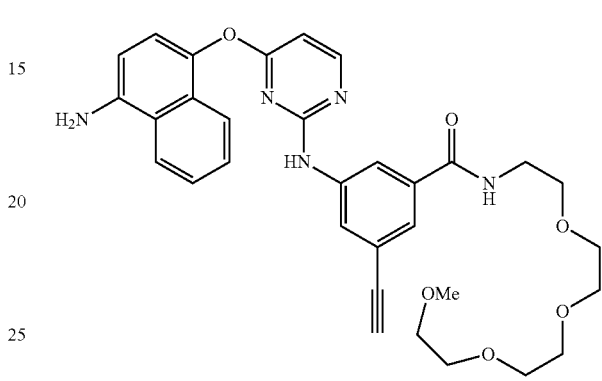

T3P (50% w/w in EtOAc, 1.80 ml, 3.02 mmol) was added to a solution of Intermediate J1(P) (1 g, 2.014 mmol), 2,5,8,11-tetraoxatridecan-13-amine (0.501 g, 2.417 mmol), and Et$_3$N (0.70 mL, 5.02 mmol) in DMF (15 mL). The reaction was stirred at rt for 18 h. The mixture was diluted with water (200 mL) and saturated aqueous NaHCO$_3$ solution (100 mL) and the aqueous phase extracted with EtOAc (3×100 mL). The combined organic phases were washed with 20% brine (3×100 mL), saturated brine (3×100 mL), then dried (MgSO$_4$), filtered and concentrated in vacuo affording a brown foam. The crude product was purified by chromatography on silica gel (40 g column, 1-5% MeOH in DCM) to afford the sub-title compound tert-butyl (4-((2-((3-((2,5,8,11-tetraoxatridecan-13-yl)carbamoyl)-5-ethynylphenyl)-amino)pyrimidin-4-yl)oxy)naphthalen-1-yl)carbamate (Intermediate B3(P), 940 mg) as an off-white foam.

LCMS m/z 686 (M+H)$^+$ (ES$^+$); 684 (M−H)$^−$ (ES$^−$)

Trifluoroacetic acid (2000 µL, 26.0 mmol) was added dropwise to a stirred solution of Intermediate B3(P) (940 mg, 1.371 mmol) in DCM (20 ml). The reaction was stirred at rt overnight. The reaction was concentrated in vacuo and the residue partitioned between DCM (30 mL) and saturated aqueous NaHCO$_3$ solution (100 mL). The aqueous phase was extracted with DCM (20 mL). The combined organics were dried (MgSO$_4$), filtered and concentrated in vacuo onto silica gel. The crude product was purified by chromatography (40 g column, 3-5% MeOH in DCM) to afford the sub-title compound (670 mg) as a pale yellow oil which became foam-like on drying at 40° C. under vacuum for 2 h.

$^1$H NMR (400 MHz, DMSO-d6) δ: 9.74 (s, 1H), 8.46 (t, 1H), 8.36 (d, 1H), 8.12-8.14 (m, 1H), 8.07 (s, 1H), 7.94 (s, 1H), 7.62-7.64 (m, 1H), 7.41-7.46 (m, 3H), 7.14 (d, 1H), 6.70 (d, 1H), 6.37 (d, 1H), 5.76 (s, 2H), 4.17 (s, 1H), 3.47-3.53 (m, 12H), 3.36-3.41 (m, 4H), 3.22 (s, 3H).

LCMS m/z 586 (M+H)$^+$ (ES$^+$); 584 (M−H)$^−$ (ES$^−$)

Intermediate B4: 3-((4-((4-Aminonaphthalen-1-yl)oxy)pyrimidin-2-yl)amino)-5-ethynyl-N-(2-(2-methoxyethoxy)ethyl)benzamide

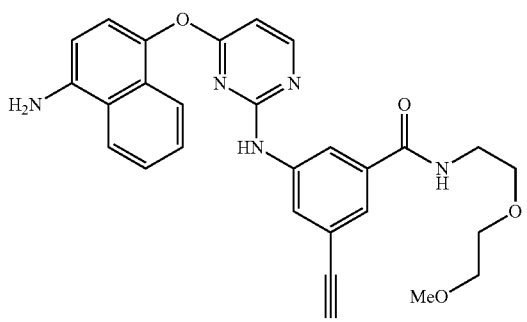 [SMILES: C#Cc1cc(Nc2nccc(Oc3ccc(N)c4ccccc34)n2)cc(C(=O)NCCOCCOC)c1]

HATU (842 mg, 2.215 mmol) was added to a stirred solution of Intermediate J1(P) (1000 mg, 2.014 mmol), 2-(2-methoxyethoxy)ethanamine (360 mg, 3.02 mmol) and Hunig's Base (1000 µL, 5.73 mmol) in DMF (10 mL) at rt. The mixture was stirred for 3 h then added to a vigorously stirred solution of 0.1 M hydrogen chloride (200 mL). The resulting precipitate was collected by filtration and washed with water (20 mL) to yield the crude product as a tan solid. The solid was purified by chromatography on silica gel (40 g column, 0-20% Acetone/EtOAc) to afford tert-butyl (4-((2-((3-ethynyl-5-((2-(2-methoxyethoxy)ethyl)-carbamoyl)phenyl)amino)pyrimidin-4-yl)oxy)naphthalen-1-yl)carbamate (Intermediate B4(P), 895 mg) as a yellow foam.

$^1$H NMR (400 MHz, DMSO-d6) δ 9.75 (s, 1H), 9.31 (s, 1H), 8.53-8.40 (m, 1H), 8.45 (d, 1H), 8.17-8.06 (m, 2H), 7.95-7.87 (m, 1H), 7.87-7.77 (m, 1H), 7.65-7.52 (m, 3H), 7.46 (d, 1H), 7.42 (d, 1H), 6.57 (d, 1H), 4.15 (s, 1H), 3.58-3.47 (m, 4H), 3.47-3.35 (m, 4H), 3.23 (s, 3H), 1.52 (s, 9H).

LCMS m/z 598 (M+H)$^+$ (ES$^+$); 596 (M−H)$^-$ (ES$^-$)

Trifluoroacetic acid (1.000 mL, 12.98 mmol) was added dropwise to a stirred solution of Intermediate B4(P) (0.895 g, 1.498 mmol) in DCM (8 mL). The reaction was stirred at rt for 18 h. The solvents were evaporated and the residue partitioned between EtOAc (50 mL) and sat. NaHCO$_3$ soln. (50 ml), the organic phase was washed with saturated brine (50 ml). The organics were bulked, dried, filtered and evaporated to give a pale brown foam. The foam was purified by chromatography on silica gel (12 g column, EtOAc) to afford Intermediate B4 (700 mg) as a light beige foam.

$^1$H NMR (400 MHz, DMSO-d6) δ 9.74 (s, 1H), 8.45 (dd, 1H), 8.36 (d, 1H), 8.17-8.10 (m, 1H), 8.10-8.03 (m, 1H), 7.97-7.90 (m, 1H), 7.67-7.59 (m, 1H), 7.48-7.38 (m, 3H), 7.15 (d, 1H), 6.70 (d, 1H), 6.37 (d, 1H), 5.81-5.71 (m, 2H), 4.18 (s, 1H), 3.57-3.47 (m, 4H), 3.47-3.34 (m, 4H), 3.23 (s, 3H).

LCMS m/z 498 (M+H)$^+$ (ES$^+$); 496 (M−H)$^-$ (ES$^-$)

Intermediate B5: 3-((4-((4-Aminonaphthalen-1-yl)oxy)pyridin-2-yl)amino)-5-ethynyl-N-(2-(2-(2-methoxyethoxy)ethoxy)ethyl)benzamide

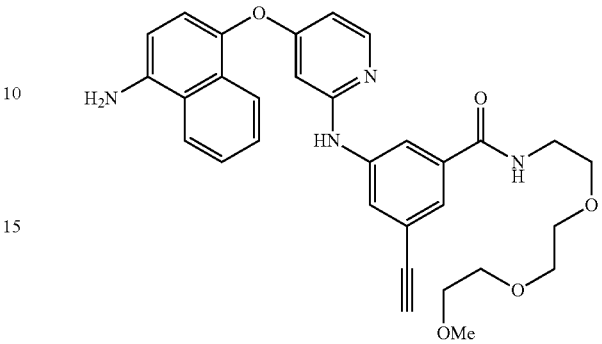

HATU (500 mg, 1.315 mmol) was added to a stirred solution of Intermediate J2(P) (500 mg, 1.009 mmol), 2-(2-(2-methoxyethoxy)ethoxy)ethanamine (277 mg, 1.695 mmol) and Et$_3$N (250 µL, 1.796 mmol) in DMF (10 mL). The mixture was stirred at rt for 18 h. The mixture was diluted with ethyl acetate (50 mL) and washed with water (50 mL), 20% brine (3×50 mL) and saturated brine (50 mL). The organic phase was dried (MgSO$_4$), filtered and concentrated under reduced pressure. The crude product was purified by chromatography on the Companion (40 g column, EtOAc) to afford tert-butyl (4-((2-((3-ethynyl-5-((2-(2-(2-methoxyethoxy)ethoxy)ethyl)carbamoyl)phenyl)amino)pyridin-4-yl)oxy)naphthalen-1-yl)carbamate (Intermediate B5(P), 580 mg) as a tan foam.

LCMS m/z 641 (M+H)$^+$ (ES$^+$); 639 (M−H)$^-$ (ES$^-$)

TFA (1 mL, 12.98 mmol) was added to a solution of Intermediate B5(P) (580 mg, 0.905 mmol) in DCM (5 mL) at rt and stirred overnight. The volatiles were removed under reduced pressure and the residue was redissolved in DCM (20 mL). The organic phase was washed with saturated NaHCO$_3$ solution (20 mL), dried (MgSO$_4$) and concentrated under reduced pressure to yield Intermediate B5 (475 mg).

LCMS m/z 541 (M+H)$^+$ (ES$^+$); 539 (M−H)$^-$ (ES$^-$)

Intermediate B6: 3-((4-((4-Aminonaphthalen-1-yl)oxy)pyrimidin-2-yl)amino)-5-methoxy-N-(2-(2-(2-methoxyethoxy)ethoxy)ethyl)benzamide

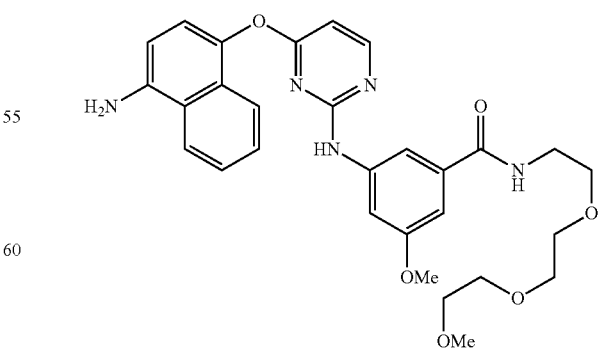

HATU (425 mg, 1.118 mmol) was added to a stirred solution of Intermediate J3(P) (500 mg, 0.995 mmol), 2-(2-

(2-methoxyethoxy)ethoxy)ethanamine (250 mg, 1.532 mmol) and Hunig's Base (500 μl, 2.86 mmol) in DMF (10 ml) at rt. The mixture was stirred for 1 h then partitioned between 10% aq brine (100 ml) and EtOAc (100 ml). The organic layer was washed with sat aq NaHCO₃ soln (50 ml), 0.5M HCl (50 ml), 10% aq brine (50 ml), dried (MgSO₄), filtered and evaporated under reduced pressure to afford tert-butyl (4-((2-((3-methoxy-5-((2-(2-(2-methoxyethoxy) ethoxy)ethyl)carbamoyl)phenyl)amino)pyrimidin-4-yl)oxy) naphthalen-1-yl)carbamate (Intermediate B6(P), 532 mg) as a white foam.

LCMS m/z 648 (M+H)⁺ (ES⁺); 646 (M−H)⁻ (ES⁻)

TFA (1.5 mL, 19.47 mmol) was added to a solution of Intermediate B6(P) (530 mg, 0.818 mmol) in DCM (5 mL) and the mixture was stirred at rt for 35 minutes. The mixture was diluted with toluene (100 mL) and concentrated under reduced pressure. The residue was redissolved in DCM (20 mL) and washed with saturated NaHCO₃ solution (20 mL) followed by saturated brine (20 mL). The organic phase was dried (MgSO₄) and concentrated under reduced pressure to yield Intermediate B6 (440 mg) as a brown foam.

LCMS m/z 548 (M+H)⁺ (ES⁺); 546 (M−H)⁻ (ES⁻)

Intermediate C1: 1-(4-(2-Chloropyrimidin-4-yloxy) naphthalen-1-yl)-3-(3-isopropyl-1-p-tolyl-1H-pyrazol-5-yl)urea

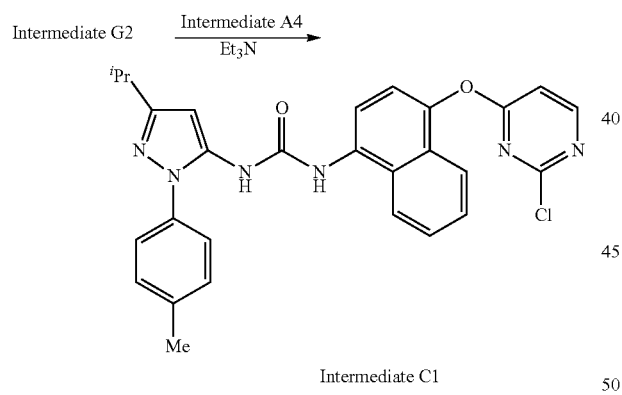

To a solution of Intermediate G2 (5.00 g, 18.4 mmol) in a mixture of isopropyl acetate (50 mL) and anhydrous THF (50 mL) was added portion-wise phenyl (3-isopropyl-1-(p-tolyl)-1H-pyrazol-5-yl)carbamate Intermediate A2* (7.72 g, 23.0 mmol) followed by triethylamine (0.64 mL, 4.6 mmol) and the reaction mixture maintained at RT for 18 hr. During this interval a thick purple precipitate formed which was collected by filtration and then washed with a mixture of isopropyl acetate and THF (1:1 v/v, 3×40 mL). The solid was purified by flash column chromatography (SiO₂, 330 g, 0-5% MeOH in DCM, gradient elution) to afford the title compound, Intermediate C1 as a pale purple solid (5.72 g, 47%); R^f 2.48 min (Method 4); m/z 513 (M+H)⁺ (ES⁺).

Intermediate C2: 1-(3-(tert-Butyl)-1-(p-tolyl)-1H-pyrazol-5-yl)-3-(4-((2-chloropyrimidin-4-yl)oxy) naphthalen-1-yl)urea

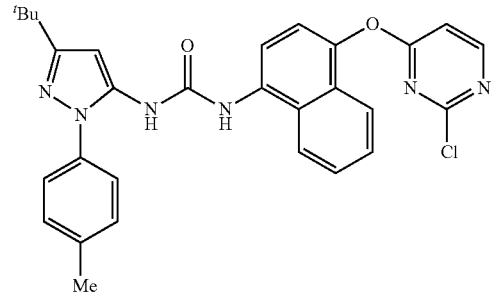 [SMILES: Cc1ccc(-n2nc(C(C)(C)C)cc2NC(=O)Nc2ccc(Oc3ccnc(Cl)n3)c3ccccc23)cc1]

A stirred suspension of Intermediate A1* (3 g, 8.59 mmol) and Intermediate G2 (2.333 g, 8.59 mmol) in isopropyl acetate (100 mL) was treated with triethylamine (0.3 mL, 2.152 mmol) and stirred at 60° C. (bath) for 1 h. The solution was diluted with ethyl acetate (300 mL), washed with water (2×100 mL) followed by brine (100 mL), was dried (Na₂SO₄) and evaporated. The residue was purified on a 220 g redisep silica cartridge using 5%, for 17 column volumes, and then 40% of acetone in toluene as eluent and then on another 220 g redisep silica cartridge using 0 to 3% MeOH/DCM as eluent to give Intermediate C2 (3.703 g) as a buff foam.

¹H NMR (400 MHz, DMSO-d6) δ 9.14 (s, 1H), 8.79 (s, 1H), 8.65 (d, 1H), 8.09 (d, 1H), 7.96 (d, 1H), 7.79 (d, 1H), 7.67-7.64 (m, 1H), 7.60-7.56 (m, 1H), 7.47-7.37 (m, 5H), 7.26 (d, 1H), 6.41 (s, 1H), 2.40 (s, 3H), 1.28 (s, 9H).

LCMS m/z 527/529 (M+H)⁺ (ES⁺)

Intermediate C3: 1-(3-(tert-Butyl)-1-(4-methoxyphenyl)-1H-pyrazol-5-yl)-3-(4-((2-chloropyrimidin-4-yl)oxy)naphthalen-1-yl)urea

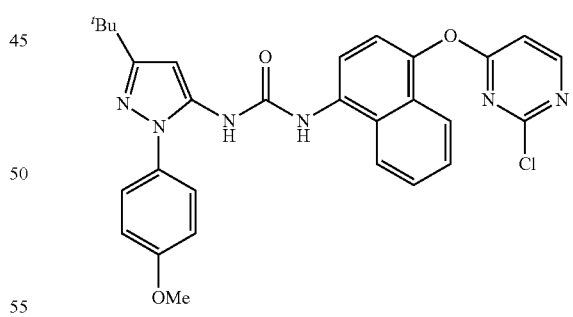

In a 100 mL flask, a solution of Intermediate A3* (1917 mg, 5.24 mmol) and Intermediate G2 (1500 mg, 5.24 mmol) in isopropyl acetate (58 mL) was treated with triethylamine (113 μL, 0.813 mmol). The resultant brown solution was heated at 70° C. for 2 h then the solvent removed in vacuo to afford a thick brown oil. The crude product was purified by chromatography on silica gel (120 g column, EtOAc 0-15% in DCM) to afford Intermediate C3 (2.169 g) as a white crystalline solid.

¹H NMR (400 MHz, DMSO-d6) δ 9.14 (s, 1H), 8.75 (s, 1H), 8.66 (d, 1H), 8.09 (d, 1H), 7.97 (d, 1H), 7.82-7.77 (m,

1H), 7.69-7.62 (m, 1H), 7.58 (ddd, 1H), 7.51-7.46 (m, 2H), 7.43 (d, 1H), 7.27 (d, 1H), 7.15-7.10 (m, 2H), 6.40 (s, 1H), 3.84 (s, 3H), 1.29 (s, 9H).

LCMS m/z 544 (M+H)+ (ES+)

Intermediate C4(H): 1-(3-(tert-Butyl)-1-(p-tolyl)-1H-pyrazol-5-yl)-3-(4-((2-chloropyrimidin-4-yl)oxy)-5,6,7,8-tetrahydronaphthalen-1-yl)urea

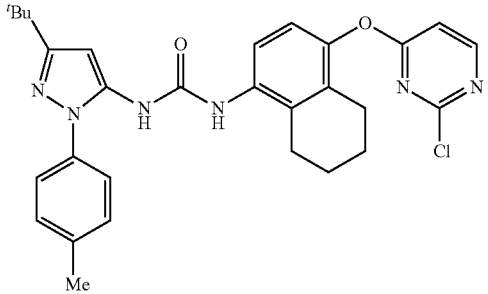 [SMILES: Cc1ccc(-n2nc(C(C)(C)C)cc2NC(=O)Nc2ccc(Oc3ccnc(Cl)n3)c3c2CCCC3)cc1]

A mixture of Intermediate A1* (760 mg, 2.176 mmol), Intermediate G3 (500 mg, 1.813 mmol) and Et₃N (80 µL, 0.574 mmol) in iPrOAc (15 mL) was heated at 60° C. for 1.5 h. The mixture was cooled, evaporated under reduced pressure and the residue purified by chromatography on silica gel (80 g column, 0-50% EtOAc/isohexane) to afford Intermediate C4(H) (807 mg) as a light brown foam.

¹H NMR (CDCl₃) 400 MHz, δ: 8.42 (d, 1H), 7.43 (d, 1H), 7.32 (d, 2H), 7.22 (d, 2H), 6.88 (d, 1H), 6.74 (d, 1H), 6.50 (s, 1H), 6.44 (s, 1H), 6.37 (s, 1H), 2.48 (t, 2H), 2.41 (t, 2H), 2.36 (s, 3H), 1.73-1.62 (m, 4H), 1.35 (s, 9H).

LCMS m/z 531/3 (M+H)+ (ES+)

Intermediate D1: 3-Amino-5-bromo-N-(2-(2-(2-methoxyethoxy)ethoxy)ethyl)benzamide

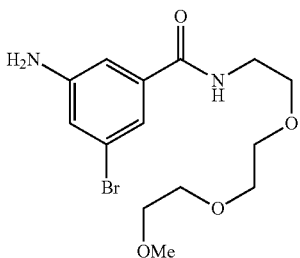 [SMILES: COCCOCCOCCNC(=O)c1cc(N)cc(Br)c1]

Method 1

T3P (1-propanephosphonic acid cyclic anhydride 50 wt % in EtOAc, 4.13 ml, 6.94 mmol) was added carefully to a solution of 3-amino-5-bromobenzoic acid (1 g, 4.63 mmol), 2-(2-(2-methoxyethoxy)ethoxy)ethanamine (1.022 ml, 6.13 mmol) and TEA (1.936 ml, 13.89 mmol) in DCM (20 mL). Ice bath used sporadically to prevent temperature rising above 35° C. Stirred at rt for 1 h then partitioned with sat. NaHCO₃ soln. (20 mL). Aqueous layer was separated and partitioned with fresh DCM (20 mL), organics separated, bulked and partitioned with 20% w/w NaCl soln. (20 mL). Organic layer was separated, dried (MgSO₄), filtered and the solvent evaporated. The crude product was purified by chromatography on the Companion 40 g column, 2% MeOH:DCM to 5%) to afford Intermediate D1 (1.5 g) as a thick, colourless oil.

¹H NMR (400 MHz, DMSO-d6) δ 8.37 (t, 1H), 7.08 (t, 1H), 7.00 (dd, 1H), 6.85 (t, 1H), 5.58 (s, 2H), 3.57-3.46 (m, 8H), 3.45-3.39 (m, 2H), 3.39-3.34 (m, 2H), 3.23 (s, 3H).

LCMS m/z 361/363 (M+H)+ (ES+)

Method 2

3-Bromo-5-nitrobenzoic acid (725 g, 2.947 mol) was refluxed in thionyl chloride (2.365 kg, 19.88 mol) until a clear (brown) solution obtained (takes about 3-4 h). [NOTE: HCl is evolved, and so a large NaOH(aq) scrubber is required, with ice/water cooling]. The solution was concentrated in vacuo to provide the (brown) acid chloride (3-bromo-5-nitrobenzoyl chloride).

The acid chloride was dissolved in ethyl acetate (500 mL) and added as a small, controlled stream to 2-(2-(2-methoxyethoxy)ethoxy)ethanamine (481 g, 2.947 mol) dissolved in ethyl acetate (4 L) and triethylamine (447.31 g, 4.42 mol)) at 15° C. over a period of about 1 h. The resulting heavy suspension was stirred overnight at rt, after which brine (5 L) was added to the reaction mixture and the aqueous phase was separated. The aqueous washings were re-extracted with ethyl acetate and then the combined organics were washed with water (1×5 L), dried (MgSO4), and passed through a silica plug (washed with 1×500 mL fresh ethyl acetate). The solvent was evaporated to provide a deep brown oil, to which was added diethyl ether (2 L). The resulting mixture was cooled in an ice bath and stirred for 1 h, after which the solid thereby obtained was washed twice with diethyl ether and then dried. The product (3-nitro-5-bromo-N-(2-(2-(2-methoxyethoxy)ethoxy)ethyl)-benzamide, Intermediate D1*) was obtained as 850 g (73.3%) of a pale brown, amorphous, free flowing solid that was used in the next step without any further purification.

¹H NMR (400 MHz, DMSO-d6) δ 9.04 (t, 1H), 8.66 (dd, 1H), 8.55 (t, 1H), 8.47 (t, 1H), 3.60-3.43 (m, 10H), 3.42-3.37 (m, 2H), 3.21 (s, 3H).

LCMS m/z 391/393 (M+H)+ (ES+); 389/391 (M−H)− (ES−)

Intermediate D1* (250 g, 0.639 mol) was placed in a 4 L autoclave with Pt/C (5%) and IMS (2 L). The mixture was then heated to 80° C. under H₂ (40 atm) for 48 h. The resulting mixture was then cooled and filtered and the residue was washed with fresh IMS. The solvent was evaporated from the combined organics to provide an orange/red oil. This oil was triturated with diethyl ether to provide a suspension of a solid that was filtered, washed with further diethyl ether and then dried. This afforded Intermediate D1 (207.8 g, 90%) as an off-white, amorphous solid that had ¹H NMR and LCMS data essentially identical to those of the material obtained via Method 1 above.

Intermediate D2: 3-Amino-5-ethynyl-N-(2-(2-(2-methoxyethoxy)ethoxy)ethyl)benzamide

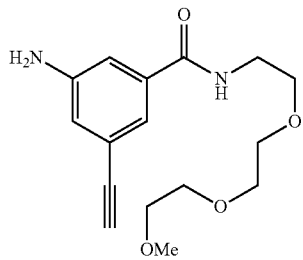 [SMILES: C#Cc1cc(N)cc(C(=O)NCCOCCOCCOC)c1]

Method 1

Pd(PPh$_3$)$_4$ (0.240 g, 0.208 mmol) was added to a degassed suspension of Intermediate D1 (1.5 g, 4.15 mmol), CuI (0.040 g, 0.208 mmol), and ethynyltriisopropylsilane (1.397 ml, 6.23 mmol) in TEA (2 mL) and DMF (10 mL). Heated at 80° C. (block temp.) for 4 h then cooled and filtered (Whatman glass fibre pad GF/A). Solvents were evaporated and the residue partitioned between EtOAc (200 mL) and 20% w/w NaCl soln. (250 mL) Organic layer separated, dried (MgSO$_4$), filtered and solvent evaporated to a thick brown oil found to be an impure mixture of starting material and product. This mixture was subjected to the same reaction conditions and work up as before for 1 h. The crude product was purified by chromatography on the Companion 40 g column, MeOH:EtOAc to 0% to 5%) to afford 3-amino-N-(2-(2-(2-methoxyethoxy)ethoxy)ethyl)-5-((triisopropylsilyl)ethynyl)benzamide (1.5 g) as a thick, yellow oil.

$^1$H NMR (400 MHz, DMSO-d6) δ 8.41 (t, 1H), 7.10-7.01 (m, 2H), 6.79 (dd, 1H), 5.45 (s, 2H), 3.55-3.47 (m, 8H), 3.44-3.35 (m, 4H), 3.22 (s, 3H), 1.10 (s, 21H).

LCMS m/z 463 (M+H)$^+$ (ES$^+$)

The (triisopropylsilyl)ethynyl-substituted benzamide obtained immediately above (1.5 g, 3.24 mmol) was dissolved in EtOAc (15 mL) and TBAF, 1M in THF (3.24 ml, 3.24 mmol) added. Stirred for 1 h then partitioned between water (10 mL) and ethyl acetate (10 mL). The organic layer separated and washed with 20% w/w NaCl soln. (20 mL), dried (MgSO$_4$), filtered and evaporated. The crude product was purified by chromatography on silica gel (40 g column, 1% MeOH:DCM to 6%) to afford Intermediate D2 (750 mg) as a clear, yellow oil.

$^1$H NMR (400 MHz, DMSO-d6) δ 8.36 (t, 1H), 7.12-7.02 (m, 2H), 6.76 (dd, 1H), 5.45 (s, 2H), 4.07 (s, 1H), 3.58-3.46 (m, 8H), 3.45-3.36 (m, 4H), 3.23 (s, 3H).

LCMS m/z 307 (M+H)$^+$ (ES$^+$)

Method 2

Pd(PPh$_3$)$_4$ (90 g, 78 mmol) was added to a degassed (N$_2$ purging for 30 mins) solution of Intermediate D1 (500 g, 1.384 mol), CuI (13.7 g, 72 mmol), ethynyltriisopropylsilane (227.68 g, 1.523 mol) and TEA (667.92 g, 6.601 mol) in DMF (4 L). The mixture was heated to 85° C. under N$_2$ for 7 h before being allowed to cool overnight. As much DMF solvent as possible was removed in vacuo to provide a residue that was then taken up in ethyl acetate. The resulting solution was passed through large silica plug to remove inorganic impurities. The silica plug was washed twice with ethyl acetate. The combined organics were stirred with 1 L of conc. HCl/water (50%) for 10 mins. The aqueous layer was separated and the ethyl acetate layer was discarded (after checking by TLC for any remaining product). The acidic aqueous layer was back washed with diethyl ether (×2), and the organic washings were discarded. The aqueous layer was then basified cautiously with NaOH until the pH reached approximately 9 to 10. The aqueous layer was then extracted twice with ethyl acetate. The combined organics were washed with water, dried (MgSO$_4$) and passed through a silica plug before the solvent was evaporated to provide 3-amino-N-(2-(2-(2-methoxyethoxy)ethoxy)ethyl)-5-((triisopropylsilyl)-ethynyl)benzamide (489.4 g, 76.4%) as a viscous orange/red oil that had $^1$H NMR and LCMS data essentially identical to those of the material obtained via Method 1 above, and which oil was used in the next step without further purification.

The (triisopropylsilyl)ethynyl-substituted benzamide obtained immediately above (290 g, 627 mmol, 1 eq.) was dissolved in EtOAc (2.5 L) and TBAF, 1 M in THF (690.7 mL, 689 mmol, 1.1 eq.) was added in one portion. The resulting mixture was stirred overnight at rt before the solvent was evaporated. The residue was dissolved in fresh ethyl acetate before being washed with a solution of sodium hexafluorophosphate (210 g, 2 eq.) in water (750 mL). The aqueous and organic layers were then separated. The organic layer was dried (MgSO$_4$) and passed through a silica plug. The solvent was then evaporated to provide a solid that was found to contain some TBAF. The solid was then slurried in a small quantity of ethyl acetate and passed through a further silica plug that was washed sparingly with ethyl acetate. Solvent removed from the filtrate in vacuo to provide Intermediate D2 (155.76 g, 81.1%) as a viscous, orange/red oil of about 90% purity that had $^1$H NMR and LCMS data essentially identical to those of the material obtained via Method 1 above, and which oil was used without further purification.

Intermediate D3: 3-Amino-5-methoxy-N-(2-(2-(2-methoxyethoxy)ethoxy)ethyl)-benzamide

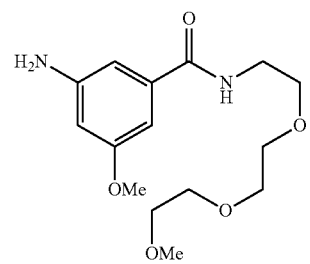 [SMILES: COCCOCCOCCNC(=O)c1cc(N)cc(OC)c1]

3-Amino-5-methoxybenzoic acid (1.0 g, 5.98 mmol) was added to an ice cold suspension of 2-(2-(2-methoxyethoxy)ethoxy)ethanamine (1.2 g, 7.35 mmol), 50% T3P in ethyl acetate (4.50 ml, 7.56 mmol) and TEA (2.5 ml, 17.94 mmol) in ethyl acetate (15 mL). The mixture was allowed to warm to rt and stir overnight. Saturated NaHCO$_3$ (20 mL) was added and the mixture was extracted with ethyl acetate (3×10 mL). The combined organic phases were washed with saturated brine (20 mL), dried (MgSO$_4$) and concentrated under reduced pressure to yield a yellow oil. The oil was purified by chromatography on the Companion (40 g column, 0-100% acetone/toluene) to afford a pale yellow oil. The oil was purified by chromatography on the Companion (40 g column, 0-100% THF/DCM) to afford the subtitle compound (843 mg) as a pale yellow oil.

LCMS m/z 313 (M+H)$^+$ (ES$^+$)

Intermediate D4: 3-Amino-5-bromo-N-(2-(2-methoxyethoxy)ethyl)benzamide

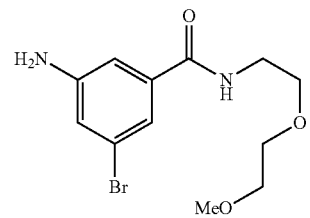 [SMILES: COCCOCCNC(=O)c1cc(N)cc(Br)c1]

A stirred mixture of 3-amino-5-bromobenzoic acid (800 mg, 3.59 mmol), 2-(2-methoxy-ethoxy)ethanamine (856 mg, 7.18 mmol) and triethylamine (1.5 mL, 10.76 mmol) in DCM (13 mL) was cooled in an ice bath. 50 wt % T3P in EtOAc (3.2 mL, 5.38 mmol) was added dropwise, the ice bath was removed and the reaction mixture allowed to warm to rt. DMF (2 mL) was added to aid solubility and the reaction stirred at rt overnight. The reaction mixture was partitioned between sat. aq. NaHCO₃ (50 mL) and DCM (50 mL). The aqueous phase was back extracted with fresh DCM (50 mL). The combined organic extracts were washed with water (100 mL), brine (100 mL), dried (MgSO₄), filtered and concentrated in vacuo to afford an orange oil. The crude product was purified by chromatography on silica gel (40 g column, 0-5% MeOH) to afford Intermediate D4 (880 mg) as an orange oil.

$^1$H NMR (DMSO-d6) 400 MHz, δ: 8.36 (t, 1H), 7.07 (t, 1H), 7.00-6.99 (m, 1H), 6.84 (t, 1H), 5.57 (s, 2H), 3.53-3.48 (m, 4H), 3.44-3.42 (m, 2H), 3.35 (q, 2H), 3.23 (s, 3H).

LCMS m/z 317/319 (M+H)⁺ (ES')

Intermediate D5: 3-Amino-5-ethynyl-N-(2-(2-methoxyethoxy)ethyl)benzamide

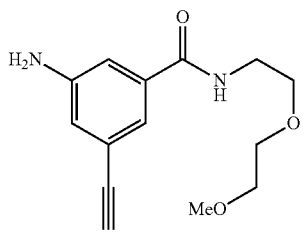

To a degassed solution of Intermediate D4 (830 mg, 2.59 mmol), ethynyltriisopropylsilane (880 µL, 3.92 mmol), copper(I) iodide (24.67 mg, 0.130 mmol) and TEA (1.55 mL, 11.12 mmol) in DMF (8 mL) was added Pd(PPh₃)₄ (150 mg, 0.130 mmol). The reaction was heated at 85° C. for 3 h. The reaction was cooled to rt then partitioned between EtOAc (50 mL) and brine (50 mL). The aqueous phase was back extracted with EtOAc (50 mL). The combined organic extracts were washed with brine (100 mL), dried (MgSO₄), filtered and concentrated in vacuo to afford a brown semisolid (1.65 g). The crude product was purified by chromatography on silica gel (80 g column, 0-3% MeOH in DCM) to afford 3-amino-N-(2-(2-methoxyethoxy)ethyl)-5-((triisopropylsilyl)ethynyl)benzamide (796 mg) as a beige solid.

$^1$H NMR (DMSO-d6) 400 MHz, δ: 8.39 (t, 1H), 7.05-7.04 (m, 1H), 7.03 (t, 1H), 6.79-6.78 (m, 1H), 5.44 (br s, 2H), 3.53-3.48 (m, 4H), 3.44-3.42 (m, 2H), 3.35 (q, 2H), 3.23 (s, 3H), 1.10 (s, 21H).

LCMS m/z 419 (M+H)⁺ (ES⁺)

To a stirred solution of the (triisopropylsilyl)ethynyl-substituted benzamide obtained immediately above (717 mg, 1.473 mmol) in EtOAc (9 mL) was added 1M TBAF in THF (1473 µL, 1.473 mmol). The reaction was stirred at rt for 1 h. The reaction mixture was partitioned between water (30 mL) and EtOAc (20 mL). The organic layer was washed with brine (20 mL), dried (MgSO₄), filtered and concentrated to afford a brown oil. The crude product was dissolved in the minimum quantity of MeOH and loaded onto SCX. The column was eluted with MeOH followed by 1% NH₃ in MeOH. The filtrate was concentrated in vacuo to afford a brown oil at ~70% purity. The crude product was purified by chromatography on silica gel (40 g column, 0-5% MeOH in DCM) to afford Intermediate D5 (377 mg) as an orange oil.

$^1$H NMR (DMSO-d6) 400 MHz, δ: 8.36 (t, 1H), 7.06-7.04 (m, 2H), 6.75-6.74 (m, 1H), 5.45 (s, 2H), 4.07 (s, 1H), 3.53-3.47 (m, 4H), 3.44-3.42 (m, 2H), 3.37-3.33 (m, 2H), 3.23 (s, 3H).

LCMS m/z 263 (M+H)⁺ (ES⁺)

Intermediate G1(P): tert-Butyl (4-((2-chloropyridin-4-yl)oxy)naphthalen-1-yl)carbamate

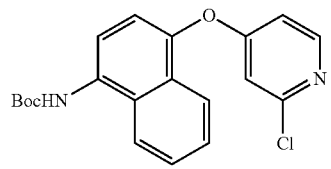 [SMILES: CC(C)(C)OC(=O)Nc1ccc(Oc2ccnc(Cl)c2)c2ccccc12]

A mixture of Intermediate G1 (1000 mg, 3.69 mmol) di-tert-butyl dicarbonate (750 mg, 3.44 mmol) in t-BuOH (10 mL) was stirred at reflux for 18 h. The mixture was diluted with water (15 mL) and collected by filtration. The solid was triturated in diethyl ether to yield Intermediate G1(P) (1002 mg) as a pale grey solid.

$^1$H NMR (DMSO-d6) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H).

LCMS m/z 371 (M+H)⁺ (ES⁺); 369 (M−H)⁻ (ES⁻)

Intermediate G3: 4-((2-Chloropyrimidin-4-yl)oxy)-5,6,7,8-tetrahydronaphthalen-1-amine

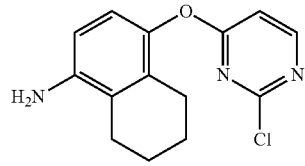 [SMILES: Nc1ccc(Oc2ccnc(Cl)n2)c2c1CCCC2]

2,4-Dichloropyrimidine (0.958 g, 6.43 mmol) was added to a stirred mixture of 4-amino-5,6,7,8-tetrahydronaphthalen-1-ol (1 g, 6.13 mmol) and DBU (1.1 mL, 7.30 mmol) at 0-5° C. The mixture was stirred for 3 h then more DBU (0.6 mL) and 2,4-dichloropyrimidine (300 mg) added and stirred for a further 2 h. The mixture was partitioned between EtOAc (100 mL) and water (50 mL), the organic layer was washed with water (50 mL), dried (MgSO₄), filtered and evaporated under reduced pressure. The crude product was purified by chromatography on silica gel (80 g column, 0-50% EtOAc/isohexane) to afford Intermediate G3 (510 mg) as brown solid.

$^1$H NMR (CDCl₃) 400 MHz, δ: 8.36 (d, 1H), 6.74 (d, 1H), 6.62 (d, 1H), 6.56 (d, 1H), 3.60 (s, 2H), 2.49-2.46 (m, 4H), 1.87-1.81 (m, 2H), 1.74-1.68 (m, 2H).

LCMS m/z 276/8 (M+H)⁺ (ES⁺)

Intermediate J1(P): 3-((4-((4-((tert-Butoxycarbonyl)amino)naphthalen-1-yl)oxy)pyrimidin-2-yl)amino)-5-ethynylbenzoic acid

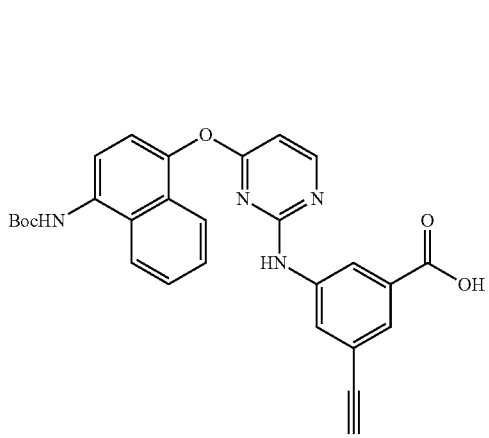 [SMILES: C#Cc1cc(Nc2nccc(Oc3ccc(NC(=O)OC(C)(C)C)c4ccccc34)n2)cc(C(=O)O)c1]

A suspension of Intermediate G2(P) (42.6 g, 115 mmol), Intermediate K1* (40.00 g, 126 mmol), BINAP (6.42 g, 10.31 mmol) and caesium carbonate (74.6 g, 229 mmol) in 1,4-dioxane (500 mL) was degassed with nitrogen for 10 minutes. Pd₂(dba)₃ (4.20 g, 4.58 mmol) was added and the mixture was heated to 90° C. for 2.5 h. The mixture was diluted with diethyl ether (600 mL) then washed with water (600 mL), followed by 0.5 M HCl solution (500 mL) and saturated brine (500 mL). The organic phase was dried (MgSO₄), filtered and concentrated in vacuo affording 3-((4-((4-((tert-butoxycarbonyl)amino)naphthalen-1-yl)oxy)pyrimidin-2-yl)amino)-5-((triisopropylsilyl)ethynyl)benzoic acid (Intermediate J1(P)*, 96 g) as a red foam which was used without further purification.

Intermediate J1(P)* (96 g) was dissolved in THF (60 mL) and diluted with MeCN (400 mL). 1.0 M TBAF in THF (235 mL, 235 mmol) was added and the reaction stirred at rt overnight. The reaction was diluted with MeCN (300 mL) and water (600 mL), then 1M HCl solution (100 mL, 1 eq.) was added and stirring continued resulting in the precipitation of a pink solid which was collected by filtration. The pink solid was triturated in MeCN at 80° C., collected by filtration and dried at 40° C. under vacuum for 2 h. The solid was re-suspended in (9:1) EtOAc/THF (400 ml) and heated to 60° C. for 90 mins then cooled to room temperature and stirred overnight. The suspended solid was collected by filtration, washing with EtOAc affording Intermediate J1(P) (47 g) as a pale yellow/beige solid.

¹H NMR (400 MHz, DMSO-d6) δ: 13.12 (bs, 1H), 9.83 (s, 1H), 9.32 (s, 1H), 8.46 (d, 1H), 8.28 (s, 1H), 8.10 (d, 1H), 8.01 (s, 1H), 7.82 (d, 1H), 7.54-7.63 (m, 3H), 7.49 (s, 1H), 7.42 (d, 1H), 6.61 (d, 1H), 4.17 (s, 1H), 1.52 (s, 9H).

LCMS m/z 497 (M+H)⁺ (ES⁺); 495 (M−H)⁻ (ES⁻)

Intermediate J2(P): 3-((4-((4-((tert-Butoxycarbonyl)amino)naphthalen-1-yl)oxy)pyridin-2-yl)amino)-5-ethynylbenzoic acid

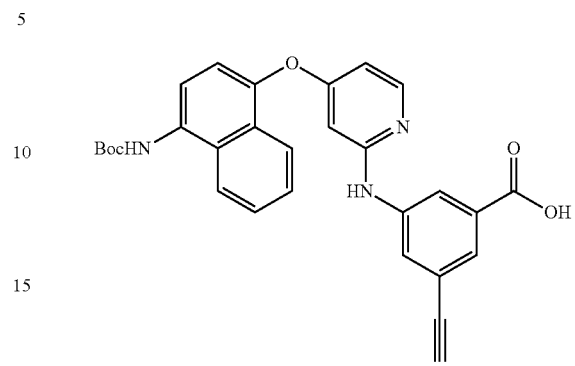

N₂ was bubbled through a mixture of Intermediate G1(P) (0.5 g, 1.348 mmol), 3-amino-5-((triisopropylsilyl)ethynyl)benzoic acid (0.490 g, 1.544 mmol), Cs₂CO₃ (0.966 g, 2.97 mmol), BINAP (0.078 g, 0.125 mmol) and Pd₂dba₃ (0.056 g, 0.061 mmol) in dioxane (15 mL) for 10 min then heated at 90 C for 4 h. The mixture was partitioned between ether (100 mL) and 1M HCl (50 mL), the organic layer separated, washed with water, dried (MgSO₄), filtered and evaporated under reduced pressure. The residue was triturated with ether/isohexane, filtered and dried to afford 3-((4-((4-((tert-butoxycarbonyl)amino)naphthalen-1-yl)oxy)pyridin-2-yl)amino)-5-((triisopropylsilyl)ethynyl)benzoic acid (760 mg) which was used crude in the next step.

1.0 M TBAF in THF (2.5 ml, 2.500 mmol) was added to a stirred solution of 3-((4-((4-((tert-butoxycarbonyl)amino)naphthalen-1-yl)oxy)pyridin-2-yl)amino)-5-((triisopropylsilyl)ethynyl)-benzoic acid obtained immediately above (760 mg) in THF (15 mL). The mixture was stirred for 2 h then water (10 mL) added and acidified to pH-4 with 1M HCl. The mixture was partitioned between EtOAc (70 mL) and water (40 mL), the organic phase washed with sat brine (50 mL), dried (MgSO₄), filtered and evaporated under reduced pressure. The crude product was purified by chromatography on silica gel (40 g column, 0-100% EtOAc/isohexane) to afford Intermediate J2(P) (344 mg) as a foam.

¹H NMR (DMSO-d6) 400 MHz, δ: 13.07 (s, 1H), 9.39 (s, 1H), 9.29 (s, 1H), 8.18-8.13 (m, 4H), 7.84 (d, 1H), 7.66-7.56 (m, 3H), 7.44 (s, 1H), 7.38 (d, 1H), 6.66 (dd, 1H), 6.07 (d, 1H), 4.22 (s, 1H), 1.53 (s, 9H).

LCMS m/z 496 (M+H)⁺ (ES⁺)

Intermediate J3(P): 3-((4-((4-((tert-Butoxycarbonyl)amino)naphthalen-1-yl)oxy)pyrimidin-2-yl)amino)-5-methoxybenzoic acid

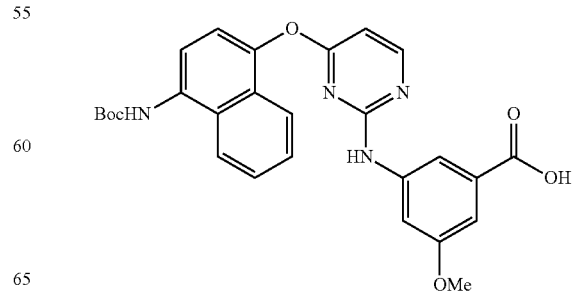

N₂ was bubbled through a stirred mixture of Intermediate G2(P) (10 g, 26.9 mmol), 3-amino-5-methoxybenzoic acid (8.99 g, 53.8 mmol) and p-TSA monohydrate (1.02 g, 5.36 mmol) in THF (150 mL) for 10 min. The mixture was heated under reflux for 20 h, cooled and filtered. The filtrate was evaporated, MeOH (300 mL) added and the solid filtered, washed with MeOH then ether to afford the sub-title compound (10.063 g).

$^1$H NMR (400 MHz; DMSO-d6) δ 12.83 (brs, 1H), 9.68 (s, 1H), 9.32 (s, 1H), 8.44 (d, 1H), 8.11 (d, 1H), 8.13-8.10 (m, 2H), 7.61-7.51 (m, 4H), 7.41 (d, 1H), 6.98 (s, 1H), 6.58 (d, 1H), 3.60 (s, 3H), 1.52 (s, 9H).

LCMS m/z 503 (M+H)$^+$ (ES$^+$)

Intermediate K1*:
3-Amino-5-((triisopropylsilyl)ethynyl)benzoic acid

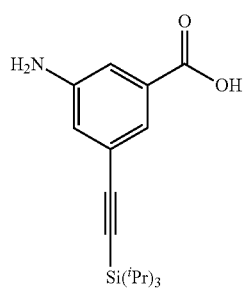

Pd(PPh₃)₄ (9.36 g, 8.10 mmol) was added to a degassed suspension of 3-amino-5-bromobenzoic acid (50 g, 231 mmol), CuI (1.499 g, 7.87 mmol), and ethynyltriisopropylsilane (80 mL, 356 mmol) in Et₃N (300 mL) and DMF (300 mL). The mixture was heated to 90° C. for 2 h. The mixture was cooled and carefully poured into ice-cold HCl (2.0 M aq.; 1100 mL, 2200 mmol) and diluted with diethyl ether (500 mL). The biphasic mixture was filtered to remove palladium residues. The layers of the filtrate were separated and the aqueous phase was extracted with a further portion of diethyl ether (300 mL). The organic phases were combined and washed with 20% brine (2×300 mL), 40% brine (300 mL), dried (MgSO₄), filtered and concentrated in vacuo affording a pale orange solid. The solid was recrystallised in acetonitrile (250 mL) and collected by filtration, washing with fresh acetonitrile (2×30 mL) affording the product as a yellow solid. The solid was slurried in hexane (250 mL) for 5 h then filtered, washing with more hexane to afford Intermediate K1* (45.5 g) as a pale yellow solid.

$^1$H NMR (400 MHz, DMSO-d6) δ: 12.87 (bs, 1H), 7.18 (t, 1H), 7.10 (t, 1H), 6.86 (t, 1H), 5.54 (bs, 2H), 1.10 (s, 21H).

LCMS m/z 318 (M+H)$^+$ (ES$^+$); 316 (M-H)$^-$ (ES$^-$)

Intermediate M1: 3-(tert-Butyl)-1-(4-(dimethylamino)phenyl)-1H-pyrazole-5-carboxylic acid

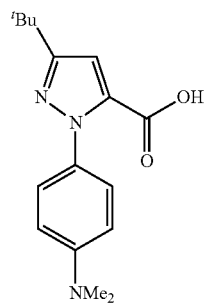 [SMILES: CN(C)c1ccc(-n2nc(C(C)(C)C)cc2C(=O)O)cc1]

Pyridine (350 μL, 4.33 mmol) followed by activated 4A molecular sieves (0.5 g) were added to a stirred mixture of (4-(dimethylamino)phenyl)boronic acid (575 mg, 3.48 mmol), ethyl 3-(tert-butyl)-1H-pyrazole-5-carboxylate (425 mg, 2.166 mmol) and copper (II) acetate (590 mg, 3.25 mmol) in DCM (15 mL) at rt. open to the air. The mixture was stirred for 4 h. A mixture of ether/isohexane (3:1, 300 mL) was added and the solid was filtered off. The filtrate was evaporated under reduced pressure and the residue was purified by chromatography on the Companion (80 g column, 0-60% ether/isohexane) to afford ethyl 3-(tert-butyl)-1-(4-(dimethylamino)phenyl)-1H-pyrazole-5-carboxylate (Intermediate M(P)1; 464 mg) as a colourless oil.

LCMS m/z 316 (M+H)$^+$ (ES$^+$) 1 M sodium hydroxide solution (1.5 ml, 1.500 mmol) was added to a stirred solution of Intermediate M(P)1 (0.46 g, 1.458 mmol) in THF (3 mL) at rt. The mixture was stirred for 3 h at rt then methanol (1 mL) was added and the mixture was stirred for a further 1 h. The mixture was then heated to 40° C. for 1 h, diluted with water (10 mL) and washed with diethyl ether (2×10 mL). The aqueous phase was treated with 1 M HCl (1.5 mL) and extracted with ethyl acetate (3×10 mL). The combined organic phases were washed with saturated brine (10 mL), dried (MgSO₄) and concentrated to yield Intermediate M1 (395 mg) as an off-white solid.

$^1$H NMR (400 MHz; CDCl₃) δ: 7.28-7.22 (m, 2H), 6.91 (s, 1H), 6.74-6.67 (m, 2H), 2.98 (s, 6H), 1.35 (s, 9H).

LCMS m/z 288 (M+H)$^+$ (ES$^+$); 286 (M-H)$^-$ (ES$^-$)

Intermediate M2: 3-(tert-Butyl)-1-(2,4-dimethoxyphenyl)-1H-pyrazole-5-carboxylic acid

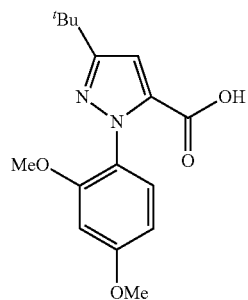 [SMILES: COc1ccc(-n2nc(C(C)(C)C)cc2C(=O)O)c(OC)c1]

Pyridine (2.3 mL, 28.4 mmol) followed by activated 4A molecular sieves (2 g) were added to a stirred mixture of (2,4-dimethoxyphenyl)boronic acid (3.88 g, 21.31 mmol), ethyl 3-(tert-butyl)-1H-pyrazole-5-carboxylate (2.79 g, 14.20 mmol) and copper (II) acetate (3.87 g, 21.31 mmol) in DCM (50 mL) at rt. open to the air. The mixture was stirred for 3 days then a mixture of ether/isohexane (3:1, 300 mL) was added and the solid was filtered off. The filtrate was evaporated under reduced pressure and the residue was purified by chromatography on silica gel (120 g column, 0-20% EtOAc/isohexane) to afford ethyl 3-(tert-butyl)-1-(2, 4-dimethoxyphenyl)-1H-pyrazole-5-carboxylate (Intermediate M(P)2; 377 mg) as an oil.

$^1$H NMR (CDCl$_3$) 400 MHz, δ: 7.31 (d, 1H), 6.84 (s, 1H), 6.56 (dd, 1H), 6.54 (d, 1H), 4.21 (q, 2H), 3.86 (s, 3H), 3.73 (s, 3H), 1.38 (s, 9H), 1.24 (t, 3H).

LCMS m/z 333 (M+H)$^+$ (ES$^+$)

A mixture of Intermediate M(P)2 (365 mg, 0.933 mmol), LiOH (70 mg, 2.92 mmol) in THF (5 mL) and water (2 mL) was stirred at rt for 4 h. EtOH (5 mL) was added and the mixture stirred at rt for 18 h. The solvent was evaporated and the residue partitioned between EtOAc (30 mL) and aq 1M HCl (30 mL). The organic layer was washed with water (10 mL), dried (MgSO$_4$), filtered and evaporated under reduced pressure to give a gum that was triturated with ether/isohexane to afford Intermediate M2 (220 mg) as a white solid.

$^1$H NMR (CDCl$_3$) 400 MHz, δ: 7.32 (d, 1H), 6.91 (s, 1H), 6.56 (dd, 1H), 6.52 (d, 1H), 3.86 (s, 3H), 3.72 (s, 3H), 1.38 (s, 9H).

LCMS m/z 305 (M+H)$^+$ (ES$^+$); 303 (M-H)$^-$ (ES$^-$)

Intermediate M(P)3: Ethyl 3-(tert-butyl)-1-(3-(hydroxymethyl)phenyl)-1H-pyrazole-5-carboxylate

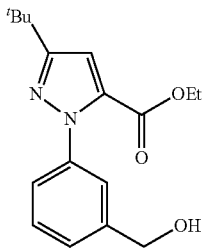 [SMILES: CCOC(=O)c1cc(C(C)(C)C)nn1-c1cccc(CO)c1]

To a stirred mixture of ethyl 3-(tert-butyl)-1H-pyrazole-5-carboxylate (4.39 g, 22.37 mmol), (3-(hydroxymethyl)phenyl)boronic acid (5.1 g, 33.6 mmol) and copper (II) acetate (6.10 g, 33.6 mmol) in DCM (130 mL) was added pyridine (3.62 mL, 44.7 mmol) followed by 4A molecular sieves. The resulting mixture was stirred at rt open to the air for 48 h. The reaction mixture was filtered and the filtrate concentrated in vacuo. Et$_2$O (200 mL) was added, the resulting mixture filtered and the filtrated concentrated in vacuo to afford a green oil. The crude product was purified by chromatography on silica gel (120 g column, 0-40% EtOAc in isohexane) to afford Intermediate M(P)3 (6.2 g) as an oil.

$^1$H NMR (DMSO-d6) 400 MHz, δ: 7.42-7.35 (m, 3H), 7.27-7.24 (m, 1H), 6.97 (s, 1H), 5.31 (t, 1H), 4.56 (d, 2H), 4.17 (q, 2H), 1.30 (s, 9H), 1.16 (t, 3H).

LCMS m/z 303 (M+H)$^+$ (ES$^+$)

Intermediate M(P)4: Ethyl 3-(tert-butyl)-1-(3-(chloromethyl)phenyl)-1H-pyrazole-5-carboxylate

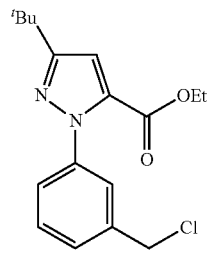 [SMILES: CCOC(=O)c1cc(C(C)(C)C)nn1-c1cccc(CCl)c1]

To a stirred solution of Intermediate M(P)3 (6.2 g, 20.50 mmol) in DCM (10 mL) was added SOCl$_2$ (1 M in DCM, 41.0 mL, 41.0 mmol). The resulting solution was stirred at rt for 2 h. The solvent was removed in vacuo and the crude product was purified by chromatography on silica gel (220 g column, 0-100% EtOAc in isohexane) to afford Intermediate M(P)4 (5.64 g) as an oil.

$^1$H NMR (DMSO-d6) 400 MHz, δ: 7.52-7.45 (m, 3H) 7.41-7.38 (m, 1H) 7.00 (s, 1H) 4.83 (s, 2H) 4.17 (q, 2H) 1.30 (s, 9H) 1.16 (t, 3H).

LCMS m/z 321 (M+H)$^+$ (ES$^+$)

Intermediate M5: 3-(tert-Butyl)-1-(3-((dimethylphosphoryl)methyl)phenyl)-1H-pyrazole-5-carboxylic acid

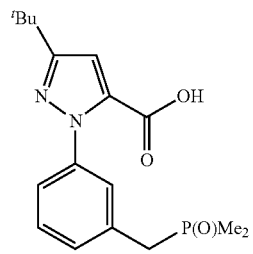

A suspension of Intermediate M(P)4 (3.65 g, 10.81 mmol), xantphos (0.375 g, 0.649 mmol), palladium(II) acetate (0.121 g, 0.540 mmol), potassium phosphate, tribasic (2.52 g, 11.89 mmol) and dimethylphosphine oxide (0.928 g, 11.89 mmol) in DMF (30 mL) was purged with N$_2$ for 20 mins. The reaction mixture was heated at 110° C. for 1 h, cooled to rt then partitioned between DCM (300 mL) and water (200 mL). The organic layer was washed with water (2×200 mL), brine (300 mL), dried (MgSO$_4$), filtered and concentrated in vacuo. The crude product was purified by chromatography on silica gel (120 g column, 0-10% MeOH/DCM) to afford ethyl 3-(tert-butyl)-1-(3-((dimethylphosphoryl)methyl)phenyl)-1H-pyrazole-5-carboxylate (Intermediate M(P)5, 2.29 g) as an oil which solidified on standing.

$^1$H NMR (CDCl$_3$) 400 MHz, δ: 7.43-7.27 (m, 4H), 6.87 (s, 1H), 4.22 (q, 2H), 3.23 (d, 2H), 1.48 (d, 6H), 1.36 (s, 9H), 1.28 (t, 3H).

LCMS m/z 363 (M+H)$^+$ (ES$^+$)

Sodium hydroxide (1 M aq.) (12.0 mL, 12.00 mmol) was added to a stirred solution of Intermediate M(P)5 (2.2 g, 6.07 mmol) in EtOH (40 mL). The resulting mixture was stirred at rt for 3 h. The solvent was removed in vacuo and the resulting residue partitioned between 1M HCl (90 mL) and EtOAc (300 mL). The organic layer was washed with brine (150 mL), dried (MgSO$_4$), filtered and concentrated in vacuo to afford Intermediate M5 (1.61 g) as a cream solid.

$^1$H NMR (DMSO-d6) 400 MHz, δ: 13.18 (bs, 1H), 7.39-7.43 (m, 1H), 7.29-7.31 (m, 3H), 6.93 (s, 1H), 3.23 (d, 2H), 1.36 (d, 6H), 1.30 (s, 9H).

LCMS m/z 335 (M+H)$^+$ (ES$^+$); 333 (M−H)$^−$ (ES$^−$)

COMPOUND EXAMPLES OF THE INVENTION

Example 1: 3-Ethynyl-5-((4-((4-(3-(3-isopropyl-1-(p-tolyl)-1H-pyrazol-5-yl)ureido)-naphthalen-1-yl)oxy)pyrimidin-2-yl)amino)-N-(2-(2-(2-methoxyethoxy)ethoxy)ethyl)-benzamide

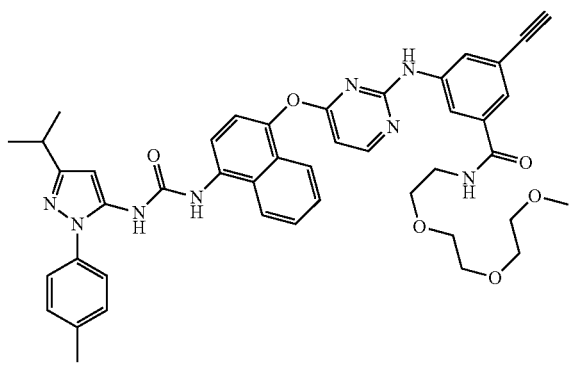 [SMILES: C#Cc1cc(Nc2nccc(Oc3ccc(NC(=O)Nc4cc(C(C)C)nn4-c4ccc(C)cc4)c4ccccc34)n2)cc(C(=O)NCCOCCOCCOC)c1]

Intermediate C1 (146 mg, 0.285 mmol) was dissolved in DMF (3 mL) and added to Intermediate D2 (87 mg, 0.285 mmol) and p-TSA monohydrate (27.1 mg, 0.142 mmol). Stirred at 70° C. (block temperature) for 7 h then poured into sat. NaHCO$_3$ solution (20 mL) and the product extracted with EtOAc (2×20 mL). Organics bulked and washed with 20% w/w brine solution (20 mL), dried (MgSO$_4$), filtered and evaporated to a yellow solid. The crude product was preabsorbed onto silica (4 g) and purified by chromatography on silica gel (40 g column, 1% MeOH:DCM to 6%) to afford a pale brown solid. Triturated 4 times with MeCN (2 mL) to afford the title compound (60 mg)

$^1$H NMR (400 MHz, DMSO-d6) δ 9.76 (s, 1H), 9.09 (s, 1H), 8.78 (s, 1H), 8.51-8.40 (m, 2H), 8.13-8.01 (m, 2H), 7.94 (d, 1H), 7.87 (s, 1H), 7.82 (d, 1H), 7.68-7.54 (m, 2H), 7.53-7.32 (m, 6H), 6.56 (d, 1H), 6.38 (s, 1H), 4.11 (s, 1H), 3.58-3.46 (m, 8H), 3.43-3.35 (m, 4H), 3.21 (s, 3H), 2.90 (hept, 1H), 2.41 (s, 3H), 1.25 (d, 6H).

LCMS m/z 783 (M+H)$^+$ (ES$^+$)

Example 2: 3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)-benzamide

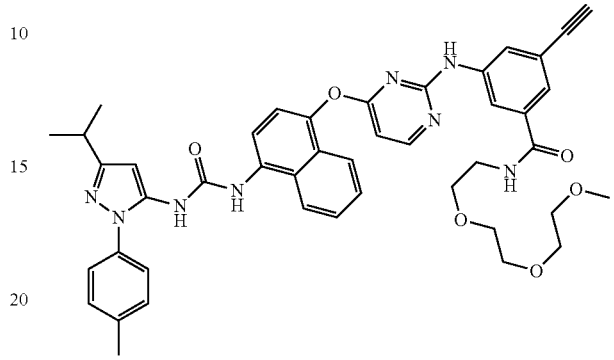

Method 1

A suspension of Intermediate C2 (165 mg, 0.282 mmol), Intermediate D2 (173 mg, 0.564 mmol) and p-TSA monohydrate (11.0 mg, 0.058 mmol) in THF/DMF (6 mL, 1:2) was heated at 60° C. overnight. The reaction was cooled to rt and partitioned between EtOAc (40 mL) and sat. aq. NaHCO$_3$ (30 mL). The aqueous layer was extracted with EtOAc (2×40 mL). The combined organic extracts were washed with water (2×50 mL), brine (2×50 mL), dried (MgSO$_4$), filtered and concentrated in vacuo. The crude product was purified by chromatography on silica gel (40 g column, 0-10% MeOH) to afford a pale yellow solid. The solid was triturated with EtOAc affording the title compound (68 mg) as a white solid.

$^1$H NMR (DMSO-d6) 400 MHz, δ: 9.75 (s, 1H), 9.08 (s, 1H), 8.76 (s, 1H), 8.43-8.46 (m, 2H), 8.06-8.08 (m, 2H), 7.94 (d, 1H), 7.87 (s, 1H), 7.83 (d, 1H), 7.56-7.65 (m, 6H), 6.56 (d, 1H), 6.42 (s, 1H), 4.10 (s, 1H), 3.48-3.53 (m, 8H), 3.36-3.41 (m, 4H), 3.21 (s, 3H), 2.41 (s, 3H), 1.30 (s, 9H).

LCMS m/z 399 (M+2H)$^{2+}$ (ES$^+$)

Method 2

TEA (13.38 g, 132 mmol) was added to solution of Intermediate A1* (219 g, 627 mmol) and Intermediate B2 (503.11 g, 929 mmol) in isopropyl acetate (4 L) in a 10 L jacketed vessel. The resulting mixture was heated to 50-60° C. under stirring. After about 5 minutes, a heavy precipitate started to form. Stirring was continued for a further 2 h. Analysis by TLC (ethyl acetate) indicated consumption of the starting materials. Heating was ceased and the suspension allowed to cool slowly overnight. The reaction mixture was then filtered through a cloth on a large diameter (40 cm), large pore clay filter. The solid product was washed with ethyl acetate and then n-hexane to provide the title compound (256 g, 51.2%) as a colourless, amorphous solid that had $^1$H NMR and LCMS data essentially identical to those of the material obtained via Method 1 above.

Example 3: 3-((4-((4-(3-(3-(tert-Butyl)-1-(4-methoxyphenyl)-1H-pyrazol-5-yl)ureido)-naphthalen-1-yl)oxy)pyrimidin-2-yl)amino)-5-ethynyl-N-(2-(2-(2-methoxyethoxy)-ethoxy)ethyl)benzamide Example 4: 3-((4-((4-(3-(3-(tert-Butyl)-1-(p-tolyl)-1H-pyrazol-5-yl)ureido)naphthalen-1-yl)oxy)pyridin-2-yl)amino)-5-methoxy-N-(2-(2-(2-methoxyethoxy)ethoxy)ethyl)-benzamide

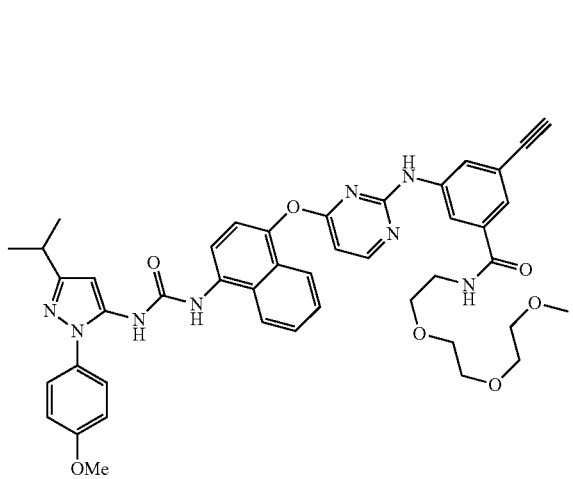 [SMILES: C#Cc1cc(Nc2nccc(Oc3ccc(NC(=O)Nc4cc(C(C)C)nn4-c4ccc(OC)cc4)c4ccccc34)n2)cc(C(=O)NCCOCCOCCOC)c1]

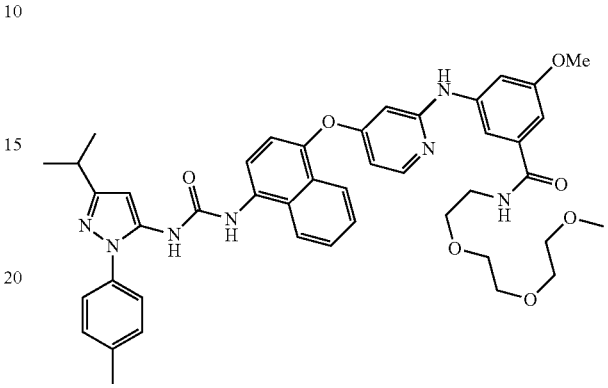

To a stirred solution of Intermediate C3 (175 mg, 0.316 mmol) and Intermediate D2 (153 mg, 0.474 mmol) in DMF (4 mL) was added p-TSA monohydrate (30 mg, 0.158 mmol). The resulting solution was heated at 60° C. overnight. The reaction was cooled to rt and partitioned between EtOAc (30 mL) and sat aq. NaHCO$_3$ (30 mL). The aqueous phase was back extracted with EtOAc (30 mL). The combined organic extracts were washed with water (2×50 mL), brine (50 mL), dried (MgSO$_4$), filtered and concentrated in vacuo to afford an orange oil (276 mg) at 85% purity. The crude product was purified by chromatography on silica gel (40 g column, 0-10% MeOH in DCM) to afford a pink solid (188 mg), which was triturated with MeCN to afford the title compound (98 mg) as an off-white solid.

$^1$H NMR (DMSO-d6) 400 MHz, δ: 9.75 (s, 1H), 9.08 (s, 1H), 8.72 (s, 1H), 8.46 (t, 1H), 8.43 (d, 1H), 8.06-8.04 (m, 2H), 7.93 (d, 1H), 7.86 (br s, 1H), 7.82-7.80 (m, 1H), 7.64-7.54 (m, 2H), 7.50-7.46 (m, 2H), 7.45-7.42 (m, 2H), 7.14-7.10 (m, 2H), 6.55 (d, 1H), 6.39 (s, 1H), 4.11 (s, 1H), 3.84 (s, 3H), 3.53-3.46 (m, 8H), 3.40-3.35 (m, 4H), 3.20 (s, 3H), 1.28 (s, 9H).

LCMS m/z 813 (M+H)$^+$ (ES$^+$)

Triethylamine (6 μL, 0.043 mmol) was added to a mixture of Intermediate A1* (75 mg, 0.215 mmol) and Intermediate B1 (128 mg, 0.234 mmol) in isopropyl acetate (2 mL) and the mixture heated at 50° C. for 2 h. The reaction mixture was concentrated under reduced pressure then purified by chromatography on the Companion (80 g column, 0-50% acetone/EtOAc) to afford a colourless gum. The gum was purified by chromatography on the Companion (40 g column, 5% MeOH/DCM) to afford a tan foam. The crude product was purified by preparative HPLC (Waters, Acidic (0.1% Formic acid), Waters X-Select Prep-C18, 5 μm, 19×50 mm column, 25-70% MeCN in Water) to afford the title compound (55 mg) as a white solid.

$^1$H NMR (DMSO-d6) 400 MHz, δ: 9.19 (s, 1H), 9.06 (s, 1H), 8.84 (s, 1H), 8.34 (dd, 1H), 8.13-8.07 (m, 2H), 7.97 (d, 1H), 7.85 (dd, 1H), 7.69-7.62 (m, 1H), 7.62-7.55 (m, 2H), 7.52-7.44 (m, 3H), 7.41-7.33 (m, 3H), 6.91-6.86 (m, 1H), 6.55 (dd, 1H), 6.42 (s, 1H), 6.13 (d, 1H), 3.75 (s, 3H), 3.56-3.46 (m, 8H), 3.43-3.34 (m, 4H), 3.21 (s, 3H), 2.41 (s, 3H), 1.30 (s, 9H).

LCMS m/z 802 (M+H)$^+$ (ES$^+$); 800 (M−H)$^-$ (ES$^-$)

Example 5: 3-((4-((4-(3-(3-(tert-Butyl)-1-(4-methoxyphenyl)-1H-pyrazol-5-yl)ureido)-naphthalen-1-yl)oxy)pyrimidin-2-yl)amino)-5-ethynyl-N-(2-(2-methoxyethoxy)ethyl)-benzamide

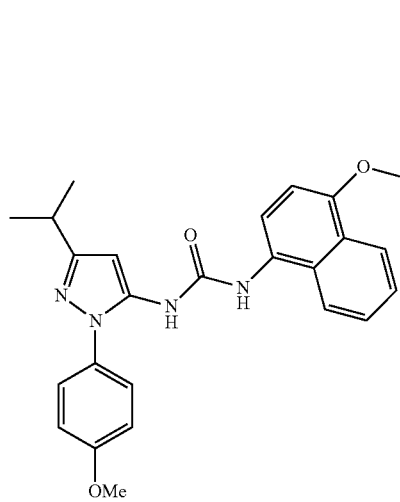
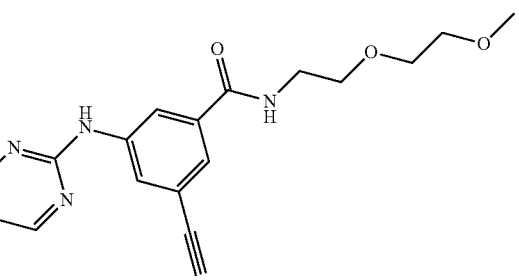

To a stirred solution of Intermediate C3 (152 mg, 0.274 mmol) and Intermediate D5 (124 mg, 0.411 mmol) in DMF (4 mL) was added p-TSA monohydrate (26 mg, 0.137 mmol). The resulting solution was heated at 60° C. overnight. The reaction was cooled to rt and partitioned between EtOAc (30 mL) and sat aq. NaHCO$_3$ (30 mL). The aqueous phase was back extracted with EtOAc (30 mL). The combined organic extracts were washed with water (2×50 mL), brine (50 mL), dried (MgSO$_4$), filtered and concentrated in vacuo to afford a dark orange glass. The crude product was purified by chromatography on silica gel (40 g column, 0-10% MeOH in DCM) to afford a pale pink solid, which was triturated with Et$_2$O to afford a pale, pink solid (25 mg). The crude product was purified by preparative HPLC (Waters, Acidic (0.1% Formic acid), Waters X-Select Prep-C18, 5 μm, 19×50 mm column, 45-65% MeCN in Water) to afford the title compound (13 mg) as an off-white solid.

$^1$H NMR (DMSO-d6) 400 MHz, δ: 9.77 (s, 1H), 9.14 (s, 1H), 8.79 (s, 1H), 8.48 (t, 1H), 8.44 (d, 1H), 8.07-8.04 (m, 2H), 7.93 (d, 1H), 7.86 (br s, 1H), 7.81 (d, 1H), 7.64-7.54 (m, 2H), 7.50-7.41 (m, 4H), 7.12 (d, 2H), 6.56 (d, 1H), 6.39 (s, 1H), 4.12 (s, 1H), 3.83 (s, 3H), 3.53-3.48 (m, 4H), 3.43-3.41 (m, 2H), 2H under water peak at 3.35 ppm, 3.22 (s, 3H), 1.28 (s, 9H).

LCMS m/z 385 (M+2H)$^{2+}$ (ES$^+$)

Example 6: 3-((4-((4-(3-(3-(tert-Butyl)-1-(2,3,5,6-tetradeutero-4-(trideuteromethyl)-phenyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide

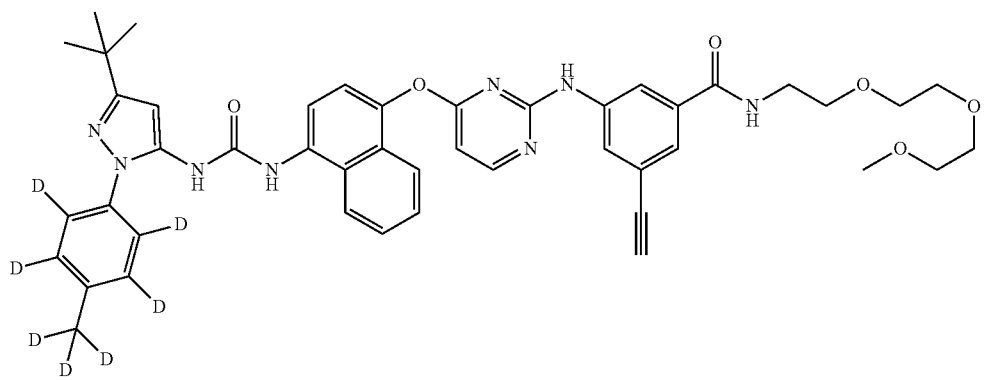 [SMILES: [2H]c1c([2H])c(C([2H])([2H])[2H])c([2H])c([2H])c1-n1nc(C(C)(C)C)cc1NC(=O)Nc1ccc(Oc2ccnc(Nc3cc(C#C)cc(C(=O)NCCOCCOCCOC)c3)n2)c2ccccc12]

A mixture of Intermediate A4* (0.5 g, 1.403 mmol), Intermediate B2 (0.760 g, 1.403 mmol) and Et₃N (40 μL, 0.287 mmol) in iPrOAc (20 mL) were stirred at 50° C. for 3 h. The mixture was cooled, filtered and the solid washed with iPrOAc (15 mL), EtOAc (15 mL) then MeCN (15 mL). The solid was dried at 50° C. under vacuum to afford the title compound (745 mg) as a white solid.

$^1$H NMR (DMSO-d6) 400 MHz, δ: 9.75 (s, 1H), 9.09 (s, 1H), 8.76 (s, 1H), 8.47-8.43 (m, 2H), 8.08-8.06 (m, 2H), 7.94 (d, 1H), 7.87 (s, 1H), 7.83 (d, 1H), 7.65-7.56 (m, 2H), 7.45 (s, 1H), 7.43 (d, 1H), 6.56 (d, 1H), 6.42 (s, 1H), 4.10 (s, 1H), 3.54-3.48 (m, 8H), 3.41-3.36 (m, 4H), 3.21 (s, 3H), 1.30 (s, 9H)

LCMS m/z 804 (M+H)⁺ (ES⁺)

was recrystallised in MeCN (40 mL) and the resulting white solid isolated by filtration washing with further MeCN. The crude product was purified by chromatography on silica gel (12 g column, 1-5% MeOH in DCM) to afford the title compound (316 mg) as a white solid.

$^1$H NMR (400 MHz, DMSO-d6) δ: 9.75 (s, 1H), 9.08 (s, 1H), 8.76 (s, 1H), 8.43-8.47 (m, 2H), 8.06-8.08 (m, 2H), 7.94 (d, 1H), 7.87 (s, 1H), 7.83 (d, 1H), 7.63 (t, 1H), 7.57 (t, 1H), 7.37-7.48 (m, 6H), 6.56 (d, 1H), 6.42 (s, 1H), 4.10 (s, 1H), 3.46-3.53 (m, 12H), 3.36-3.42 (m, 4H), 3.21 (s, 3H), 2.41 (s, 3H), 1.30 (s, 9H).

LCMS m/z 841 (M+H)⁺ (ES⁺); 421 (M+2H)²⁺ (ES⁺)

Example 7: 3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(2,5,8,11-tetraoxatridecan-13-yl)benzamide Example 8: 3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(2-(2-methoxyethoxy)ethyl)benzamide

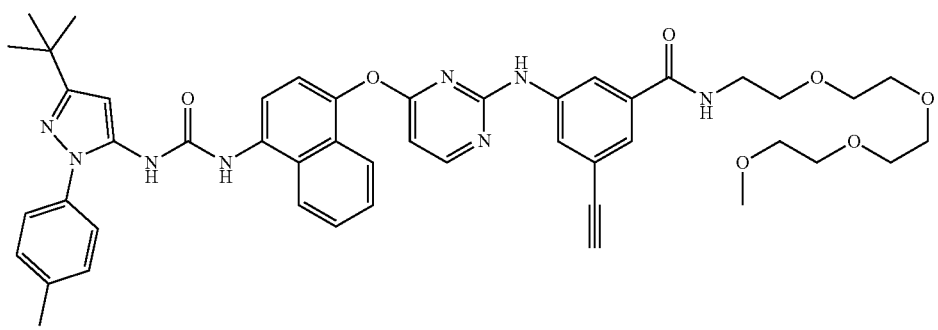 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCOCCOCCOCCOC)c1]

Et₃N (35 μL, 0.251 mmol) was added to a stirred solution of Intermediate A1* (400 mg, 1.144 mmol) and Intermediate B3 (670 mg, 1.144 mmol) in isopropyl acetate (30 mL). The mixture was heated at 50° C. for 8 h then cooled to rt and stirred overnight during which time a precipitate was formed. The solid was filtered off and washed with isopropyl acetate (15 mL) then dried to constant weight. The product

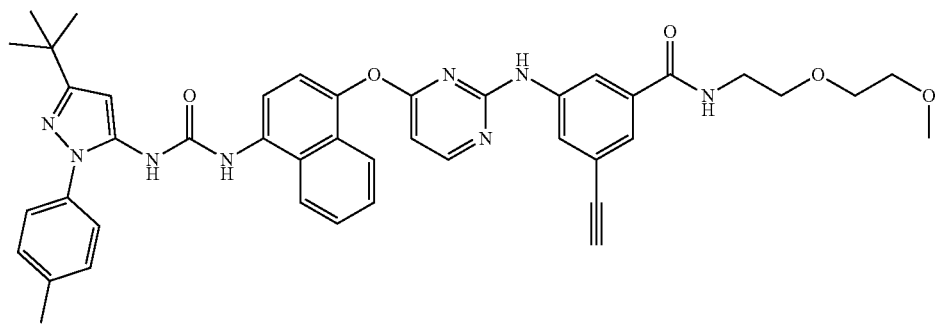 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCOCCOC)c1]

TEA (40.0 µl, 0.287 mmol) was added to a stirred solution of Intermediate A1* (525 mg, 1.502 mmol) and Intermediate B4 (700 mg, 1.407 mmol) in isopropyl acetate (20 mL). The mixture was heated at 50° C. for 18 h. The resulting precipitate was collected by filtration and washed with ethyl acetate (2×25 mL). The solid was recrystallised in acetonitrile to yield the title compound (571 mg) as a white solid.

$^1$H NMR (400 MHz, DMSO-d6) δ9.75 (s, 1H), 9.08 (s, 1H), 8.76 (s, 1H), 8.50-8.40 (m, 2H), 8.12-8.04 (m, 2H), 7.94 (d, 1H), 7.90-7.78 (m, 2H), 7.67-7.60 (m, 1H), 7.60-7.54 (m, 1H), 7.52-7.32 (m, 6H), 6.55 (d, 1H), 6.42 (s, 1H), 4.10 (s, 1H), 3.57-3.47 (m, 4H), 3.47-3.35 (m, 4H), 3.23 (s, 3H), 2.41 (s, 3H), 1.30 (s, 9H).

LCMS m/z 753 (M+H)$^+$ (ES$^+$); 751 (M−H)$^−$ (ES$^−$)

Example 9

3-((4-((4-(3-(3-(tert-Butyl)-1-(4-(dimethylamino) phenyl)-1H-pyrazol-5-yl)ureido)-naphthalen-1-yl) oxy)pyrimidin-2-yl)amino)-5-ethynyl-N-(2-(2-(2-methoxyethoxy)-ethoxy)ethyl)benzamide h. The resulting precipitate was collected by filtration then recrystallised in acetonitrile to yield the title compound (63 mg) as a white solid.

$^1$H NMR (DMSO-d6) 400 MHz, δ: 9.75 (s, 1H), 9.11 (s, 1H), 8.66 (s, 1H), 8.45 (dd, 1H), 8.44 (d, 1H), 8.11-8.04 (m, 2H), 7.96 (d, 1H), 7.87 (br s, 1H), 7.82 (dd, 1H), 7.63 (ddd, 1H), 7.57 (ddd, 1H), 7.45 (dd, 1H), 7.43 (d, 1H), 7.37-7.31 (m, 2H), 6.91-6.83 (m, 2H), 6.55 (d, 1H), 6.38 (s, 1H), 4.10 (s, 1H), 3.56-3.46 (m, 8H), 3.42-3.35 (m, 4H), 3.21 (s, 3H), 2.99 (s, 6H), 1.29 (s, 9H).

LCMS m/z 826 (M+H)$^+$ (ES$^+$)

Example 10

3-((4-((4-(3-(3-(tert-Butyl)-1-(4-(dimethylamino) phenyl)-1H-pyrazol-5-yl)ureido)-naphthalen-1-yl) oxy)pyridin-2-yl)amino)-5-methoxy-N-(2-(2-(2-methoxyethoxy)-ethoxy)ethyl)benzamide

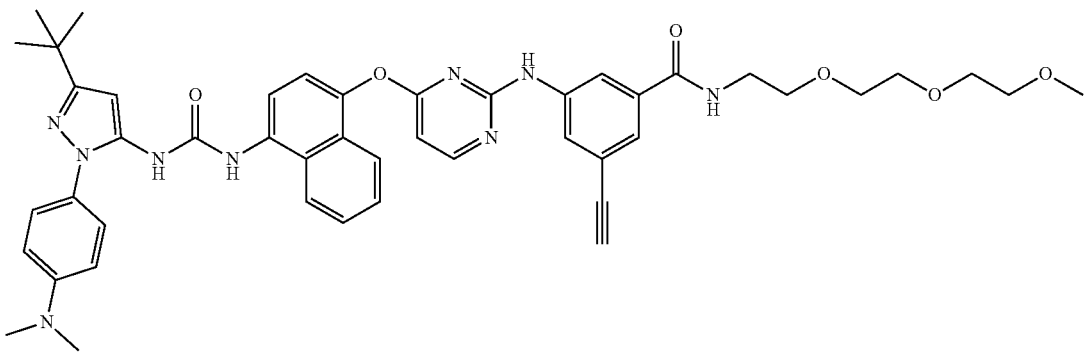

Intermediate A5* (80 mg, 0.211 mmol), Intermediate B2 (114 mg, 0.211 mmol) and Et$_3$N (10.00 µL, 0.072 mmol) were heated to 60° C. (block temp) in iPrOAc (3 mL) for 2

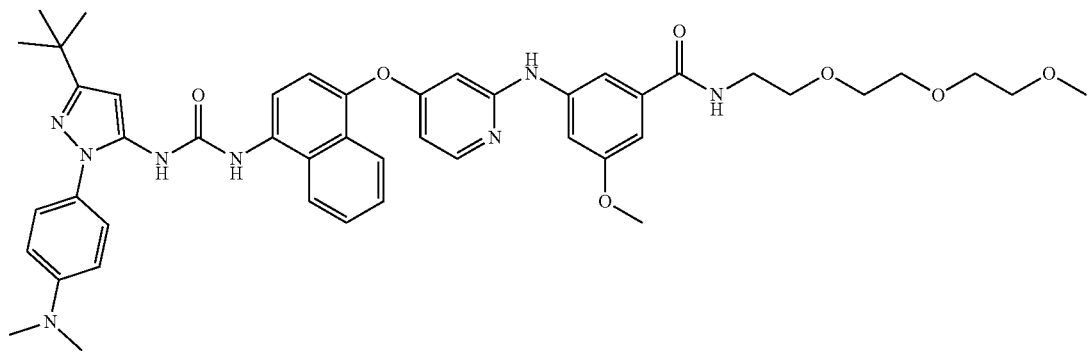

Intermediate A5* (80 mg, 0.211 mmol), Intermediate B1 (116 mg, 0.211 mmol) and Et₃N (10.00 µL, 0.072 mmol) were heated to 60° C. (block temp) in iPrOAc (3 mL) for 2 h. The mixture was concentrated under reduced pressure and the residue was purified by chromatography on the Companion (40 g column, 0-5% MeOH/DCM) to afford a gum. The gum was purified by preparative HPLC (Gilson, Acidic (0.1% Formic acid), Acidic, Waters X-Select Prep-C18, 5 µm, 19×50 mm column, 25-75% MeCN in Water). Fractions containing product were combined, concentrated under reduced pressure then redissolved in ethyl acetate (50 mL). The organic solution was washed with saturated NaHCO₃ solution (50 mL), saturated brine (50 mL), dried (MgSO₄) and concentrated under reduced pressure. The resulting foam was slurried in diethyl ether (5 mL) overnight then collected by filtration to afford the title compound (75 mg) as a white solid.

¹H NMR (DMSO-d6) 400 MHz, δ: 9.16 (s, 1H), 9.06 (s, 1H), 8.67 (s, 1H), 8.38-8.30 (m, 1H), 8.14-8.05 (m, 2H), 8.00 (d, 1H), 7.85 (d, 1H), 7.69-7.62 (ddd, 1H), 7.62-7.55 (m, 2H), 7.52-7.48 (m, 1H), 7.39-7.31 (m, 3H), 6.91-6.84 (m, 3H), 6.59-6.53 (dd, 1H), 6.38 (s, 1H), 6.13 (d, 1H), 3.75 (s, 3H), 3.56-3.47 (m, 8H), 3.43-3.35 (m, 4H), 3.21 (s, 3H), 2.99 (s, 6H), 1.28 (s, 9H).

LCMS m/z 831 (M+H)⁺ (ES⁺); 829 (M−H)⁻ (ES⁻)

Example 11

3-((4-((4-(3-(3-(tert-Butyl)-1-(4-(dimethylamino) phenyl)-1H-pyrazol-5-yl)ureido)-naphthalen-1-yl) oxy)pyridin-2-yl)amino)-5-ethynyl-N-(2-(2-(2-methoxyethoxy)ethoxy)-ethyl)benzamide µm, 19×50 mm column, 25-75% MeCN in Water). Fractions containing product were combined, concentrated under reduced pressure then redissolved in ethyl acetate (50 mL). The organic solution was washed with saturated NaHCO₃ carbonate solution (50 mL), saturated brine (50 mL), dried (MgSO₄) and concentrated under reduced pressure. The resulting foam was slurried in diethyl ether (5 mL) overnight then collected by filtration to afford the title compound (93 mg) as a white solid.

¹H NMR (DMSO-d6) 400 MHz, δ: 9.21 (s, 1H), 9.17 (s, 1H), 8.67 (s, 1H), 8.47 (dd, 1H), 8.14 (d, 1H), 8.13-8.07 (m, 2H), 8.00 (d, 1H), 7.93 (dd, 1H), 7.85 (d, 1H), 7.66 (ddd, 1H), 7.59 (ddd, 1H), 7.42 (dd, 1H), 7.38 (d, 1H), 7.36-7.31 (ddd, 2H), 6.91-6.84 (ddd, 2H), 6.61 (dd, 1H), 6.38 (s, 1H), 6.12 (d, 1H), 4.19 (s, 1H), 3.58-3.46 (m, 8H), 3.43-3.35 (m, 4H), 3.21 (s, 3H), 2.99 (s, 6H), 1.29 (s, 9H).

LCMS m/z 825 (M+H)⁺ (ES⁺); 823 (M−H)⁻ (ES⁻)

Example 12

3-((4-((4-(3-(3-(tert-Butyl)-1-(p-tolyl)-1H-pyrazol-5-yl)ureido)-5,6,7,8-tetrahydronaphthalen-1-yl)oxy) pyrimidin-2-yl)amino)-5-ethynyl-N-(2-(2-(2-methoxyethoxy)-ethoxy)ethyl)benzamide

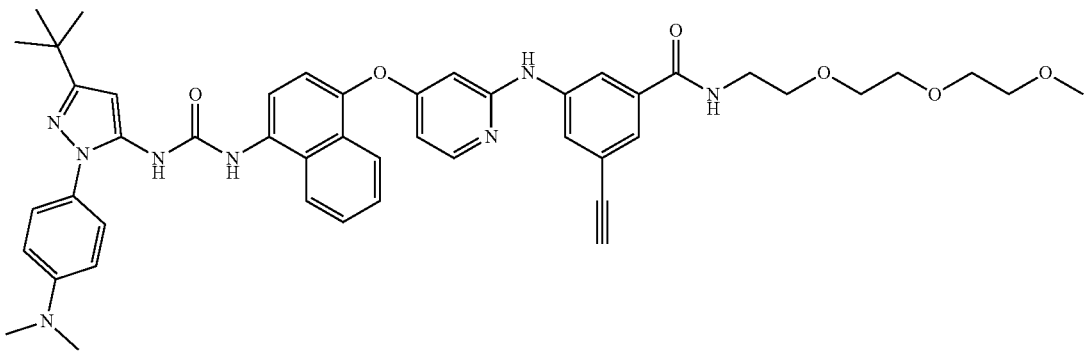

Intermediate A5* (80 mg, 0.211 mmol), Intermediate B5 (114 mg, 0.211 mmol) and Et₃N (10.00 µL, 0.072 mmol) were heated to 60° C. (block temp) in iPrOAc (3 mL) for 2 h. The mixture was concentrated under reduced pressure and the residue was purified by chromatography on the Companion (40 g column, 0-5% MeOH/DCM) to afford a gum. The gum was purified by preparative HPLC (Gilson, Acidic (0.1% Formic acid), Acidic, Waters X-Select Prep-C18, 5

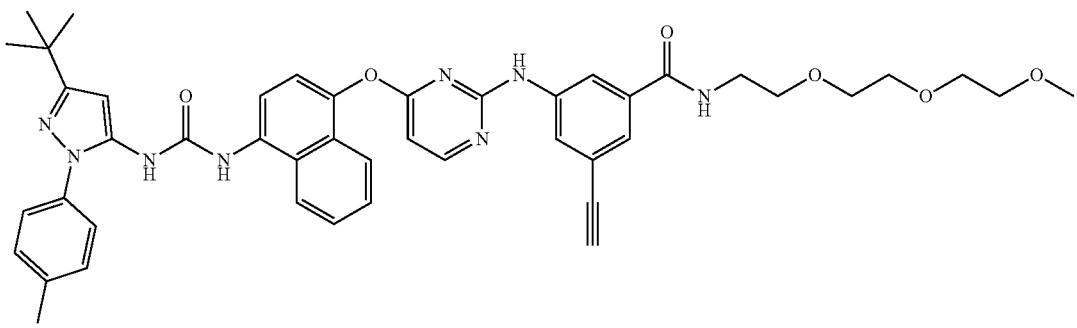 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCOCCOCCOC)c1]

A mixture of Intermediate C4(H) (250 mg, 0.471 mmol), Intermediate D2 (288 mg, 0.942 mmol) and pTSA monohydrate (20 mg, 0.105 mmol) in THF (8 mL) was heated at 60° C. for 6 h. The mixture was partitioned between EtOAc (60 mL) and aq 1M HCl (40 mL), the organic layer washed with brine (20 mL), dried (MgSO$_4$), filtered and evaporated under reduced pressure. The crude product was purified by chromatography on silica gel (40 g column, 0-5% MeOH/DCM) to give a solid that was triturated with MeCN to afford the title compound (136 mg) as a white solid.

$^1$H NMR (DMSO-d6) 400 MHz, δ: 9.79 (s, 1H), 8.68 (s, 1H), 8.47 (t, 1H), 8.38 (d, 1H), 8.14 (s, 1H), 8.09 (s, 1H), 7.95 (s, 1H), 7.59 (d, 1H), 7.47 (s, 1H), 7.42 (d, 2H), 7.35 (d, 2H), 6.97 (d, 1H), 6.40 (d, 1H), 6.35 (s, 1H), 4.11 (s, 1H), 3.55-3.48 (m, 8H), 3.43-3.37 (m, 4H), 3.22 (s, 3H), 2.39 (s, 3H), 1.75-1.60 (m, 4H), 1.28 (s, 9H). (4H under DMSO)

LCMS m/z 801 (M+H)$^+$ (ES$^-$)

Example 13

3-((4-((4-(3-(3-(tert-Butyl)-1-(2,4-dimethoxyphenyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)-benzamide by chromatography on silica gel (40 g column, 2% MeOH:DCM to 8%) to afford a yellow gum which was stirred in MeCN overnight. The resulting precipitate was filtered off and washed with MeCN (2 mL) to afford the title compound (240 mg) as a beige solid.

$^1$H NMR (400 MHz, DMSO-d6) δ 9.75 (s, 1H), 9.13 (s, 1H), 8.58-8.36 (m, 3H), 8.10-8.01 (m, 2H), 7.98 (d, 1H), 7.90-7.85 (m, 1H), 7.83 (d, 1H), 7.69-7.60 (m, 1H), 7.60-7.52 (m, 1H), 7.48-7.40 (m, 2H), 7.32 (d, 1H), 6.84 (d, 1H), 6.71 (dd, 1H), 6.55 (d, 1H), 6.37 (s, 1H), 4.08 (s, 1H), 3.88 (s, 3H), 3.84 (s, 3H), 3.55-3.46 (m, 8H), 3.39 (m, 4H), 3.21 (s, 3H), 1.27 (s, 9H).

LCMS m/z 843 (M+H)$^+$ (ES$^+$)

Example 14

3-((4-((4-(3-(3-(tert-Butyl)-1-(3-((dimethylphosphoryl)methyl)phenyl)-1H-pyrazol-5-yl)-ureido)naphthalen-1-yl)oxy)pyrimidin-2-yl)amino)-5-ethynyl-N-(2-(2-(2-methoxyethoxy)-ethoxy)ethyl)benzamide

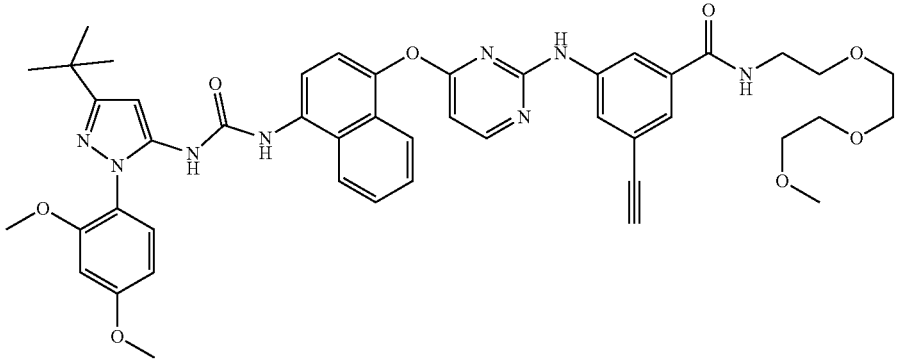 [SMILES: C#Cc1cc(Nc2nccc(Oc3ccc(NC(=O)Nc4cc(C(C)(C)C)nn4-c4ccc(OC)cc4OC)c4ccccc34)n2)cc(C(=O)NCCOCCOCCOC)c1]

DPPA (160 μL, 0.742 mmol) was added to a stirred solution of Intermediate M2 (210 mg, 0.690 mmol) and triethylamine (240 μL, 1.725 mmol) in DMF (3 mL). The reaction was stirred at rt for 1 h before addition of Intermediate B2 (350 mg, 0.646 mmol) and heating to 100° C. for 2 h. The reaction mixture was cooled and partitioned between EtOAc (20 mL) and 20% w/w NaCl soln. (40 mL). The organics were separated, dried (MgSO$_4$), filtered and evaporated to a brown gum. The crude product was purified

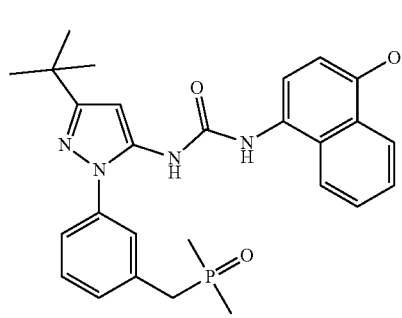
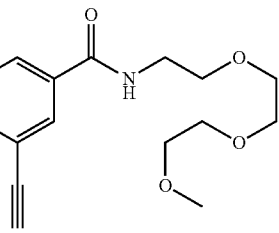

DPPA (80 μL, 0.371 mmol) was added to a solution of Intermediate M5 (110 mg, 0.329 mmol) and triethylamine (120 μL, 0.861 mmol) in DMF (2 mL). The reaction was stirred at rt for 1 h before addition of Intermediate B2 (170 mg, 0.314 mmol) and heating at 100° C. (block temperature) for 2 h. The reaction mixture was cooled and partitioned between EtOAc (20 mL) and 20% w/w NaCl soln. (40 mL). The organics were separated, dried (MgSO$_4$), filtered and evaporated to a brown gum. The crude product was purified by chromatography on silica gel (40 g column, 2% MeOH: DCM to 8%) to afford a beige solid which was recrystallised from MeCN (3 mL) to afford the title compound (80 mg) as a colourless solid.

$^1$H NMR (400 MHz, DMSO-d6) δ 9.75 (s, 1H), 9.42 (s, 1H), 8.95 (s, 1H), 8.52-8.36 (m, 2H), 8.21 (d, 1H), 8.07 (s, 1H), 8.00 (d, 1H), 7.92-7.77 (m, 2H), 7.70-7.51 (m, 4H), 7.52-7.38 (m, 3H), 7.32 (d, 1H), 6.56 (d, 1H), 6.51 (s, 1H), 4.10 (s, 1H), 3.56-3.45 (m, 8H), 3.44-3.35 (m, 6H), 3.21 (s, 3H), 1.47 (d, 6H), 1.31 (s, 9H).

LCMS m/z 873 (M+H)$^+$ (ES$^+$)

Example 15

3-((4-((4-(3-(3-(tert-Butyl)-1-(3-(((dimethylphosphoryl)methyl)phenyl)-1H-pyrazol-5-yl)-ureido)naphthalen-1-yl)oxy)pyridin-2-yl)amino)-5-methoxy-N-(2-(2-(2-methoxyethoxy)-ethoxy)ethyl)benzamide evaporated to a brown gum. The crude product was purified by chromatography on silica gel (40 g column, 2% MeOH: DCM to 8%) to afford a beige solid which was recrystallised from MeCN (3 ml) to afford the title compound (70 mg) as a tan solid.

$^1$H NMR (400 MHz, DMSO-d6) δ 9.48 (s, 1H), 9.07 (s, 1H), 8.96 (s, 1H), 8.34 (t, 1H), 8.24 (d, 1H), 8.11 (d, 1H), 8.03 (d, 1H), 7.86 (d, 1H), 7.71-7.63 (m, 1H), 7.63-7.44 (m, 6H), 7.36 (d, 1H), 7.35-7.29 (m, 1H), 6.89 (dd, 1H), 6.57 (dd, 1H), 6.51 (s, 1H), 6.12 (d, 1H), 3.74 (s, 3H), 3.57-3.46 (m, 8H), 3.43-3.35 (m, 6H), 3.21 (s, 3H), 1.47 (d, 6H), 1.31 (s, 9H).

LCMS m/z 878 (M+H)$^+$ (ES$^+$)

Example 16

3-((4-((4-(3-(3-(tert-Butyl)-1-(4-(dimethylamino) phenyl)-1H-pyrazol-5-yl)ureido)-naphthalen-1-yl) oxy)pyrimidin-2-yl)amino)-5-methoxy-N-(2-(2-(2-methoxyethoxy)-ethoxy)ethyl)benzamide

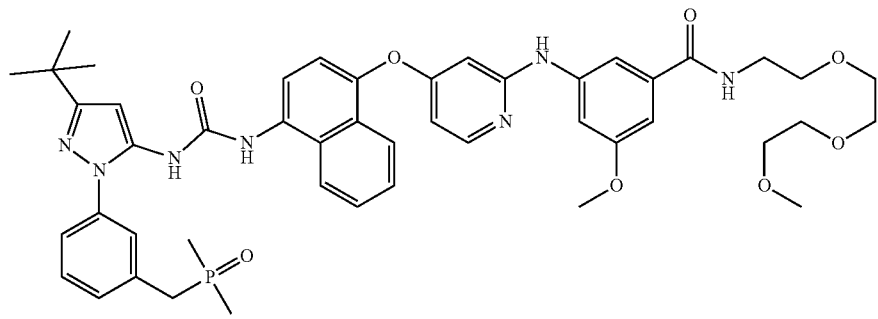 [SMILES: COCCOCCOCCNC(=O)c1cc(Nc2cc(Oc3ccc(NC(=O)Nc4cc(C(C)(C)C)nn4-c4cccc(CP(C)(C)=O)c4)c4ccccc34)ccn2)cc(OC)c1]

DPPA (80 μL, 0.371 mmol) was added to a solution of Intermediate M5 (112 mg, 0.335 mmol) and triethylamine (120 μL, 0.861 mmol) in DMF (2 mL). The reaction was stirred at rt for 1 h before addition of Intermediate B1 (170 mg, 0.311 mmol) and heating at 100° C. (block temperature) for 2 h. The reaction mixture was cooled and partitioned between EtOAc (20 mL) and 20% w/w NaCl soln. (40 mL). The organics were separated, dried (MgSO$_4$), filtered and

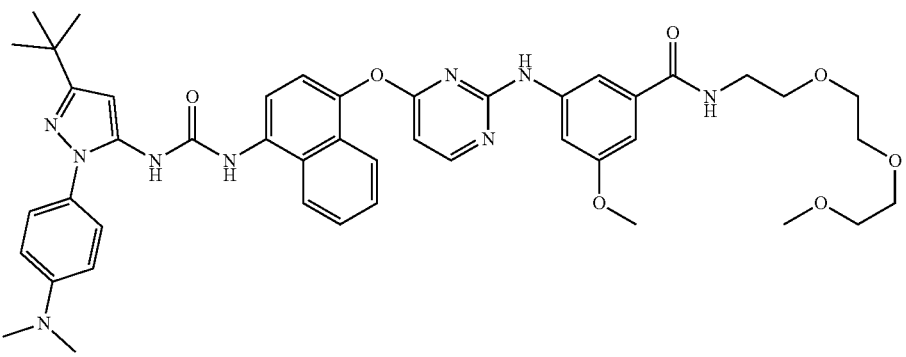 [SMILES: COCCOCCOCCNC(=O)c1cc(Nc2nccc(Oc3ccc(NC(=O)Nc4cc(C(C)(C)C)nn4-c4ccc(N(C)C)cc4)c4ccccc34)n2)cc(OC)c1]

Intermediate A5* (70 mg, 0.185 mmol), Intermediate B6 (101 mg, 0.185 mmol) and Et₃N (10 μL, 0.072 mmol) were heated to 60° C. (block temperature) in isopropyl acetate (6 mL) and stirred for 2 h. The cooled, gelatinous mixture was diluted with acetonitrile (6 mL) and the resulting solid was collected by filtration to yield a white solid. The solid was purified by preparative HPLC (Gilson, Acidic (0.1% Formic acid), Acidic, Waters X-Select Prep-C18, 5 μm, 19×50 mm column, 5-95% MeCN in Water). Colourless needles formed in the fractions over 72 h, which were collected by filtration to afford the title compound (63 mg) as a colourless crystalline solid.

¹H NMR (400 MHz, DMSO-d6) δ: 9.61 (s, 1H), 9.15 (br s, 1H), 8.71 (br s, 1H), 8.41 (d, 1H), 8.32 (dd, 1H), 8.08 (d, 1H), 7.98 (d, 1H), 7.82 (d, 1H), 7.62 (ddd, 1H), 7.59-7.53 (m, 2H), 7.41 (d, 1H), 7.38-7.30 (m, 3H), 6.91-6.83 (m, 3H), 6.53 (d, 1H), 6.38 (s, 1H), 3.59-3.55 (m, 2H), 3.54-3.46 (m, 8H), 3.41-3.37 (m, 2H), 3.20 (s, 3H), 2.98 (s, 6H), 2.08 (s, 3H), 1.28 (s, 9H).

LCMS m/z 832 (M+H)⁺ (ES⁺); 830 (M−H)⁻ (ES⁻)

Example 17

3-((4-((4-(3-(3-(tert-Butyl)-1-(4-methoxy-2-methyl-phenyl)-1H-pyrazol-5-yl)ureido)-naphthalen-1-yl)oxy)pyrimidin-2-yl)amino)-5-ethynyl-N-(2-(2-(2-methoxyethoxy)-ethoxy)ethyl)benzamide

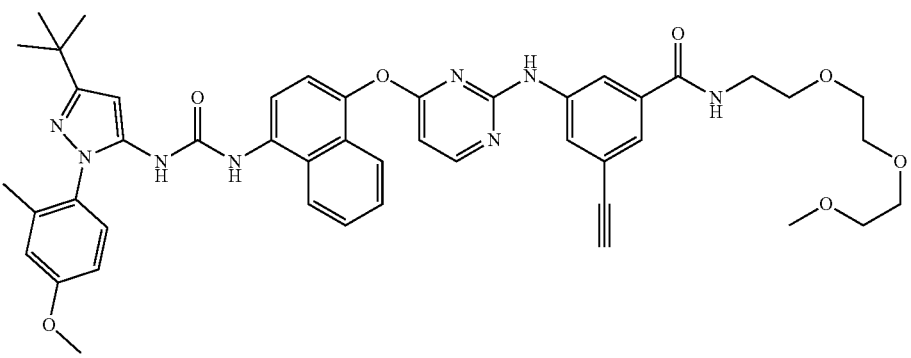 [SMILES: C#Cc1cc(Nc2nccc(Oc3ccc(NC(=O)Nc4cc(C(C)(C)C)nn4-c4ccc(OC)cc4C)c4ccccc34)n2)cc(C(=O)NCCOCCOCCOC)c1]

The title compound was prepared by methods analogous to those described above.

¹H NMR (DMSO-d6) 400 MHz, δ: 9.74 (s, 1H), 9.09 (s, 1H), 8.58 (s, 1H), 8.43-8.46 (m, 2H), 8.07 (s, 1H), 8.02 (d, 1H), 7.95 (d, 1H), 7.87 (s, 1H), 7.81 (d, 1H), 7.53-7.63 (m, 2H), 7.44 (s, 1H), 7.42 (d, 1H), 7.34 (d, 1H), 7.04 (d, 1H), 6.96 (dd, 1H), 6.55 (d, 1H), 6.38 (s, 1H), 4.09 (s, 1H), 3.85 (s, 3H), 3.48-3.51 (m, 8H), 3.37-3.41 (m, 4H), 3.21 (s, 3H), 2.02 (s, 3H), 1.29 (s, 9H).

LCMS m/z 827 (M+H)⁺ (ES⁺)

Biological Testing: Experimental Methods

Enzyme Binding Assays (Kinomescan)

Kinase enzyme binding activities of compounds disclosed herein may be determined using a proprietary assay which measures active site-directed competition binding to an immobilized ligand (Fabian, M. A. et al., Nature Biotechnol., 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants are used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5

μL) of the p38α inactive target MAPKAP-K2 (Invitrogen, 600 ng/mL) and FRET peptide (8 μM; a phosphorylation target for MAPKAP-K2) is then added and the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 μg/mL, 0.4 μg/mL, 0.04 μg/mL, or 0.004 μg/mL, 2.5 μL each) for 2 hr at RT. The FRET peptides (8 μM. 2.5 μL), and appropriate ATP solutions (2.5 μL, 800 μM for c-Src, and 60 μM ATP for Syk) are then added to the enzymes/compound mixtures and incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The following two assay variants are used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays (a) LPS-Induced TNFα/IL-8 Release in d-U937Cells

U937 cells, a human monocytic cell line, are differentiated into macrophage-type cells by incubation with PMA (100 ng/mL) for 48 to 72 hr. Cells are pre-incubated with final concentrations of test compound for 2 hr and are then stimulated with LPS (0.1 μg/mL; from *E. Coli: O*111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/ml LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, Thermo-Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 ug/ml eBioscience and 3 ug/ml BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/ml of IL-1β (Abeam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/ml of GM-CSF (Peprotech) for 7 days under normal tissue culture conditions. Compounds are then added to the cells at the desired concentration for a 2 hour pre-treatment before stimulation with 10 ng/ml LPS for 24 hours. Supernatants are harvested and IL-8 and TNFα release determined by Sandwich ELISA (Duo-set, R&D System). The $IC_{50}$ is determined from the dose response curve.

(f) Poly I: C-Induced ICAM-1 Expression in BEAS2B Cells

Poly I:C is used in these studies as a simple, RNA virus mimic Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS (100 μL) and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL). and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with of substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2\times10^5$ cells per well in 100 μL RPMI/10% FBS on 96 well flat bottomed plate (Corning Costar). 25 μL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 hours before stimulation with 1 μg/mL anti-CD3 (OKT3; eBioscience). After 72 h, the medium in each well is replaced with 150 μL of fresh medium containing 10 μM BrdU (Roche). After 16 h, the supernatant is removed, the plate is dried and the cells fixed by adding 100 μL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 μL of substrate solution. The reaction is stopped by addition of 50 μL of 1 M $H_2SO_4$, and read for absorbance at 450 nm on a plate reader (Varioskan® Flash, ThermoFisher Scientific). The $IC_{50}$ is determined from the dose response curve.

(h) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(i) Cell Mitosis Assay

PBMCs from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (Sigma-Aldrich, Poole, UK) for 48 hr, followed by a 20 hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(j) Assessment of HRV16 Induced CPE in MRC5 Cells

MRC-5 cells are infected with HRV16 at an MOI of 1 in DMEM containing 5% FCS and 1.5 mM magnesium chloride, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(k) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 μL), fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No.ab43812, Abcam) in 5% BSA in PBS-tween. After washing, cells are incubated with an HRP-conjugated secondary antibody solution (50 µL) in 5% BSA in PBS-Tween (lot 00053170, Cat. No. P0447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(l) The Effect of Test Compounds on Cell Viability: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(m) Accumulation of β Catenin in d-U937Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL; PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide) (1 µg/mL) which is defined as 100%.

(n) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2\times10^5$ cells/well) are stimulated with 1 µg/mL α-CD3/α-CD28 for 48 h in the presence of either DMSO control or appropriate concentrations of compound.

After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(o) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3\times10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(p) Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+(Hanks buffered salt solution (without phenol red) containing cytochalasin B (5 µg/mL) and 1 mM $CaCl_2$) to achieve $5 \times 10^6$ cells/mL.

$5 \times 10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(q) Cell Cytotoxicity Assay $5 \times 10^4$ TK6 cells (lymphoblastic T cell line) are added to the appropriate number of wells of a 96 well plate in 195 µL of media (RPMI supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 hours, the plate is centrifuged at 1300 rpm for 3 minutes and the supernatant discarded. Cells are then resuspended in 7.5 µg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (A) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(B) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(C) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 µL) is administered intra-colonically via a plastic catheter with BID dosing of the vehicle, reference or test compound continuing for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for histopathology scoring to determine disease severity.

(D) Adoptive Transfer in Mice

On Study day 0, female Balb/C mice are terminated and spleens obtained for $CD45RB^{high}$ cell isolation (Using SCID IBD cell Separation protocol). Approximately $4 \times 10^5$ cells/mL $CD45RB^{high}$ cells are then injected IP (100 µL/mouse) into female SCID animals. On study day 14, mice are weighed and randomized into treatment groups based on body weight. On Day 14 compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

(E) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(F) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker and receive a single intravitreal administration into the right vitreous humor (5 μL dose volume) of 100 ng/animal, i.v.t. of LPS (*Escherichia coli* 0111:B4 prepared in PBS, Sigma Aldrich, UK) using a 32-gauge needle. Untreated rats are injected with PBS. Test compound, dexamethasone (Dex) or vehicle (20% hydroxypropyl-β-cyclodextrin, 0.1% HPMC, 0.01% Benzalconium chloride, 0.05% EDTA, 0.7% NaCl in deionised water) are administered by the topical route onto the right eye (10 μL) of animals 30 minutes prior to LPS, at the time of LPS administration, and 1, 2 and 4 hours post LPS administration. Before administration, the solution or suspension to be administered is agitated for 5 minutes to ensure a uniform suspension. 6 hours after LPS dosing, animals are euthanized by overdose with pentobarbitone (i.v.). Following euthanasia, the right eye of each animal is enucleated and dissected into front (anterior) and back (posterior) sections around the lens. Each section is weighed and homogenised in 500 μL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

Studies conducted by LeadHunter Discover Services (DiscoveRx Corporation, Fremont, Calif.) using the KINO-MEscan™ technology determined that compound of Example 2 did not have any effect on the binding of the kinases B-Raf and B-Raf (V600e) to their standard ligands.

TABLE 3

KinomeScan Selectivity score data for the Reference Compound and the compound of Example 2 at 50 and 500 nM

| | KinomeScan Selectivity Scores/number of hits | | | | | |
|---|---|---|---|---|---|---|
| | 50 nM | | | 500 nM | | |
| Compound | S(35) | S(10) | S(1) | S(35) | S(10) | S(1) |
| Reference Compound | 0.174/67 | 0.083/32 | 0.018/7 | 0.370/143 | 0.272/105 | 0.117/45 |
| Ex. 2 | 0.081/32 | 0.020/8 | 0.000/0 | 0.233/92 | 0.099/39 | 0.010/4 |

The in vitro profile of the compound examples of the present invention, as determined using the protocols described above, are presented below (Tables 3a and 3b).

TABLE 3a

The p38 MAPK (Method 2), c-Src, Syk and GSK3α (Method 2) Enzyme Profiles of Compound Examples

| Test Compound | IC$_{50}$ Values for Enzyme Inhibition (nM) | | | |
|---|---|---|---|---|
| Example No. | p38 MAPKα | c-Src | Syk | GSK3α |
| 1 | 25 | 30 | 370 | 12773 |
| 2 | 52 | 11 | 50 | 3849 |
| 3 | 39 | 14 | 30 | 12159 |
| 4 | 50 | 19 | 46 | 9547 |
| 5 | 33 | 13 | 34 | 13006 |
| 6 | 42 | 17 | 96 | 1695 |
| 7 | 88 | 18 | 237 | 2020 |
| 8 | 104 | 20 | 120 | 2890 |
| 9 | 98 | 15 | 35 | 12107 |
| 10 | 110 | 25 | 48 | 12034 |
| 11 | 766 | >1212 | >1212 | 12122 |
| 12 | NT | NT | NT | 12485 |
| 13 | 370 | 21 | 123 | 2129 |
| 14 | 88 | 4 | 20 | 402 |
| 15 | 34 | 18 | 57 | 3196 |
| 16 | NT | 15 | 27 | 646 |
| 17 | NT | NT | NT | 12093 |

TABLE 3b

Inhibition of cytokine release in stimulated cells (assays (a), (b), (c) and (d) above)

| Test Compound | IC$_{50}$ Values for Inhibition of Cytokine Release (nM) | | | | | | |
|---|---|---|---|---|---|---|---|
| | dU937 cells | | PBMCs | | | | HT29 cells |
| Example No. | IL-8 | TNFα | IL-8 | TNFα | IL-2 | IFNγ | IL-8 |
| 1 | NT | NT | 1.6 | NT | NT | NT | NT |
| 2 | 0.5 | 0.5 | 2.0 | 0.7 | 44.2 | 2.5 | 3.3 |
| 3 | NT | NT | 1.2 | NT | 7.5 | 2.0 | NT |
| 4 | NT | NT | 1.4 | NT | 37.4 | 2.4 | 5.3 |
| 5 | NT | NT | 1.2 | NT | 52.1 | 1.7 | NT |
| 6 | NT | NT | 2.3 | NT | 123.3 | 2.9 | 2.4 |
| 7 | NT | NT | 2.4 | NT | 91.0 | 3.7 | 1.6 |
| 8 | NT | NT | 1.6 | NT | 55.0 | 8.5 | 3.2 |
| 9 | NT | NT | 2.9 | NT | NT | 8.4 | 3.5 |
| 10 | NT | NT | 3.3 | NT | NT | 2.7 | 4.8 |
| 11 | NT | NT | 4.3 | NT | NT | NT | 6.2 |

TABLE 3b-continued

Inhibition of cytokine release in stimulated cells
(assays (a), (b), (c) and (d) above)

IC$_{50}$ Values for Inhibition of Cytokine Release (nM)

| Test Compound Example No. | dU937 cells IL-8 | dU937 cells TNFα | PBMCs IL-8 | PBMCs TNFα | PBMCs IL-2 | PBMCs IFNγ | HT29 cells IL-8 |
|---|---|---|---|---|---|---|---|
| 12 | NT | NT | 11.8 | NT | NT | NT | 10.9 |
| 13 | NT | NT | 4.6 | NT | NT | NT | 3.6 |
| 14 | NT | NT | 1.5 | NT | NT | NT | 1.5 |
| 15 | NT | NT | 1.2 | NT | NT | NT | 2.0 |
| 16 | NT | NT | 2.7 | NT | NT | NT | NT |
| 17 | NT | NT | 5.0 | NT | NT | NT | NT |

In addition to the above:

when studied in assay (e) above, the compound of Example 2 exhibited IC$_{50}$ values of 2.1 and 2.8 nM for inhibition of release of IL-8 and IL-6, respectively;

when studied in assay (g) above, the compound of Example 2 exhibited an IC$_{50}$ values of 2.7 nM for inhibition of T cell proliferation; and when studied in assay (p) above (neutrophil degranulation), the compound of Example 2 exhibited an IC$_{50}$ of 42.7 nM (an average of 3 experiments).

As illustrated in Table 4a, compounds of the examples of the present invention are markedly less active than the Reference Compound in assay (i) above, which measures impact on cell division (mitosis) in PBMCs.

TABLE 4a

Effect of compounds of the examples on cell division in PBMCs

| Test compound | % Inhibition of mitosis at 5 µg/mL |
|---|---|
| Reference compound | 87.8$^a$ |
| 1 | 3.6 |
| 2 | 18.7 |
| 3 | 2.1 |
| 4 | 38.8 |
| 5 | 10.4 |
| 6 | 10.2 |
| 7 | 9.1 |
| 8 | 6.1 |
| 9 | NT |
| 10 | NT |
| 11 | NT |
| 12 | NT |
| 13 | NT |
| 14 | NT |
| 15 | NT |
| 16 | NT |
| 17 | NT |

$^a$See, for example, the value reported in WO 2013/050757.
(NT = not tested)

As illustrated in Table 4b, compounds of the examples of the present invention did not elicit any significant β-catenin induction when studied in assay (m) above. Thus, the potential of those compounds to increase cellular concentrations of β-catenin was found to be negative in that their inductive effect at various test concentrations was substantially less than the effect produced by the Reference Compound at 1 µg/mL.

TABLE 4b

Effect of compounds of the examples on β-catenin induction

| Test compound | % β-catenin induction 1 µg/mL | % β-catenin induction 5 µg/mL | % β-catenin induction 10 µg/mL |
|---|---|---|---|
| Reference compound | 100 | NT | NT |
| 1 | −14 | −13 | −17 |
| 2 | 0 | 2 | 0 |
| 3 | 1 | 6 | 6 |
| 4 | 5 | 12 | NT |
| 5 | 8 | 2 | 3 |
| 6 | 3 | 3 | −1 |
| 7 | 0 | −2 | −5 |
| 8 | 6 | 3 | 2 |
| 9 | 1 | 2 | 4 |
| 10 | 4 | 2 | 2 |
| 11 | NT | NT | NT |
| 12 | NT | NT | NT |
| 13 | −5 | −2 | −4 |
| 14 | NT | NT | NT |
| 15 | 4 | 11 | 27 |
| 16 | NT | NT | NT |
| 17 | NT | NT | NT |

(NT = not tested)

When studied in assay (q) above (cell cytotoxicity), percentage cell viability relative to DMSO control was measured as 101% at 5 µg/mL and 103% at 1 µg/mL of the compound of Example 2. Thus, that compound does not exhibit any cytotoxicity in assay (q). By comparison, percentage cell viability relative to DMSO control was measured for the Reference Compound as 43% at 5 µg/mL and 49% at 1 µg/mL.

As illustrated in Tables 5a, 5b1 and 5b2 below, the compound of Example 2 was also screened in human biopsy assay (h) and in vivo assay (C) above, as conducted over 2 days. Histopathology analysis revealed that the compound of Example 2 displayed significant activity in the in vivo model of colonic inflammation. In particular, that compound, when dosed orally at 5 mg/kg, demonstrated marked improvements in ulcer grade and epithelial repair compared to the vehicle control. In addition, the compound of Example 2 produced marked reduction in inflammatory cell infiltrate in the reticular and lamina propria zones. The compound of Example 2 also demonstrated marked anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Addition of the compound of Example 2 to biopsies in vitro markedly reduced IL-1β, IL-6 and IL-8 release.

TABLE 5a

Summary of results from studies on TNBS-induced colitis in mice.

| Experiment no. | Treatment group | n | TNBS Ulcer grade | TNBS LP inflammation |
|---|---|---|---|---|
| 1 | Non-diseased | 6 | 0.0 ± 0.0 | 0.2 ± 0.2 |
| 1 | TNBS + Vehicle | 24 | 4.4 ± 0.2# | 4.5 ± 0.2# |
| 1 | TNBS + Example 2 (1 mg/kg) | 12 | 3.5 ± 0.4 | 2.9 ± 0.3* |
| 1 | TNBS + Example 2 (5 mg/kg) | 12 | 3.0 ± 0.5* | 2.2 ± 0.4* |

TABLE 5a-continued

Summary of results from studies on TNBS-induced colitis in mice.

| Experiment no. | Treatment group | n | TNBS Ulcer grade | LP inflammation |
|---|---|---|---|---|

P < 0.001 compared to non-diseased animals
*p < 0.05 relative to vehicle control TABLE 5b1

Summary of results from assays using intestinal mucosa biopsies from the inflamed regions of the colon of various patients suffering from ulcerative colitis (a form of IBD).

| Treatment group | n | IL-1β release | n | IL-6 release | n | IL-8 release |
|---|---|---|---|---|---|---|
| DMSO control | | 100% | | 100% | | 100% |
| Example 2 (1 μg/mL) | 4 | 4 ± 10 | 6 | 29 ± 30 | 6 | 21 ± 21 |

TABLE 5b2

Summary of results from further assays using intestinal mucosa biopsies from the inflamed regions of the colon of various patients suffering from ulcerative colitis (a form of IBD).

| Treatment group | n | TNFα release | n | IL-1β release | n | IL-6 release | n | IL-8 release |
|---|---|---|---|---|---|---|---|---|
| DMSO control | | 100% | | 100% | | 100% | | 100% |
| Example 2 (1000 ng/mL) | 2 | 10 ± 3 | 2 | 9 ± 5 | 4 | 6 ± 3 | 4 | 3 ± 0.1 |
| Example 2 (100 ng/mL) | 2 | 17 ± 1 | 2 | 2 ± 0.1 | 4 | 18 ± 4 | 4 | 19 ± 7 |
| Example 2 (10 ng/mL) | 2 | 27 ± 17 | 2 | 2 ± 2 | 4 | 40 ± 23 | 4 | 71 ± 30 |
| Example 2 (3 ng/mL) | 2 | 48 ± 9 | 2 | 34 ± 4 | 4 | 34 ± 9 | 4 | 41 ± 14 |

As illustrated in Tables 5c and 5d below, the compound of Example 2 was also screened in cellular assays (n) and (o) above. In these assays, the compound of Example 2 displayed significant inhibition of cytokines from cells isolated from diseased (IBD) patients. Negative values reported in Table 5d are indicative of inhibition of the basal expression of cytokines by the compound of Example 2.

TABLE 5c

Summary of results from assays using LPMCs from IBD patients.

| Treatment group | n | IFNγ release | n | TNFα release |
|---|---|---|---|---|
| | | Cytokine release from LPMCs of IBD patients (% release relative to DMSO control) | | |
| DMSO control | | 100 | | 100 |
| Example 2 (1000 ng/mL) | 1 | 2 | 1 | 0 |
| Example 2 (100 ng/mL) | 1 | 1 | 1 | 2 |
| Example 2 (10 ng/mL) | 1 | 9 | 1 | 2 |
| Example 2 (1 ng/mL) | 1 | 8 | 1 | 12 |
| Example 2 (0.3 ng/mL) | 1 | 20 | 1 | 35 |

TABLE 5d

Summary of results from assays using LPMCs from IBD patients.

| Treatment group | n | IL-8 release | n | IL-6 release |
|---|---|---|---|---|
| | | Cytokine release from myofibroblasts of IBD patients (% release relative to DMSO control) | | |
| DMSO control | | 100 | | 100 |
| Example 2 (100 ng/mL) | 2 | −72 ± 34 | 2 | −21 ± 8 |
| Example 2 (10 ng/mL) | 2 | −52 ± 22 | 2 | −12 ± 4 |
| Example 2 (1 ng/mL) | 2 | 66 ± 147 | 2 | 82 ± 105 |

As illustrated in Table 6 below, the compound of Example 2 was also screened in the in vivo (adoptive transfer) assay (D) above. Histopathology analysis, as well as analysis of the relative inhibition of cytokine release revealed that the compound of Example 2 also displayed significant activity in this further in vivo model of colonic inflammation.

TABLE 5

Summary of results from adoptive transfer mouse model.

| | Dose of compound of Example 2 (mg/kg) | | | |
|---|---|---|---|---|
| | 5 | 1 | 0.2 | 0.04 |
| % Inhibition of colon weight:length | 61%* | 43%# | 23% | 25%# |
| % inhibition of IL-8 release | 90%# | 36%# | 39% | 34%# |
| % inhibition of overall histopathology score | 46% | 33% | 5% | 2% |

*P < 0.05 ANOVA to vehicle
p < 0.05 T-test to vehicle

Summary of Additional Studies
Determination of Pharmacokinetic Parameters
(i) Studies in Mice A study was conducted by Sai Life Sciences (Hinjewadi, Pune, India) to investigate the pharmacokinetics and total colon tissue distribution of the compound of Example 2 in male C57BL/6 mice following a single oral administration.

A group of twenty one male mice were dosed with a suspension formulation (in peanut oil) of the compound of Example 2, at a dose of 5 mg/kg. Blood samples (approximately 60 μL) were collected from retro orbital plexus such that the samples were obtained at 1, 2, 4, 6, 8, 12 and 24 hr. The blood samples were collected from a set of three mice at each time point in labelled micro centrifuge tube containing $K_2EDTA$ as anticoagulant. Plasma samples were separated by centrifugation at 4000 rpm for 10 min of whole blood and stored below −70° C. until bioanalysis. After collection of blood sample, animals were humanely euthanized by carbon dioxide asphyxiation to collect total colon tissues. The colons were flushed with cold phosphate buffer saline (pH 7.4) to remove contents. The total colon tissues were homogenized with cold phosphate buffer saline (pH 7.4) of twice the weight of colon tissue and stored below −70° C. Total volume was three times the total colon tissue weights. All samples were processed for analysis by protein precipitation using acetonitrile and analyzed with developed LC-MS/MS method (LLOQ: 2.02 ng/mL in plasma and 1.01 ng/mL in colon tissue). Pharmacokinetic parameters were calculated using the non-compartmental analysis tool of Phoenix WinNonlin® software (version 6.3).

(II) Studies in Rats

A study was conducted by Sai Life Sciences (Hinjewadi, Pune, India) to investigate the pharmacokinetics, as well as plasma and total colon tissue distribution of the compound of Example 2 in male Wistar rats following a single intravenous or oral administration.

30 male Wistar rats were divided into two groups: Group I (p.o.: 5 mg/kg) and Group II (i.v.: 0.25 mg/kg). Animals in Group I were administered orally with an aqueous suspension formulation (having 2% HPMC and 0.5% Tween 80) of the compound of Example 2, at a dose of 5 mg/kg. Animals in Group II were administered intravenously with a solution formulation (in 5% v/v DMSO, 7.5% w/v Solutol HS 15 and 87.5% saline (0.9% w/v NaCl)) of the compound of Example 2 at a dose of 0.25 mg/kg. From each rat, blood samples (approximately 120 μL) were collected from retro orbital plexus such that samples were obtained at pre-dose, 0.05, 0.13, 0.25, 0.5, 1, 2, 4, 8, and 24 hr (i.v.) and pre-dose, 0.5, 1, 2, 4, 6, 8, 12 and 24 hr (p.o.). Immediately after collection, plasma was harvested from blood by centrifugation and stored at −70° C. until analysis. Following collection of blood sample, the animals (Group I) were humanely euthanized by carbon dioxide asphyxiation. The total colon was isolated, flushed with cold phosphate buffer saline (pH 7.4) to remove contents and weighed. The total colon tissues homogenized with ice-cold phosphate buffered saline, pH 7.4. Buffer volume to be used for homogenization was twice the weight of tissue. All the samples were stored below −70° C. until bioanalysis. Total colon tissue homogenate volume was three times. Plasma and total colon tissue samples were quantified by LC-MS/MS method (LLOQ in plasma and total colon tissue=0.5 ng/mL).

(II) Studies in Beagle Dogs

A study was conducted by Sai Life Sciences (Hinjewadi, Pune, India) to investigate the plasma pharmacokinetics of the compound of Example 2 in male beagle dogs following a single intravenous or oral administration.

A group of three male beagle dogs were administered orally with an aqueous suspension formulation (having 2% HPMC and 0.5% Tween 80) of the compound of Example 2, at a dose of 1 mg/kg. A group of three male beagle dogs were administered intravenously with a solution formulation (in 5% v/v DMSO, 7.5% w/v Solutol HS 15 and 87.5% saline (0.9% w/v NaCl)) of the compound of Example 2, at a dose of 0.05 mg/kg. Blood samples (approximately 1.5 mL) were collected from jugular vein such that the samples were obtained at pre-dose, 0.25, 0.5, 1, 2, 4, 6, 8, and 24 hr (p.o.) and pre-dose, 0.08, 0.25, 0.5, 1, 2, 4, 8, 12, 24 and 32 hr (i.v.) post dose. The blood samples were collected from a set of three dogs at each time point in labelled micro centrifuge tube containing $K_2EDTA$ as anticoagulant. Plasma samples were separated by centrifugation at 2500 g for 10 min of whole blood and stored below −70° C. until bioanalysis. All samples were processed for analysis by protein precipitation using acetonitrile and analyzed with LC-MS/MS method (LLOQ=0.50 ng/mL). Pharmacokinetic parameters were calculated using the non-compartmental analysis tool of Phoenix WinNonlin® (Version 6.3).

TABLE 7a

Pharmacokinetic parameters determined from studies involving oral administration of the compound of Example 2.

| Dose & route | Mouse 5 mg/kg p.o. | | Rat 5 mg/kg p.o. | | Dog 1 mg/kg p.o. |
| --- | --- | --- | --- | --- | --- |
| Bio matrix | Plasma | Total colon | Plasma | Total colon | Plasma |
| $T_{max}$ (h) | 1 | 8 | 4 | 8 | — |
| $C_{max}$ (ng/mL) | 12 | 13,671 | 2.7 | 2,005 | — |
| $AUC_{LAST}$ (h · ng/mL) | 49 | 117,473 | 4.8 | 15,528 | — |
| $AUC_{INF}$ (h · ng/mL) | NR | 117,565 | NC | 15,761 | — |
| $F_{po}$ (%) | — | — | 0.04 | — | 0 |

NR—Not reported since the $AUC_{INF}$ is 20% greater than $AUC_{LAST}$.

NC—Not calculated due to insufficient elimination phase.

TABLE 7b

Pharmacokinetic parameters determined from studies involving intravenous administration of the compound of Example 2.

| Dose | Rat 0.25 mg/kg | Dog 0.05 mg/kg |
| --- | --- | --- |
| $C_0$ (ng/mL) | 5,364 | 1,370 ± 1,175 |
| $AUC_{LAST}$ (h · ng/mL) | 682 | 218 ± 90 |
| $AUC_{INF}$ (h · ng/mL) | 691 | 223 ± 92 |
| $T_{1/2}$ (h) | 2.2 | 1.9 ± 0.4 |
| CL (mL/min/kg) | 6.3 | 4.1 ± 1.4 |
| $V_d$ (L/kg) | 0.3 | 0.2 ± 0.1 |

TABLE 7c

Concentrations of the compound of Example 2 determined at different time points in the mouse pharmacokinetic study

| | Mean concentration of the compound of Example 2 (average of 3 experiments) | |
| --- | --- | --- |
| Time (hr) | Plasma (ng/mL) | Colon (ng/g) |
| 1 | 11.7 | 884 |
| 2 | 8.5 | 2807 |
| 4 | 5.1 | 4235 |
| 6 | 4.55 (n = 2) | 1395 |
| 8 | 5.1 | 13671 |
| 12 | 0.0 | 7489 |
| 24 | 0.0 | 31.6 |

TABLE 7d

Concentrations of the compound of Example 2 determined at different time points in the rat pharmacokinetic study

| Time (hr) | Mean concentration of the compound of Example 2 (average of 3 experiments) | |
|---|---|---|
| | Plasma (ng/mL) | Colon (ng/g) |
| Pre-dose | 0.0 | 0.0 |
| | 0.8 | 3.3 |
| 1 | 0.9 | 1.9 (n = 2) |
| 2 | 0.6 | 4.0 (n = 2) |
| 4 | 2.7 | 339 |
| 6 | 1.7 | 1862 |
| 8 | 0.6 | 2005 |
| 12 | 0.7 | 597 |
| 24 | 1.8 | 53.9 |

Determination of ADME Parameters

Assessment of certain in vitro ADME (absorption, distribution, metabolism, and excretion) parameters for the compound of Example 2 was conducted by BioFocus (Saffron Walden, UK).

(i) Metabolic Stability

Hepatic Microsomal Stability

Microsomal stability assays were performed with incubations of test compounds at 0.1 µM (n=2, final DMSO concentration 0.25%), and carried out using pooled human, dog, rat and Cynomolgus macaque hepatic microsomes from Xenotech (Lots 1210153, 0810143 and 1110042, respectively) at 0.25 mg protein/mL in the presence of cofactor, NADPH. The incubations were performed at 37° C. with 100 µL aliquots taken from the incubation, at 0, 2, 5, 10 and 20 minutes (and, in the case of Cynomolgus macaque hepatic microsomes, 40 minutes) and reactions terminated by addition of 100 µL of acetonitrile containing carbamazepine as analytical internal standard. Samples were centrifuged and the supernatant fractions analysed by LC-MS/MS.

The instrument responses (peak heights) were referenced to the zero time-point samples (as 100%) in order to determine the percentage of compound remaining.

Ln plots of the % remaining, for each compound, were used to determine the half-life for the microsomal incubations. Half-life values were calculated from the relationship $$T_{1/2} (min) = -0.693/\lambda$$

where $\lambda$ was the slope of the Ln concentration vs time curve.

The in vitro intrinsic clearance, $Cl_{int}$ (mL/min/kg), was calculated and scaled to hepatic extraction ratios using the following scaling parameters and formulae.

Parameters

| Parameter | Value | | | |
|---|---|---|---|---|
| | Human | Dog | Rat | Monkey |
| Microsomal protein concentration in incubation (mg/mL) | 0.25 | 0.25 | 0.25 | 0.25 |
| microsomes/g liver (mg) | 52 | 78 | 45 | 32 |
| liver weight/kg body weight (g) | 25 | 32 | 50 | 32 |
| hepatic blood flow (mL/min/kg) | 21 | 31 | 60 | 44 |

| Parameter | Value | | | |
|---|---|---|---|---|
| | Human | Dog | Rat | Monkey |

Formulae $Cl_{int}$(tissue clearance) mL/min/kg=[0.693/$t\frac{1}{2}$ (min)]× [1/microsomal protein concentration mg/mL]× [mg microsomes/g liver]×[g liver/kg body weight]

$Cl_{int}$(hepatic clearance) mL/min/kg=hepatic blood flow×$Cl_{int}$/(hepatic blood flow+$Cl_{int}$)

Hepatic extraction ratio($Eh$)=$Cl_{int}$(hepatic clearance) mL/min/kg/hepatic blood flow(mL/min/kg)

A. Cryopreserved Hepatocyte Stability

Hepatocyte stability assays were performed with incubations of test compounds (0.1 µM initial concentration, n=2) carried out with pooled human, dog, rat and Cynomolgus macaque cryopreserved hepatocytes from Celsis (Lot numbers RRW, KLI and WAP, respectively) at a cell density of 0.5 million cells/mL. The incubations were performed at 37° C. with 100 µL, samples taken from the incubation, at 0, 10, 20, 45 and 90 minutes, and reactions terminated by addition of 100 µL of acetonitrile containing carbamazepine as analytical internal standard. Samples were centrifuged and the supernatant fractions analysed by LC-MS/MS.

The instrument responses (peak heights) were referenced to the zero time-point samples (as 100%) in order to determine the percentage of compound remaining.

Ln plots of the % remaining, for each compound, were used to determine the half-life for the hepatocyte incubations. Half-life values were calculated from the relationship $$T_{1/2} (min) = -0.693/\lambda$$

where $\lambda$ was the slope of the Ln concentration vs time curve.

Standard compounds testosterone, midazolam and 4-methylumbelliferone are included in the assay design. These compounds give an indication of the metabolic capacity of the cryopreserved preparations for both Phase I and Phase II reactions.

In vitro intrinsic clearance ($Cl_{int}$), as µL/min/million cells was calculated by applying the following formula to the half-life values:

$$Cl_{int} = 0.693/T\frac{1}{2} (min) \times incubation\ volume(\mu L)/million\ cells$$

The half-life values were also scaled to hepatic extraction ratios using the scaling factors and formulae below.

Parameters

| Parameter | Value | | | |
|---|---|---|---|---|
| | Human | Dog | Rat | Monkey |
| Hepatocyte concentration in incubation (million cells/mL) | 0.5 | 0.5 | 0.5 | 0.5 |
| Hepatocellularity (million cells/g liver) | 120 | 240 | 120 | 120 |
| liver weight/kg body weight (g) | 25 | 32 | 50 | 32 |
| hepatic blood flow (mL/min/kg) | 21 | 31 | 60 | 44 |

$Cl_{int}$(Tissue Clearance) mL/min/kg=[0.693/t½(min)]×
[1/hepatocyte concentration (million cells/mL)]×
[million cells/g liver]×[g liver/kg body weight]

$Cl_{int}$(Hepatic clearance) mL/min/kg=hepatic blood
flow×$Cl_{int}$/(hepatic blood flow+$Cl_{int}$)

Hepatic extraction ratio($Eh$)=$Cl_{int}$(Hepatic clearance)
mL/min/kg/hepatic blood flow (mL/min/kg)

The results catalogued in Tables 8a and 8b indicate that the compound of Example 2 exhibits high hepatic clearance, a feature resulting in lower systemic exposures in an in vivo setting.

TABLE 8a

Summary of hepatic microsome stability tests for the compound of Example 2 (results reported are the arithmetic mean of two experiments).

| Source of hepatic microsomes | Mean intrinsic clearance (μL/min/mg protein) | Mean hepatic extraction ratio (Eh) |
|---|---|---|
| Human | >554 | >0.97 |
| Dog | >554 | >0.98 |
| Rat | 199 | 0.88 |
| Cynomolgus macaque | 445 | 0.91 |

TABLE 8b

Summary of hepatocyte stability tests for the compound of Example 2 (results reported are the arithmetic mean of two experiments).

| Source of hepatocytes | Mean intrinsic clearance (μL/min/million cells) | Mean hepatic extraction ratio (Eh) |
|---|---|---|
| Human | 37 | 0.84 |
| Dog | 46 | 0.92 |
| Rat | 49 | 0.83 |
| Cynomolgus macaque | 43 | 0.80 |

(II) Time-Dependent Inhibition of Cytochromes

CYP450 time-dependent inhibition (TDI) assays were performed with test compound at six test concentrations, 0.062 μM to 15 μM (n=2). The test compounds was pre-incubated for 30 minutes with pooled human hepatic microsomes in 0.1 M Tris buffer, pH 7.4, at 37° C. in the presence of cofactor NADPH. A parallel series of incubations (n=2) were prepared with no pre-incubation. Probe substrates were then added (with additional cofactor) and further incubated for the times specified. Concentrations of probe substrates used in the incubations have been optimised to maintain first order reaction conditions.

Reactions were terminated with acetonitrile containing analytical internal standard (carbamazepine), samples then centrifuged to remove microsomal protein and analysed using optimised LC/MS-MS conditions. The MS data were normalised to internal standard and compared to the appropriate solvent controls to determine the amount of metabolite formed from the probe substrate relative to the "uninhibited" controls. The results are quoted as % inhibition. These values were then plotted using the sigmoidal dose response equation (shown below) and $IC_{50}$'s calculated.

Y=bottom+((top−bottom)/1+10^((Log $IC_{50}$−X)*Hill slope))

X=Log concentration

Y=response $IC_{50}$ is quoted in μM, i.e. the point at which the inhibition is 50% of the control value.

Positive and negative time-dependent inhibitors were included to demonstrate the potential for specific and potent interactions under the conditions used. Variation in probe turnover between plate wells means that inhibition values recorded below 10-15% may not be significant.

A summary of the specific conditions are shown in the table below.

| Cytochrome P450 isoform | Microsome conc. (mg/mL) | Probe substrate Identity | Conc. (μM) | Metabolite | Incubation time (min) |
|---|---|---|---|---|---|
| 3A4 | 0.25 | Midazolam | 7 | 1'-OH-midazolam | 15 |
| 2C9 | 0.25 | Diclofenac | 15 | 1'-OH-diclofenac | 15 |

TABLE 9

Summary of CYP inhibition studies for the compound of Example 2 (results reported are the arithmetic mean of two experiments).

| Cytochrome P450 isoform | 0 min preincubation | | 30 min preincubation | |
|---|---|---|---|---|
| | 15 μM % Inh | $IC_{50}$ (μM) | 15 μM % Inh | $IC_{50}$ (μM) |
| CYP3A4 | 2 | >15 | 52 | 7.7 |
| CYP2C9 | 35 | >15 | 37 | >15 |

Analysis of Metabolites

Studies were conducted by BioFocus (Saffron Walden, UK) to determine the metabolic fate of the compound of Example 2 following incubation with rat, dog, Cynomolgus macaque or human hepatocytes.

Separate incubations (n=3) of the compound of Example 2 (10 μM initial concentration) or DMSO control, were performed with cryopreserved hepatocytes from each species (0.5 million cell/mL) at 37° C. for 0, 60 and 90 minutes before termination of reactions and compound extraction with acetonitrile. Sample replicates were pooled prior to analysis.

Potential metabolites were identified using time-of-flight (TOF) and triple quadruple (TQ) mass spectrometers.

For all types of hepatocytes tested, putative metabolites of the compound of Example 2 were observed at very low levels compared to the abundance of parent compound. The low signal intensity of some metabolites made interpretation and structural assignment problematic. Additionally, the close relationship of the products, and their chromatographic proximity, produced complex mass spectra from which it was not always possible to assign fragment ions to one putative metabolite or another. The high degree of mass resolution afforded by the time-of-flight instrument did, however, provide confidence in the empirical formulae of the structures postulated.

A total of nine metabolites were identified in all studies. Six of the nine metabolites identified, including all of those in human hepatocytes, had empirical formulae that were consistent with oxidative breakdown of the polyethylene glycol (PEG) side-chain of the compound of Example 2. The other three metabolites were observed in studies with either dog or Cynomolgus macaque hepatocytes only.

hERG Inhibition Studies

The compound of Example 2 was tested for inhibition of the human ether a go-go (hERG) channel using IonWorks™ patch clamp electrophysiology at Essen Bioscience (Welwyn Garden City, England). Eight-point concentration curves were generated using serial 3-fold dilutions from the maximum final assay concentration (3 µM). Electrophysiological recordings were made from a Chinese Hamster Lung cell line stably expressing the full length hERG channel Single cell ionic currents were measured in the perforated patch clamp configuration (100 µg/mL) amphotericin) at room temperature (21-23° C.) using an IonWorks Quattro instrument. The internal solution contained (mM): 140 KCl, 1 MgCl$_2$, 1 EGTA, 20 HEPES and was buffered to pH 7.3. The external solution contained (mM):138 NaCl, 2.7 KCl, 0.9 CaCl$_2$, 0.5 MgCl$_2$, 8 Na$_2$HPO$_4$, 1.5 KH$_2$PO$_4$, also buffered to pH 7.3. Cells were clamped at a holding potential of −70 mV for 30 s and then stepped to +40 mV for 1 s. This was followed by a hyperpolarising step of 1 s to −30 mV to evoke the hERG tail current. This sequence was repeated 5 times at a frequency of 0.25 Hz. Currents were measured from the tail step at the 5th pulse, and referenced to the holding current. Compounds were then incubated for 6-7 minutes prior to a second measurement of the hERG signal using an identical pulse train. Eight-point concentration curves were generated using serial 3-fold dilutions from the maximum final assay concentration (3 µM). These studies determined that the compound of Example 2 has an IC$_{50}$ value for the hERG channel of greater than 3 µM (0±4% inhibition of the channel being observed at 3 µM concentration of the compound of Example 2).

Diversity Profile

Studies were conducted by Cerep (Celle-Lévescault, France) to investigate the binding of the compound of Example 2 to a diverse selection of receptors and to investigate either the inhibition or activation of a selection of enzymes (the "Diversity Profile" comprising a total of 71 receptors and 26 enzymes).

When studied at a concentration of 300 nM the compound of Example 2 did not significantly bind to any of the receptors or inhibit/activate the enzymes tested (i.e. it inhibited the control specific binding in the receptor binding assays or enzyme assays by less than 25%, as assessed using a suitable radioligand for each receptor or a suitable reference substrate for each enzyme).

Mutagenicity Assessment (Bacterial Reverse Mutation Screen)

Studies were conducted by Sequani (Ledbury, Herefordshire, UK) to assess the compound of Example 2 in vitro for its ability to induce mutations in two histidine dependent auxotrophic mutants of *Salmonella typhimurium*, strains TA98 and TA100.

The mutation screen was conducted using the plate incorporation method and was performed in both the presence and absence of S-9 mix (a liver post-mitochondrial fraction derived from the livers of Aroclor 1254 treated rats). The bacteria were exposed to the compound of Example 2 dissolved in dimethylsulphoxide, which solvent was also used as the negative control. The dose levels used were 0.32, 1.6, 8, 40, 200, 1000 or 5000 µg/plate.

Analysable treatment levels of the compound of Example 2 were limited by insolubility to 1000 µg/plate, as heavy precipitation observed at 5000 µg/plate affected the scoring of the colonies. Precipitation was also noted in both strains at 1000 µg/plate in the presence and absence of S-9 mix.

The compound of Example 2 showed no dose-related or statistically significant increases in revertant colonies in either *Salmonella typhimurium* strain in the presence or absence of S-9 mix. This indicates the absence of any mutagenic effects for the compound of Example 2 in the *Salmonella typhimurium* strains studied.

Hydrolytic Stability Study

Chemical stability of the compound of Example 2 was assessed in a mixture of DMSO and water (3:1) at a test compound concentration of 1 mg/mL General HPLC Procedure
  Agilent, Waters X-Select C18, 2.5 µm, 4.6×30 mm column, 4 min method, 5-95% MeCN/water (0.1% formic acid).
Flow rate 2.5 ml/min
Column Oven Temperature 40° C.
Detection 254 nm.
Sample Preparation
  A 1.0 mg sample of test compound was dissolved in 750 µL of DMSO. Water (250 µL) was added slowly, ensuring no precipitation occurred.
Recording Stability
  A 50 µL aliquot of the test solution was removed and analysed in duplicate by 5 µL HPLC injections. The peak area for the test compound was recorded following manual integration of the corresponding UV trace.

The test solution was heated to 60° C., with stirring, and 50 µL aliquots removed for HPLC analysis at 5 and 24 h timepoints. In all cases, 5 µL injections were used and the samples analysed in duplicate.

The peak area for the test compound was recorded at both subsequent timepoints and the % decomposition calculated from the % change in peak area over time.

Reference Compound A (3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide) was included in each stability study as a control to validate the study.

The results of the study are reported in the table below.

| Test Compound | Time (min) | % left |
|---|---|---|
| Reference Compound A | 0 | 100 |
|  | 300 | 82 |
|  | 1440 | 36 |
| Example 2 | 0 | 100 |
|  | 300 | 83 |
|  | 1440 | 39 |

Chemical stability of the compound of Example 2 (in solid form) was also assessed at 40° C. and 75% relative humidity. The results of the study are reported in the table below (where chemical purity was assessed using HPLC).

| Compound | Condition | | |
|---|---|---|---|
| | 0 months | 1 month, 40° C./75% RH | 3 months, 40° C./75% RH |
| Example 2 | 98.52% | 96.88% | 94.32% |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

What is claimed is:
1. A compound of formula (III),

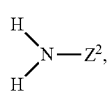

or a salt or protected derivative thereof, wherein $Z^2$ represents a structural fragment of formula (V),

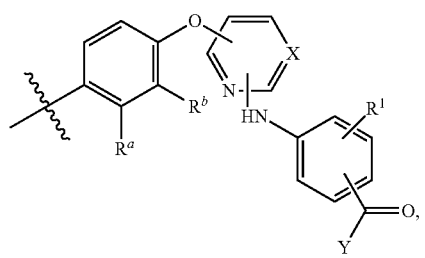

wherein:
X represents CH or N,
Y represents $NR^2R^3$;
$R^a$ and $R^b$, together with the C-atoms to which they are attached, form a fused phenyl ring that is optionally substituted by one or more substituents selected from the group consisting of $C_{1-3}$ alkyl, $C_{1-3}$ haloalkyl, cyano and halo,
or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl
or $R^a$ and $R^b$ together represent $C_{3-5}$ n-alkylene, which alkylene group is optionally substituted by one or more methyl substituents and/or which alkylene group optionally contains one C—C double bond between two C-atoms of the n-alkylene chain;
$R^1$ is selected from the group consisting of hydrogen, OH, halogen, CN, $C_{1-6}$ alkyl, $C_{2-6}$ alkenyl, $C_{2-6}$ alkynyl, $C_{1-6}$ haloalkyl, $C_{0-3}$ alkylene-$C_{3-6}$ cycloalkyl, $C_{0-3}$ alkylene-O—$C_{1-3}$ alkylene-$C_{3-6}$ cycloalkyl, $C_{1-6}$ alkoxy, $C_{1-6}$ haloalkoxy, $C_{1-6}$ hydroxyalkyl, $C_{0-3}$ alkylene-$SO_2C_{1-3}$alkyl, $C_{0-3}$ alkylene-$SO_2NR^4R^5$, and $C_{0-3}$ alkylene-$NR^6R^7$ and $C_{0-3}$ alkylene-$NCOR^6R^7$;
one of $R^2$ and $R^3$ represents —$[C_{2-4}$ alkylene-O$]_{1-12}$— $[C_{2-4}$ alkylene]-$R^{2a}$ and the other of $R^2$ and $R^3$ is selected from the group consisting of H, $C_{1-8}$ alkyl, $C_{0-6}$ alkylene aryl, $C_{0-6}$ alkylene heteroaryl, —$[C_{2-4}$ alkylene-O$]_{0-12}$—$[C_{2-4}$ alkylene]-$R^{2a}$, $C_{0-6}$ alkylene-4-10 membered heterocycle, and $C_{0-3}$ alkylene-O—$C_{0-6}$ alkylene-4-10 membered heterocycle with the proviso that when the said heterocycle is linked through nitrogen there are at least two C-atoms in the alkylene chain that links that nitrogen atom to the essential O atom of the substituent, wherein independently each alkyl or alkylene group optionally bears 1 oxo substituent, and optionally one or two carbon atoms in the alkyl or alkylene chain may each be replaced by a heteroatom selected from the group consisting of O, N and $S(O)_p$, such that when said alkyl or alkylene comprises an amine said amino group is a tertiary amine,
wherein each 4-10 membered heterocycle is optionally substituted by 1 or 2 groups independently selected from the group consisting of halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$C_{0-3}$ alkylene aryl, $C_{0-6}$ alkylene heteroaryl, $C_{0-3}$ alkylene-O—$C_{0-3}$ alkylene heteroaryl, $C(O)C_{1-6}$ alkyl, $SO_2NR^8R^9$, and $C_{0-3}$ alkylene-$NR^8R^9$, $C_{0-3}$ alkylene-$NR^8SO_2R^9$ and $C_{0-3}$ alkylene-$NR^8C(O)R^9$;
$R^{2a}$ represents $OR^{2b}$ or $N(R^{2c})R^{2d}$;
$R^{2b}$ to $R^{2d}$ independently represent H or $C_{1-4}$ alkyl optionally substituted by one or more halo atoms, or $R^{2c}$ and $R^{2d}$ together represent
$C_{3-6}$ n-alkylene,
$C_{4-5}$ n-alkylene interrupted between C2 and C3 by —O— or —$N(R^{2e})$— or
$C_6$ n-alkylene interrupted between C2 and C3, or between C3 and C4, by —O— or —$N(R^{2e})$—,
any of which n-alkylene groups are optionally substituted by one or more substituents selected from the group consisting of halo, hydroxy, oxo, $C_{1-4}$ alkyl and $C_{1-4}$ alkoxy;
$R^{2e}$ represents H or $C_{1-6}$ alkyl optionally substituted by one or more substituents selected from the group consisting of halo and hydroxy;
$R^4$ is H or $C_{1-4}$ alkyl;
$R^5$ is H or $C_{1-4}$ alkyl,
$R^6$ is H or $C_{1-4}$ alkyl, $C(O)C_{1-3}$alkyl and $SO_2C_{1-3}$ alkyl;
$R^7$ is H or $C_{1-4}$ alkyl, $C(O)C_{1-3}$alkyl and $SO_2C_{1-3}$ alkyl;
$R^8$ is H or $C_{1-4}$ alkyl,
$R^9$ is H or $C_{1-4}$ alkyl and
p is 0, 1 or 2,
wherein said protected derivative is a compound in which a H-atom of the $NH_2$ group of the compound of formula (III) is replaced by:
R'—C(O)—, wherein R' is H, $C_{1-8}$ alkyl, phenyl or benzyl, which latter two groups are optionally substituted by one or more groups selected from the group consisting of halo, hydroxy, methyl and methoxy; or
R"—O—C(O)—, wherein R" is tert-butyl, phenyl, benzyl or fluorenyl, which latter three groups are optionally substituted by one or more groups selected from the group consisting of halo, hydroxy, methyl and methoxy.

2. A compound according to claim 1, wherein:
$R^a$ and $R^b$, together with the C-atoms to which they are attached, form a fused phenyl ring that is unsubstituted;
X represents CH or N;
$R^1$ represents ethynyl or $OCH_3$;
Y represents $NR^2R^3$;
$R^2$ represents $—(CH_2CH_2O)_{2-4}CH_3$; and
$R^3$ is H,
wherein the protected derivative is a compound in which a H-atom of the $NH_2$ group of formula (III) is replaced by:
R'—C(O)—, wherein R' is H, $C_{1-8}$ alkyl, phenyl or benzyl, which latter two groups are optionally substituted by one or more groups selected from the group consisting of halo, hydroxy, methyl and methoxy, or
R"—O—C(O)—, wherein R" is tert-butyl, phenyl, benzyl or fluorenyl, which latter three groups are optionally substituted by one or more groups selected from the group consisting of halo, hydroxy, methyl and methoxy.

3. A compound according to claim 1 which has the following structure:

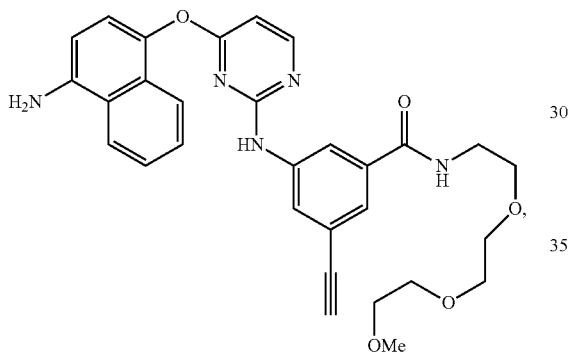

(3-((4-((4-aminonaphthalen-1-yl)oxy)pyrimidin-2-yl)amino)-5-ethynyl-N-(2-(2-(2-methoxyethoxy)ethoxy)ethyl)benzamide), or a salt thereof.

4. A compound according to claim 1 which has the following structure:

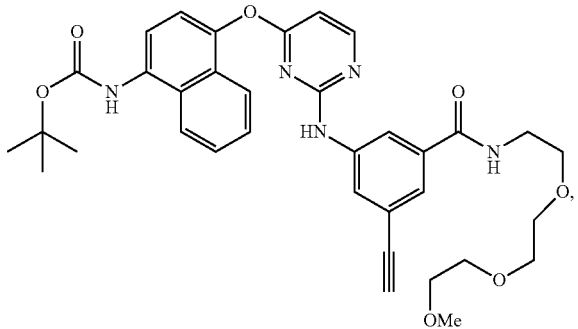 [SMILES: C#Cc1cc(Nc2nccc(Oc3ccc(NC(=O)OC(C)(C)C)c4ccccc34)n2)cc(C(=O)NCCOCCOCCOC)c1]

(tert-butyl (4-((2-((3-ethynyl-5-((2-(2-(2-methoxyethoxy)ethoxy)ethyl)carbamoyl)phenyl)-amino)pyrimidin-4-yl)oxy)naphthalen-1-yl)carbamate), or a salt thereof.

* * * * *